US007771929B2

(12) United States Patent
Singh et al.

(10) Patent No.: US 7,771,929 B2
(45) Date of Patent: *Aug. 10, 2010

(54) TAG LIBRARY COMPOUNDS, COMPOSITIONS, KITS AND METHODS OF USE

(75) Inventors: Sharat Singh, San Jose, CA (US); Tracy Matray, San Lorenzo, CA (US); Hossein Salimi-Moosavi, Sunnyvale, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 1463 days.

This patent is subject to a terminal disclaimer.

(21) Appl. No.: 10/420,549

(22) Filed: Apr. 18, 2003

(65) Prior Publication Data

US 2004/0063114 A1 Apr. 1, 2004

Related U.S. Application Data

(63) Continuation of application No. 09/602,586, filed on Jun. 21, 2000, now Pat. No. 6,514,700, which is a continuation of application No. 09/561,579, filed on Apr. 28, 2000, now Pat. No. 6,682,887.

(51) Int. Cl.
*C07B 61/00* (2006.01)
*C07H 21/00* (2006.01)
(52) U.S. Cl. .............................. 435/6; 506/30; 506/41; 536/25.32
(58) Field of Classification Search .................... 435/6, 435/7.1, 7.2, 7.7, 7.95
See application file for complete search history.

(56) References Cited

U.S. PATENT DOCUMENTS

| | | | |
|---|---|---|---|
| 4,274,240 A | 6/1981 | Soum | 52/583 |
| 4,331,590 A | 5/1982 | Bocuslaski | 260/112 B |
| 4,650,750 A | 3/1987 | Giese | 435/7 |
| 4,675,300 A | 6/1987 | Zare | 436/172 |
| 4,709,016 A | 11/1987 | Giese | 530/389 |
| 4,780,421 A | 10/1988 | Kameda | 436/518 |
| 5,057,412 A | 10/1991 | Rabin | 435/6 |
| 5,137,609 A | 8/1992 | Manian | |
| 5,231,178 A | 7/1993 | Holtz et al. | |
| 5,254,469 A | 10/1993 | Warren, III | 435/188 |
| 5,324,401 A | 6/1994 | Yeung | 204/180.1 |
| 5,340,716 A | 8/1994 | Ullman | 435/6 |
| 5,360,819 A | 11/1994 | Giese | 514/538 |
| 5,470,705 A | 11/1995 | Grossman | 435/6 |
| 5,494,793 A | 2/1996 | Schindele | 435/6 |
| 5,514,543 A | 5/1996 | Grossman | 435/6 |
| 5,516,636 A | 5/1996 | McCapra | 435/6 |
| 5,516,931 A | 5/1996 | Giese | 560/59 |
| 5,536,834 A | 7/1996 | Singh | 544/98 |
| 5,560,811 A | 10/1996 | Briggs | 204/451 |
| 5,565,324 A | 10/1996 | Still | 435/6 |
| 5,567,292 A | 10/1996 | Madabhushi | 204/451 |
| 5,571,680 A | 11/1996 | Chen | |
| 5,573,906 A | 11/1996 | Bannwarth | 435/6 |
| 5,578,498 A | 11/1996 | Singh | 436/518 |
| 5,580,732 A | 12/1996 | Grossman | 435/6 |
| 5,602,273 A | 2/1997 | Giese | 560/60 |
| 5,604,104 A | 2/1997 | Giese | 435/7.1 |
| 5,610,020 A | 3/1997 | Giese | 435/7.1 |
| 5,616,719 A | 4/1997 | Davalian | 546/334 |
| 5,622,929 A | 4/1997 | Willner | 514/8 |
| 5,624,800 A | 4/1997 | Grossman | 435/6 |
| 5,643,728 A | 7/1997 | Slater | 435/6 |
| 5,650,270 A | 7/1997 | Giese | 435/6 |
| 5,691,151 A | 11/1997 | Braun | 435/7.2 |
| 5,703,222 A | 12/1997 | Grossman | 536/24.3 |
| 5,705,622 A | 1/1998 | McCapra | 536/23.1 |
| 5,709,994 A | 1/1998 | Pease | 435/4 |
| 5,719,028 A | 2/1998 | Dahlberg | 435/6 |
| 5,721,099 A | 2/1998 | Still | 435/6 |
| 5,723,591 A | 3/1998 | Livak | 536/22.1 |

(Continued)

FOREIGN PATENT DOCUMENTS

EP 0 484 027 A1 5/1992

(Continued)

OTHER PUBLICATIONS

Caslavska, J. et al., "Analysis of Urinary Drugs of Abuse by a Multianalyte Capillary Electrophoretic Immunosassay," *J Chromatogr A*. Apr. 9, 1999;838(1-2):197-211.
Chen, FT. et al., "Feasibility Studies for Simultaneous Immunochemical Multianalysis Drug Assay by Capillary Electrophoresis with Laser-Induced Fluorescence." Clin Chem. Sep. 1994;40(9):1819-22.
Adam et al., "Photooxygenation (Singlet Oxygen) of Tetrathioethylenes", Journal of the American Chemical Society, vol. 94:4, 1972, pp. 1206-1208.
Ando et al., "Photosensitized Oxygenation of Vinylic Sulphides", J.C.S. Chem. Comm., 1972, pp. 477-478.

(Continued)

*Primary Examiner*—Lisa J Hobbs
(74) *Attorney, Agent, or Firm*—Kilpatrick Stockton LLP

(57) ABSTRACT

Families of compositions are provided as labels, referred to as eTag reporters for attaching to polymeric compounds and assaying based on release of the eTag reporters from the polymeric compound and separation and detection. For oligonucleotides, the eTag reporters are synthesized at the end of the oligonucleotide by using phosphite or phosphate chemistry, whereby mass-modifying regions, charge-modifying regions and detectable regions are added sequentially to produce the eTag labeled reporters. By using small building blocks and varying their combination large numbers of different eTag reporters can be readily produced attached to a binding compound specific for the target compound of interest for identification. Protocols are used that release the eTag reporter when the target compound is present in the sample.

6 Claims, 21 Drawing Sheets

U.S. PATENT DOCUMENTS

| | | | |
|---|---|---|---|
| 5,756,726 A | 5/1998 | Hemmi | 540/474 |
| 5,763,602 A | 6/1998 | Li | 540/128 |
| 5,766,481 A | 6/1998 | Zambias | 210/656 |
| 5,777,096 A | 7/1998 | Grossman | 536/24.3 |
| 5,789,172 A | 8/1998 | Still | 435/6 |
| 5,807,675 A | 9/1998 | Davalian | 435/6 |
| 5,807,682 A | 9/1998 | Grossman | 435/6 |
| 5,811,239 A | 9/1998 | Frayne | 435/6 |
| 5,843,655 A | 12/1998 | McGall | 435/6 |
| 5,843,666 A * | 12/1998 | Akhavan-Tafti et al. | 435/6 |
| 5,843,680 A | 12/1998 | Manian | |
| 5,846,839 A | 12/1998 | Gallop | 436/518 |
| 5,849,878 A | 12/1998 | Cantor | 530/391.9 |
| 5,851,770 A | 12/1998 | Babon | 435/6 |
| 5,874,213 A | 2/1999 | Cummins | 435/6 |
| 5,876,930 A | 3/1999 | Livak | 435/6 |
| 5,898,005 A | 4/1999 | Singh | 436/527 |
| 5,916,426 A | 6/1999 | Madabhushi | 204/451 |
| 5,952,654 A | 9/1999 | Giese | 250/288 |
| 5,958,202 A | 9/1999 | Regnier | 204/451 |
| 5,981,180 A | 11/1999 | Chandler | 435/6 |
| 5,986,076 A | 11/1999 | Rothschild | 536/22.1 |
| 5,989,871 A | 11/1999 | Grossman | 435/91.1 |
| 5,994,069 A | 11/1999 | Hall et al. | |
| 5,998,140 A | 12/1999 | Dervan | 435/6 |
| 6,001,567 A | 12/1999 | Brow | 435/6 |
| 6,001,579 A | 12/1999 | Still | 435/7.1 |
| 6,027,890 A | 2/2000 | Ness | 435/6 |
| 6,045,676 A | 4/2000 | Mathies | 204/603 |
| 6,090,947 A | 7/2000 | Dervan | 548/312.4 |
| 6,251,581 B1 | 6/2001 | Ullman | 435/4 |
| 6,312,893 B1 | 11/2001 | Van Ness | 435/6 |
| 6,322,980 B1 | 11/2001 | Singh | 435/6 |
| 6,331,530 B1 | 12/2001 | Breslow | 514/58 |
| 6,335,201 B1 | 1/2002 | Allbritton | 436/63 |
| 6,346,384 B1 | 2/2002 | Pollner | 435/6 |
| 6,346,529 B1 | 2/2002 | Floyd | 514/226.2 |
| 6,627,400 B1 * | 9/2003 | Singh et al. | 435/6 |
| 6,949,347 B2 | 9/2005 | Singh et al. | |
| 7,160,735 B2 | 1/2007 | Dehlinger et al. | |
| 7,358,052 B2 | 4/2008 | Singh | |
| 2001/0049105 A1 | 12/2001 | Singh et al. | |
| 2002/0037542 A1 | 3/2002 | Allbritton | 435/7.23 |
| 2002/0045178 A1 | 4/2002 | Cantor et al. | |
| 2002/0098478 A1 | 7/2002 | Wold | |
| 2002/0128465 A1 | 9/2002 | Lyamichev | 536/24.3 |

FOREIGN PATENT DOCUMENTS

| | | |
|---|---|---|
| EP | 0552931 A1 | 7/1993 |
| WO | WO 93/06121 | 4/1993 |
| WO | WO 96/24061 | 8/1996 |
| WO | WO 97/27325 | 7/1997 |
| WO | WO 97/27327 | 7/1997 |
| WO | WO 97/28275 | 8/1997 |
| WO | WO 98/01533 | 1/1998 |
| WO | WO 98/15830 | 4/1998 |
| WO | WO 99/05319 | 2/1999 |
| WO | WO 99/13108 | 3/1999 |
| WO | WO 99/42838 | 8/1999 |
| WO | WO 99/64519 | 12/1999 |
| WO | WO 00/56925 | 9/2000 |
| WO | WO 00/66607 | 11/2000 |
| WO | WO 02/29109 A2 | 4/2002 |
| WO | WO 02/083954 A2 | 10/2002 |
| WO | WO 02/097112 A2 | 12/2002 |

OTHER PUBLICATIONS

Giese, "Electrophoric Release Tags: Ultrasensitive Molecular Labels Providing Multiplicity", Trends in Analytical Chemistry, vol. 2, No. 7, 1983, pp. 166-168.

Holland et al., "Detection of Specific Polymerase Chain Reaction Product by Utilizing the 5' → 3' Exonuclease Activity of *Thermus Aquaticus* DNA Polymerase", Proc. Natl. Acad. Sci. USA, vol. 88, 1991, pp. 7276-7280.

Houghten et al., "Human β -Endorphin: Synthesis and Characterization of Analogs Iodinated and Tritiated at Tryosine Residues 1 and 27", Int. J. Peptide Protein Res., vol. 16, 1980, pp. 311-320.

Kochevar et al., "Photosensitized Production of Singlet Oxygen", Methods in Enzymology, vol. 319, 2000, pp. 20-29.

Lee et al., "Allelic Discrimination by Nick-Translation PCR with Fluorogenic Probes", Nucleic Acids Research, vol. 21, No. 16, 1993, pp. 3761-3766.

Liu et al., "Capillary Electrochromatography-laser-induced Fluorescence Method for Separation and Detection of Dansylated Dialkylamine Tags in Encoded Combinatorial Libraries", Journal of Chromatorgraphy, Art. 924, 2001, pp. 323-329.

Lu et al., "Polymerizable Fab' Antibody Fragments for Targeting of Anticancer Drugs", Nature Biotechnology, vol. 17, 1999, pp. 1101-1104.

Lum et al., "Ability of Specific Monoclonal Antibodies and Conventional Antisera Conjugated to Hematoporphyrin to Label and Kill Selected Cell Lines Subsequent to Light Activation", Cancer Research, vol. 45, 1985, pp. 4380-4386.

Marglin et al., "Chemical Synthesis of Peptides and Proteins", Art. 739, 1970, pp. 841-866.

Marino et al., "Characterization of Mitochondrial DNA Using Low-Stringency Single Specific Primer Amplification Analyzed by Laser Induced Fluoroscene—Capillary Electrophoresis", Electrophoresis, vol. 17, 1996, pp. 1499-1504.

Matthews et al., "Analytical Strategies for the Use of DNA Probes", Analytical Biochemistry, vol. 169, 1988, pp. 1-25.

Merrifield, "Solid Phase Peptide Synthesis. I. The Synthesis of a Tetrapeptide", Synthesis of a Tetrapeptide, vol. 85, 1963, pp. 2149-2154.

Ni et al., "Versatile Approach to Encoding Combinatorial Organic Synthesis Using Chemically Robust Secondary Amine Tags", J. Med. Chem., vol. 39, 1996, pp. 1601-1608.

Olejnik et al., "Photocleavable Affinity Tags for Isolation and Detection of Biomolecules", Methods in Enzymology, vol. 291, 1998, pp. 135-154.

Oseroff et al., "Antibody-Targeted Photolysis: Selective photodestruction of Human T-Cell Leukemia Cells Using Monoclonal Antibody-Chlorin $e_6$ Conjugates", Proc. Natl. Acad. Sci. USA, vol. 83, 1986, pp. 8744-8748.

Pastinen et al., "Multiplex, Fluorescent, Solid-Phase Minisequencing for Efficient Screening of DNA Sequence Variation", Clinical Chemistry, vol. 42:9, 1996, pp. 1391-1397.

Posewitz et al., "Immobilized Gallium(III) Affinity Chromatography of Phosphopeptides", Anal. Chem., vol. 71, 1999, pp. 2883-2892.

Rakestraw et al., "Antibody-Targeted photolysis: In vitro Studies with Sn(IV) Chlorin e6 Covalently Bound to Monoclonal Antibodies Using a Modified Dextran Carrier", Proc. Natl. Acad. Sci. USA, vol. 87, 1990, pp. 4217-4221.

Da Ros et al., "DNA-Photocleavage Agents", Current Pharmaceutical Design, vol. 7, 2001, pp. 1781-1821.

Ross et al., "Discrimination of Single-Nucleotide Polymorphisms in Human DNA Using Peptide Nucleic Acid Probes Detected by MALDI-TOF Mass Spectrometry", Anal. Chem., vol. 69, 1997, pp. 4197-4202.

Sharman et al., "Role of Activated Oxygen Species in Photodynamic Therapy", Methods in Enzymology, vol. 319, 2000, pp. 376-400.

Still, "Discovery of Sequence-Selective Peptide Binding by Synthetic Receptors Using Encoded Combinatorial Libraries", Acc. Chem. Res., vol. 29, 1996, pp. 155-163.

Strong, "Antibody-Targeted Photolysis", Annals New York Academy of Sciences, vol. 745, 1994, pp. 297-320.

Ullman et al., "Luminescent Oxygen Channeling Immunoassay: Measurement of Particle Binding Kinetics by Chemiluminescence", Proc. Natl. Acad. Sci. USA, vol. 91, 1994, pp. 5426-5430.

Wang et al., "Large-Scale Identification, Mapping, and Genotyping of Single-Nucleotide Polymorphisms in the Human Genome", Science, vol. 280, 1998, pp. 1077-1082.

Wasserman et al., "Enamine-Single Oxygen Reactions. α-Diketones from Intermediate Amino Dioxetanes", Tetrahedron Letters, No. 21, 1975, pp. 1735-1738.

Wetmur, "DNA Probes: Applications of the Principles of Nucleic Acid Hybridization", Critical Reviews in Biochemistry and Molecular Biology, vol. 26, 1991, pp. 227-259.

White, "The Future of PCR Technology: Diversification of Technologies and Applications", Tibtech, vol. 14, 1996, pp. 478-483.

Wöhrle, "Porphyrins, Phthalocyanines, and Naphthalocyanines for Various Processes fo Visible Light Driven Conversion Processes", Chimia, vol. 45, 1991, pp. 307-310.

Woolley et al., "Functional Integration of PCR Amplification and Capillary Electrophoresis in a Microfabricated DNA Analysis Device", Anal. Chem., vol. 68, 1996, pp. 4081-4086.

Yarmush et al., "Antibody Targeted Photolysis", Critical Reviews in Therapeutic Drug Carrier Systems, vol. 10, 1993, pp. 197-252.

Yemul et al., "Selective Killing of T Lymphocytes by Phototoxic Liposomes", Proc. Natl. Acad. Sci. USA, vol. 84, 1987, pp. 246-250.

Zaklika et al., "Mechanisms of 1,2-Dioxetane Decomposition: The Role of Electron Transfer", Photochemistry and Photobiology, vol. 30, 1979, pp. 35-44.

Beaudet et al, "Homogeneous Assays for Single-Nucleotide Polymorphism Typing Using AplhaScreen", Genome Research, 11-600-608.

Bangs Laboratories, Inc., "Working with Microspheres", Tech Note #201, Rev. #001, Active: Aug. 29, 1999, pp. 1-16.

European Supplementary Search Report, European Application No. 03815205.4, Jan. 10, 2008, 6 pages.

Shinmura, K. et al., "8-hydroxyguanine (7, 8-dihydro-8-oxoguanine) DNA Glycosylase and AP Lyase Activities of hOGG1 Protein and Their Substrate Specificity," Mutation Research, 1997, pp. 75-82, vol. 385.

* cited by examiner

ACLA070

ACLA071

ACLA072

ACLA073

ACLA074

ACLA075

ACLA076

ACLA077

ACLA078

ACLA089

ACLA090

ACLA091

ACLA092

ACLA093

ACLA094

ACLA095

ACLA096

ACLA097

SEQUENCE LISTING

```
<160> NUMBER OF SEQ ID NOS: 1

<210> SEQ ID NO 1
<211> LENGTH: 11
<212> TYPE: DNA
<213> ORGANISM: Human

<400> SEQUENCE: 1
ctctcagttc t                                                        11
```

TAG LIBRARY COMPOUNDS, COMPOSITIONS, KITS AND METHODS OF USE

CROSS-REFERENCE TO RELATED APPLICATIONS

This application is a continuing patent application of application Ser. No. 09/602,586, filed Jun. 21, 2000, now U.S. Pat. No. 6,514,700 which is a continuing application of application Ser. No. 09/561,579, filed Apr. 28, 2000 now U.S. Pat. No. 6,682,887.

INTRODUCTION

1. Field of the Invention

The field of this invention is separable compositions for use in multiplexed assay detection.

2. Background of the Invention

As the human genome is elucidated, there will be numerous opportunities for performing assays to determine the presence of specific sequences, distinguishing between alleles in homozygotes and heterozygotes, determining the presence of mutations, evaluating cellular expression patterns, etc. In many of these cases one will wish to determine in a single reaction, a number of different characteristics of the same sample. Also, there will be an interest in determining the presence of one or more pathogens, their antibiotic resistance genes, genetic subtype and the like.

In many assays, there will be an interest in determining the presence of specific sequences, whether genomic, synthetic or cDNA. These sequences may be associated particularly with genes, regulatory sequences, repeats, multimeric regions, expression patterns, and the like There is and will continue to be comparisons of the sequences of different individuals. It is believed that there will be about one polymorphism per 1,000 bases, so that one may anticipate that there will be an extensive number of differences between individuals. By single nucleotide polymorphism (snp's) is intended that there will be a prevalent nucleotide at the site, with one or more of the remaining bases being present in substantially smaller percent of the population.

For the most part, the snp's will be in non-coding regions, primarily between genes, but will also be present in exons and introns. In addition, the great proportion of the snp's will not affect the phenotype of the individual, but will clearly affect the genotype. The snp's have a number of properties of interest. Since the snp's will be inherited, individual snp's and/or snp patterns may be related to genetic defects, such as deletions, insertions and mutations involving one or more bases in genes. Rather than isolating and sequencing the target gene, it will be sufficient to identify the snp's involved.

In addition, the snp's may be used in forensic medicine to identify individuals. While other genetic markers are available, the large number of snp's and their extensive distribution in the chromosomes, make the snp's an attractive target. Also, by determining a plurality of snp's associated with a specific phenotype, one may use the snp pattern as an indication of the phenotype, rather than requiring a determination of the genes associated with the phenotype.

The need to determine many analytes or nucleic acid sequences (for example multiple pathogens or multiple genes or multiple genetic variants) in blood or other biological fluids has become increasingly apparent in many branches of medicine. The need to study differential expression of multiple genes to determine toxicologically-relevant outcomes or the need to screen transfused blood for viral contaminants with high sensitivity is clearly evident.

Thus most multi-analyte assays or assays which detect multiple nucleic acid sequences involve multiple steps, have poor sensitivity and poor dynamic range (2 to 100-fold differences in concentration of the analytes is determined) and some require sophisticated instrumentation.

Some of the known classical methods for multianalyte assays include the following:

a. The use of two different radioisotope labels to distinguish two different analytes.

b. The use of two or more different fluorescent labels to distinguish two or more analytes.

c. The use of lanthanide chelates where both lifetime and wavelength are used to distinguish two or more analytes.

d. The use of fluorescent and chemiluminescent labels to distinguish two or more analytes.

e. The use of two different enzymes to distinguish two or more analytes.

f. The use of enzyme and acridinium esters to distinguish two or more analytes.

g. Spatial resolution of different analytes, for example, on arrays to identify and quantify multiple analytes.

h. The use of acridinium ester labels where lifetime or dioxetane formation is used to quantify two different viral targets.

Thus an assay that has higher sensitivity, large dynamic range ($10^3$ to $10^4$-fold differences in target levels), greater degree of multiplexing, and fewer and more stable reagents would increase the simplicity and reliability of multianalyte assays.

The need to identify and quantify a large number of bases or sequences potentially distributed over centimorgans of DNA offers a major challenge. Any method should be accurate, reasonably economical in limiting the amount of reagents required and providing for a single assay, which allows for differentiation of the different snp's or differentiation and quantitation of multiple genes.

Finally, while nucleic acid sequences provide extreme diversity for situations that may be of biological or other interest, there are other types of compounds, such as proteins in proteomics that may also offer opportunities for multiplexed determinations.

BRIEF DESCRIPTION OF RELATED ART

Holland (*Proc. Natl. Acad. Sci. USA* (1991)88:7276) discloses the exonuclease activity of the thermostable enzyme Thermus aquaticus DNA polymerase in PCR amplification to generate specific detectable signal concomitantly with amplification.

The TaqMan assay is discussed by Lee in *Nucleic Acid Research* (1993)21:16 3761).

White (Trends Biotechnology (1996)14(12):478-483) discusses the problems of multiplexing in the TaqMan® assay.

Marino, *Electrophoresis* (1996)17:1499 describes low-stringency-sequence specific PCR (LSSP-PCR). A PCR amplified sequence is subjected to single primer amplification under conditions of low stringency to produce a range of different length amplicons. Different patterns are obtained when there are differences in sequence. The patterns are unique to an individual and of possible value for identity testing.

Single strand conformational polymorphism (SSCP) yields similar results. In this method the PCR amplified DNA is denatured and sequence dependent conformations of the single strands are detected by their differing rates of migration during gel electrophoresis. As with LSSP-PCR above, different patterns are obtained that signal differences in sequence. However, neither LSSP-PCR nor SSCP gives specific sequence information and both depend on the questionable assumption that any base that is changed in a sequence will give rise to a conformational change that can be detected.

Pastinen, *Clin. Chem*. (1996)42:1391 amplifies the target DNA and immobilizes the amplicons. Multiple primers are then allowed to hybridize to sites 3' and contiguous to a snp ("single nucleotide polymorphism") site of interest. Each primer has a different size that serves as a code. The hybridized primers are extended by one base using a fluorescently labeled dideoxynucleoside triphosphate. The size of each of the fluorescent products that is produced, determined by gel electrophoresis, indicates the sequence and, thus, the location of the snp. The identity of the base at the snp site is defined by the triphosphate that is used. A similar approach is taken by Haff, *Nucleic Acids Res*. (1997)25:3749 except that the sizing is carried out by mass spectroscopy and thus avoids the need for a label. However, both methods have the serious limitation that screening for a large number of sites will require large, very pure primers that can have troublesome secondary structures and be very expensive to synthesize.

Hacia, *Nat. Genet*. (1996)14:441 uses a high-density array of oligonucleotides. Labeled DNA samples are allowed to bind to 96,600 20-base oligonucleotides and the binding patterns produced from different individuals were compared. The method is attractive in that SNP's can be directly identified, but the cost of the arrays is high and non-specific hybridization may confound the accuracy of the genetic information.

Fan (Oct. 6-8, 1997 IBC, Annapolis Md.) has reported results of a large scale screening of human sequence-tagged sites. The accuracy of single nucleotide polymorphism screening was determined by conventional ABI resequencing.

Allele specific oligonucleotide hybridization along with mass spectroscopy has been discussed by Ross in *Anal. Chem*. (1997)69:4197.

Holland, et al., PNAS USA (1991)88, 7276-7280, describes use of DNA polymerase 5'-3' exonuclease activity for detection of PCR products.

U.S. Pat. No. 5,807,682 describes probe compositions for detecting a plurality of nucleic acid targets.

SUMMARY OF THE INVENTION

Compounds and methods are provided for multiplexed determinations affording convenient separation of released identifying tags based on individual physical, properties of the tags. The methods can be performed in a single vessel and may involve a plurality of reagents added simultaneously or consecutively. In one group of embodiments, mass will be involved in the characteristic allowing for separation. One group of identifying tags for electrokinetic analysis is characterized by having regions, which serve as (1) a cleavable linking region; (2) a mass-modifying region; (3) a charge-modifying region: and (4) a detectable region, the number of different regions depending in part on the method of separation and identification. Compounds that have these distinctive regions find use in conjunction with other compounds where the regions are combined in the same moiety. Of particular interest is the use of building blocks for forming the compounds, where the synthesis is performed in a repetitive manner using the same linking chemistry at a plurality of stages. The subject compounds are linked to binding compounds for identification to provide identifying reagents, where binding of an identifying reagent target in an assay system results in the release of the identifying tag (hereinafter referred to as an, "eTag™ reporter") where the eTag reporters can be differentiated. Large numbers of eTag reporters can be provided in kits comprising a linking functionality for bonding to the binding compounds or kits of building blocks can be provided for synthesizing eTag reporters in situ in conjunction with the synthesis of the binding compound. Of particular interest is the use of the subject eTag reporters in identification of nucleic acids and proteins.

DESCRIPTION OF THE SPECIFIC EMBODIMENTS

Figure 1A:
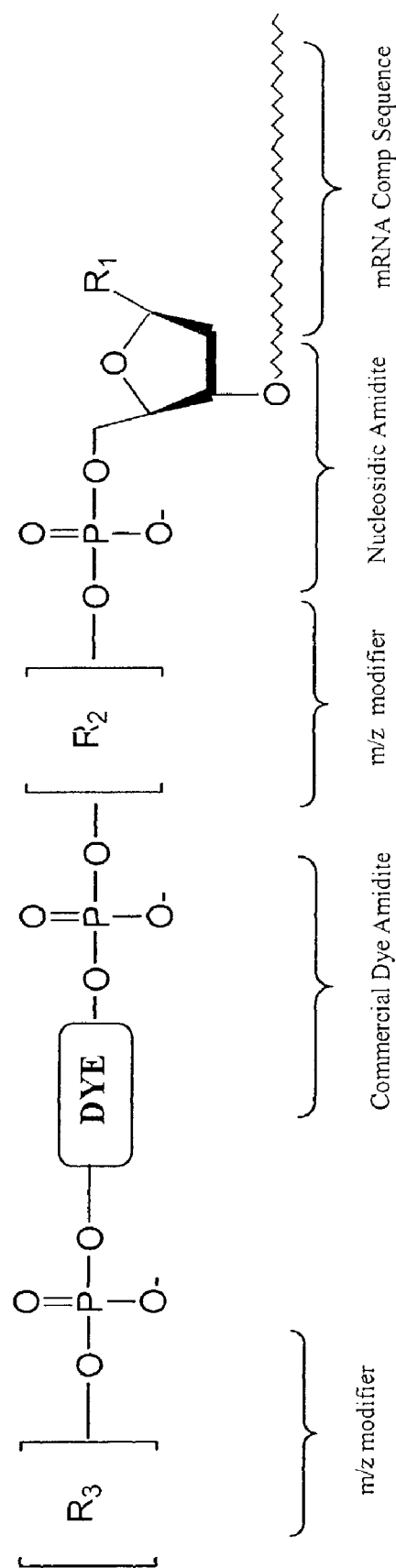
FIG. 1A shows the design and synthesis of eTag reporters on solid phase support using standard phosphoramidite coupling chemistry.

Methods and compounds are provided for multiplexed determinations, where the compounds can be linked to binding compounds for detection of reciprocal binding compounds in a sample. The methods are distinguished by having a plurality of binding events in a single vessel using a mixture of differentially eTag reporter conjugated binding compounds, the release of identifying eTag reporter of those binding compounds bound to their target compounds in the same vessel, and the detection of the released identifying tags by separation of the tags in a single run. The eTag reporter are distinguished by having one or more physical characteristics that allow them to be separated and detected.

The method employs a mixture of binding compounds bound to eTag reporters, where each eTag reporter has a characteristic that allows it to be uniquely detected in a single separation run. The method involves combining the eTag reporter conjugated binding compound with a sample to determine the presence of a plurality of targets under conditions where the binding compounds bind to any reciprocal binding partners to form a binding complex. After sufficient time for binding to occur, the eTag reporters can be released from binding complexes in the same vessel. Various techniques are employed depending upon the nature of the binding compounds for releasing the eTag reporters bound to the complex. The released eTag reporters are then separated and identified by their differentiable characteristics free of interference from the eTag reporters still bound to the binding compound. The techniques for differentiating between eTag reporters bound to a complex and not bound to a complex, include enzymatic reactions that require the complex to exist for cleavage to occur, modification by using ligand/receptor binding, where the ligand is part of the binding compound, so that after cleavage, eTag reporter still bound to the binding compound is modified, dual binding to the target resulting in release of the eTag reporter, where optionally eTag reporter bound to the binding compound is modified, and the like.

One set of eTag reporter are distinguished by differences, which include mass as a characteristic. These eTag reporters do not rely on differentiation based on oligonucleotides of 2 or more, usually 3 or more nucleotides, but rather on organic chemical building blocks that are conveniently combined together to provide for large numbers of differentiable compounds. Therefore, while the original eTag reporter or eTag reporter conjugated to the binding compound can have 2 or more nucleotides, when released from the binding compound, the released eTag reporter will have not more than 3, usually not more than 2 nucleotides. Of particular interest are eTag reporter that are characterized by differences in their mass/charge ratio. These compounds are distinguished by having differences in mobility and are characterized by having regions, which serve as (1) a cleavable linking region; (2) a mass-modifying region; (3) a charge-modifying region: and (4) a detectable region, where the regions may be separate and distinct or combined, there being at least two distinct regions that provide for the differentiation. These eTag reporters may be combined in kits and assays with compounds having all of the regions within a single region to further expand the number of different compounds used as eTag reporters in a multiplexed determination. These compounds find use with other compounds where the different regions are present in the same moiety, for example one to two regions, where the charge-modifying region may also be the detectable region or the mass-modifying region. By having a plurality of compounds that can serve as identifying molecules, mixtures of target compounds can be assayed in a single vessel. By using protocols that result in the release of eTag™ reporters from the binding compound that are identifiable due to differences in mobility, the analysis is greatly simplified, since the eTag reporters will be substantially free of interfering materials and their differences in mobility will allow for accurate detection and quantitation.

The eTag reporters will vary depending upon the method of detection. Groups of at least 10 eTag reporters bound to 10 different binding compounds will be used in the determinations. The eTag reporters will be characterized by being cleavable from the binding compound in the same vessel by the same cleavage mechanism, having a shared characteristic that permits separation and individual detection, being compatible with the determination method and being in the molecular weight range of about 30 to 3000 dal, usually in the molecular weight range of about 35 to 1500 dal. The variation may be mass using a mass spectrometer, where a magnetic field is used for separation, mass/charge ratio using electrokinesis, where an electric field is used for separation, which may also include sieving and/or adsorbing polymers, adsorption, using chromatography, e.g gas chromatography, high pressure liquid chromatography, where polar and van der Waal interactions are used for separation, etc.

For those eTag reporters that rely on mass as a characteristic, the mass unit difference in each eTag reporter when using mass spectrometry for analysis need only be one, preferably at least about 2. For electrophoresis, one will usually have at least a 3, usually 5 unit difference as to the mass/charge ratio, preferably at least about 7, and if one wishes to use shorter distances for separation, 10 or more. These unit differences are intended for molecules of similar structure, for as will be discussed subsequently, structures can affect the mobility without changing the mass/charge ratio.

For the most part, the eTag reporters that have independent regions will have the following formula:

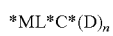

wherein:

L is a terminal linking region;

M is the mass-modifying region;

C is the charge-modifying region;

D is the detectable region, being present when the eTag reporter is detected using spectrophotometric measurement and is not present when the eTag reporter is detected using mass spectrometric measurement;

n is 0 or 1, being 1 for spectrophotometric measurement and 0 for mass spectrometric measurement; and the * intends that M, C and D can be bonded to any of the other groups at any site, and when not independent and distinct regions, any of M, C and D may be merged together to provide multiple functions in a single region and the regions may be bonded directly to each other or interspersed with linking groups or regions. That is, parts of one region may be separated by the whole or parts of another region. Also, as indicated earlier, the different regions will be free of regions comprising oligonucleotides of 3 or more nucleotides, usually free of regions comprising oligonucleotides of 2 or more nucleotides.

Where the eTag reporter is bound to the binding compound, the eTag reporter will have the following formula:

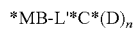
  \*MB-L'\*C\*(D)$_n$ wherein:

B is the binding compound bonded to L';

L' is a modified linking group as a result of the bonding to B; and the remaining symbols are as defined previously.

The released eTag reporters will have the following formula:

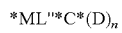
  \*ML"\*C\*(D)$_n$ wherein:

L" is the residue of the linking region, which may include more or less than the original linking group, by including a portion of the binding compound or retaining only a portion of the linking region, by cleaving at other than the bond made by joining the linking region and the binding compound; and the remaining symbols are as defined previously.

Each of the regions may be joined in a variety of ways using different functionalities and synthetic protocols, where the manner of linking may serve as one of the regions, for example, having phosphate links that result in negatively charged links.

The linking region functions as the link between the remainder of the eTag reporter and the binding compound. L has three aspects: a reactive functionality, either inherently or made so by reacting with an activating moiety; a cleavable linkage, which may be the linkage formed by joining to the binding compound, and a group(s) for joining to one or more of the other regions. For bonding to the binding compound, different reactive functionalities may be used, depending upon the nature of the binding compound.

Where the binding compound is an oligonucleotide, that is DNA, RNA, combinations thereof and analogs thereof, e.g. thio analogs, groups that react with alcohols will ordinarily be used. Reactive groups include phosphoramidites, e.g. dialkyl phosphoramidites, wherein alkyl is of from 1-6 carbon atoms; alkyl, cyanoethyl phosphoramidites, wherein alkyl is of from 1-6 carbon atoms, etc.; trialkyl phosphites or phosphates, where alkyl is of from 1-6 carbon atoms; carboxylic acids or derivatives thereof, such as acyl halides, anhydrides and active esters, e.g. dinitrophenyl ester; active halides, such as α-halomethyloxo- and non-oxo, where the halo will be of atomic number 17-53, chloro, bromo and iodo; and the like. The products will be esters, both inorganic and organic acid esters, and ethers. Alternatively, in some cases, one may use other than phosphate derivatives as the linking unit, using amino acids instead, such as glycine and substituted glycines. In this instance, the units of the eTag reporter would use analogous chemistry to synthesize the eTag reporter in situ. The exemplary linkers are only illustrative and not intended to be exhaustive.

For the most part for oligonucleotides, cleavage will be at a phosphate bond between two nucleosides cleaved by an enzyme having nuclease activity e.g. 5'-3' nuclease activity. Therefore, the linking region will usually include a phosphoric acid derivative for coupling to the terminal hydroxy of an oligonucleotide having an appropriate base, such as adenine, cytosine, guanosine, thymidine and uracil. As will be discussed subsequently other available hydroxyl groups of the sugar, ribose or deoxyribose, may be substituted with one of the other regions. Where other methods than nuclease activity are used for release of the eTag reporter, then any of the other functionalities may be used for linking to the oligonucleotide. The linking region will then include a functional entity that allows for specific cleavage.

One need not use oligonucleotides for detection of specific nucleic acid sequences. By employing binding compounds that recognize a particular sequence, either as ssDNA or dsDNA, one may attach a different eTag reporter to each of the different binding compounds. Combining the nucleic acid sample with the eTag reporter labeled binding compounds results in the binding of the binding compounds to sequences that are present in the sample. Various protocols can be used depending on the nature of the binding compound. For example, oligomers of heterocyclic compounds, particularly azole compounds, e.g. pyrrole, imidazole, hydroxyimidazole, joined by two atom chains, particularly having —NH— groups, and amino acids, e.g. glycine, alanine, β-alanine, γ-aminobutyric acid, etc. are employed. The azoles are normally connected by a two atom bridge containing an —NH— group, desirably from the 2 to the 4 or 5 position. These compounds form hairpins that bind in the minor groove of dsDNA with high affinity and specificity for the sequence. See, for example, U.S. Pat. Nos. 6,090,947 and 5,998,140, which are specifically incorporated by reference herein for the disclosure of binding sequences.

By adding the appropriate oligomers to a dsDNA sample, which may include intact or fragmented dsDNA, sequestering the bound oligomers from unbound oligomers and releasing the eTag reporters bound to the dsDNA, one can rapidly determine the presence of dsDNA sequences in the sample. Sequestering can be achieved with proteins that bind dsDNA, by having ligands bound to the dsDNA, e.g. using PCR with primers carrying a ligand, etc. Alternatively, by having a biotin or other ligand bonded to the eTag reporter conjugated to the binding compound that is retained with the binding compound on release of the eTag reporter, one can add the ligand receptor having a charge opposite to the released eTag reporter, so that in electrophoresis the eTag reporter would migrate in the opposite direction. The methods can find particular use where the sensitivity of the system is adequate to avoid amplification and directly determine the presence of a sequence without denaturation. This approach can find use with detecting infectious organisms, e.g. bacteria, viruses and protista, identifying specific chiasmas, identifying genomes, and the like.

There are a large number of different functional entities that are stable under the conditions used for the binding event with the binding compound and may then be cleaved without affecting adversely the eTag reporter. Functional entities may be cleaved by chemical or physical methods, involving oxidation, reduction, solvolysis, e.g. hydrolysis, photolysis, thermolysis, electrolysis, chemical substitution, etc. Specific functional entities include thio ethers that may be cleaved with singlet oxygen, disulfide that may be cleaved with a thiol, diketones that may be cleaved by permanganate or osmium tetroxide, β-sulfones, tetralkylammonium, trialkylsulfonium, tetralkylphosphonium, etc., where the α-carbon is activated with carbonyl, nitro, etc., that may be cleaved with base, quinones where elimination occurs with reduction, substituted benzyl ethers that can be cleaved photolytically, carbonates that can be cleaved thermally, metal chelates, where the ligands can be displaced with a higher affinity ligand, as well as many other functional entities that are known in the literature. Cleavage protocols are described in U.S. Pat. Nos. 5,789,172, 6,001,579, and references cited therein.

The eTag reporters find use in determinations involving a plurality of target entities. Usually, one will be interested in at least about 3 target entities, more usually at least 5, frequently at least about 10 or more, and may be interested in at least about 20 or more, even about 100 or more. The number of eTag reporters will usually be equal to the number of target entities, although in some situations, the same eTag reporter may be used to identify a plurality of related target entities and one may then deconvolute the results as to individual target entities. The eTag reporters bound to the binding members can be added individually or in combination to the sample and then processed to determine the presence of the target entities.

Of interest is to have two eTag reporters that are closely similar in mobility, usually closer in mobility to each other than to unrelated eTag reporters. Where there are paired situations to be analyzed, such as alleles, MHC antigens, single nucleotide polymorphisms, etc., by having the eTag reporters in proximity in the electropherogram, particularly where they have distinguishable detectable regions, e.g. fluorescers fluorescing at different wavelengths, one obtains a quick determination if none, one or both of the pairs are present in the sample.

Genetic analyses may take many forms and involve determinations of different information. Genetic analyses are involved with sequencing, detection of specific sequences as related to the presence of specific genes or regulatory sequences, identification of organisms, identification of transcription events as related to different cells, different cell stages and external stimuli, identification of single nucleotide polymorphisms, alleles, repetitive sequences, plastid DNA, mitochondrial DNA, etc., forensic medicine, and the like. In each case one has a complex sample to be assayed, where one is interested in numerous binding events. By providing for a unique eTag reporter for each event, one can perform simultaneously a number of assays in the same flask and with a single sample or a few aliquots of the sample. For example, where an assay involves a single nucleotide in each vessel, one would use four vessels, one for each nucleotide. In most cases, the eTag reporters can be separated from other components of the assay mixture to substantially reduce interference from these other components when assaying for the eTag reporters.

There are a number of genetic analyses that involve cleavage of a phosphate bond of a nucleic acid sequence as a result of hybridization. For the most part, the initial step will be in solution, although one may have one or more reagents bound to a solid support in the first and succeeding stages of the determination. One technique is described in U.S. Pat. Nos. 5,876,930 and 5,723,591, where a primer and a probe are bound to a target sequence and by extending the primer with a DNA polymerase having 5'-3' nuclease activity, the terminal nucleotides are cleaved as the polymerase processes along the target DNA. By having an eTag reporter bonded to the terminal and/or internal nucleotide(s), the eTag reporter will be released when the target nucleic acid is present. Another technique employs an enzyme referred to as a cleavase, which recognizes a three member complex of the target nucleic acid, a primer and a probe. See, U.S. Pat. No. 5,719,028. Attached to the terminus of the probe is an eTag reporter that is released by the cleavase, where the three membered complex is formed.

For detecting single nucleotide polymorphisms ("snps"), various techniques can be employed of varying complexity. In one technique, a primer is employed that terminates at the nucleotide immediately preceding the snp. One can have the eTag reporter bound to the primer and a ligand bound to the nucleotide reciprocal to the snp. One can either have 4 vessels, each with a different labeled nucleotide or one vessel with each of the labeled nucleotides having a different label. Various polymerases having 3'-5' editing can be used to ensure that mismatches are rare. The extended primers may then be captured, for example, by having a ligand, e.g. biotin, and contacting the extension mixture with the reciprocal receptor, e.g. streptavidin, bound to a support and the eTag reporter released and analyzed. By grouping targets of interest having the same nucleotide for the snp, the assay may be multiplexed for a plurality of targets. Other techniques include having probes where the snp is mismatched. The mismatching nucleotide is labeled with the eTag reporter. When the snp is present, the eTag reporter labeled nucleotide will be released for detection. See U.S. Pat. No. 5,811,239.

In another variation, one may ligate a primer and a probe, where one is 3' of the other when hybridized to a target nucleic acid. By having one of the pair of primer and probe with an eTag reporter with a cleavable linkage and the other of the pair with an agent capable of causing cleavage of the cleavable linkage in conjunction with another agent, the primer and probe may be ligated together when bound to the target. One can release the ligated pair from the target, e.g. heat, and recycle by cooling the mixture to allow for hybridization of the primer and probe, ligating primer and probe bound to target and then denaturing to release the ligated primer and probe, amplifying the number of ligated primers and probes. Once the desired degree of amplification has been achieved, one may provide the additional reagent resulting in release of the eTag reporters.

Where PCR or other amplification reaction is used involving a primer, the primer can be labeled with a ligand that allows for sequestering of the amplified DNA, one can then sequester the DNA by means of a receptor reciprocal to the ligand, which receptor is bound to a support and add probes labeled with eTag reporters specific for the probe sequence. After hybridization and washing to remove non-specifically bound and unbound nucleic acid, the eTag reporters are released and analyzed.

Instead of nucleic acid assays, one may be interested in protein assays. For determining a mixture of proteins, one may use intact cells, intact viruses, viral infected cells, lysates, plastids, mitochondria or other organelles, fractionated samples, or other aggregation of proteins, by themselves or in conjunction with other compounds. Any source of a mixture of proteins can be used, where there is an interest in identifying a plurality of proteins.

Proteomics has come to the fore, where one is interested in cellular expression during metabolism, mitosis, meiosis, in response to an external stimulus, e.g. drug, virus, change in physical or chemical condition, involving excess or deficient nutrients and cofactors, stress, aging, presence of particular strains of an organism and identifying the organism and strain, multiple drug resistance, and the like. It is necessary to have a means for identifying a large number of proteins in a single sample, as well as providing some quantitation of the different proteins being detected. In one assay one may use binding proteins specific for the target proteins. One group of binding proteins is bound to a support, such as a vessel or channel wall, particles, magnetic or non-magnetic, e.g. latex particles, dextrose, sepharose, cellulose, etc., where the support permits sequestering the target proteins to the support. Most commonly, antibodies, particularly monoclonal antibodies rather than antisera, will be used, although the latter may also find use. In some situations other receptors may find use, such as lectins, enzymes, surface membrane proteins, etc. and in some situations, ligands for the proteins may be employed. The reciprocal-binding members, receptors and ligands, may be bound to the support through covalent or non-covalent bonding. Activated surfaces find use, where the surface has an active functional group that will react with the reciprocal-binding member to provide for stable binding to the surface, e.g. silyl chloride modified glass, cyanogen bromide modified polysaccharides, etc. Proteins bind tightly to some plastic surfaces, so that no covalent bonding is required. Ligands have or can be provided with active functional groups for bonding to the surface. If desired the binding to the surface can be accomplished in two steps by bonding a ligand to the reciprocal binding member and binding a ligand binding member to the support, for example, biotin as the ligand and strept/avidin as the ligand binding member, or one may have anti-Ig bound to the surface to bind to antibodies bound to the target protein. In addition, where a change in environment is localized, one may have a large concentration of a counteracting agent, e.g. a large amount of buffer at pH 7, for example, $\geq 200$ mM phosphate, where ammonia is produced that creates a localized basic environment.

The sample is combined with the reciprocal binding member, which may be bound to the support or subsequently bound to the support. After washing away the other components of the mixture, receptor for the target protein labeled with eTag reporter molecules specific for the particular receptor are added to the bound target protein, so as to become bound to the support through the target protein. One or more eTag reporter molecules will be bound to the receptor, usually not more than about 20, frequently not more than about 10. The number will be limited by the degree of loss of the binding affinity as the number of eTag reporter molecules is increased. Normally, the support bound receptor and the eTag reporter labeled receptor will bind to different epitopes of the target protein, although in some situations where the target has a plurality of the same epitope, the receptors may be specific for the same epitope. After washing away all eTag reporter labeled receptor that is not specifically bound to the target protein(s), the eTag reporter molecules are released and assayed.

Where the target permits binding of two reciprocal binding members or where an additional reagent is provided which permits this event, one can use determinations involving "channeling" or energy transfer. See, for example, U.S. Pat. Nos. 5,843,666 and 5,573,906. There are numerous methodologies involving channeling in the literature, where for the most part, the channeling was involved in producing a directly detectable signal, usually a change in absorption or emission of light. Channeling involves having two reagents, where the first reagent, when in proximity to the second reagent, produces a detectable signal. For the eTag reporter, the detectable signal is the release of the eTag reporter from the binding component. The release will usually be a function of the production of a short-lived entity, such as a chemical species or a photoactivated excited species, but may be the result of changing the local environment as compared to the bulk solution. So far as the chemical species, illustrative species include singlet oxygen, hydrogen peroxide, NADH, and hydroxyl radicals. Two entities are employed that have reciprocal binding members that bind to the same target moiety. One of the entities generates an active species. The other entity has a susceptible functionality that interacts with the active species resulting in release of the eTag reporter or responds to the changed local environment to release the eTag reporter. Either the active species is short lived, so that it will not create significant background because beyond its vicinity, the active species becomes inactive or a scavenger is employed that efficiently scavenges the active species, so that it is not available to react with the susceptible functionality that is not bound to the target.

Generators of reactive species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH. One cleavable link can be based on the oxidation of sulfur or selenium, where a thioether, sulfoxide, or selenium analog thereof, is present at the α- or β-position in relation to an activating group, which makes the hydrogen at to the activating group acidic and capable of being removed by base, so as to release the oxidized functionality to which is attached the eTag reporter or to be subject to oxidation with release of the eTag reporter. Alternatively, one may use metal chelates that are stable at one oxidation state and unstable at another oxidation state. Other compounds include a α-substituted methylquinones, which have an eTag reporter bonded through a leaving group, such as sulfonyl, oxy, amino, etc.

By using a heterogeneous system, a first agent for causing cleavage may be bound to a surface to provide an environment for release of the eTag reporter when bound to the surface. Where a second agent is required to cause the release of the eTag reporter, the second agent is added after sufficient time for the eTag reporter conjugated binding compound to become bound to the surface. Where the target is a nucleic acid, the nucleic acid may be bound to the first agent containing surface by having ssDNA binding proteins bound to the surface or other convenient means known in the art. Once the target is bound to the surface, the eTag reporter conjugated oligonucleotides homologous the target nucleic acid sequences are added, followed by the second agent. With ligands and proteins, one can have receptors, which bind at one site, on the surface and eTag reporter binding compounds that bind at a different site forming what is referred to in the art as a "sandwich."

For singlet oxygen, one may use various sensitizers, such as squarate derivatives. See, for example, Ullman, et al., Proc. Natl. Acad. Sci. USA 91, 5426-5430(1994). Examples of combinations that find use in this invention may be found in U.S. Pat. Nos. 5,536,498; 5,536,834; references cited therein; H. H. Wasserman and R. W. Murray. Singlet Oxygen. Academic Press, New York (1979); A. L. Baumstark, Singlet Oxygen, Vol. 2, CRC Press Inc., Boca Raton, Fla. 1983. Other cleavage mechanisms may be found in WO99/64519; WO99/13108; WO98/01533 and WO97/28275.

Singlet oxygen reacts with a wide variety of double bonds, with cleavage of the double bond to an oxo group with separation of the eTag reporter. Illustrative olefins include vinyl sulfides, vinyl ethers, enamines, imines substituted at the carbon atoms with an α-methine (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 75° C., reaction with acid or base, or photolytically in the absence or presence of a sensitizer. Numerous articles describe a variety of compounds that can be decomposed with singlet oxygen, where the articles are frequently interested in light emission, so that the compounds have more complicated structures than are required for the subject purposes, where only cleavage is required for release of the eTag reporter from the binding compound. Therefore, for the most part, synthetic convenience, stability under the conditions of the linking to the binding compound and conditions of the binding, and efficiency of release will be the primary factors in selecting a particular structure.

Articles of interest which are illustrative of a much larger literature include: Adam and Liu, J. Amer. Chem. Soc. 94, 1206-1209, 1972, Ando, et al., J.C.S. Chem. Comm. 1972, 477-8, Ando, et al., Tetrahedron 29, 1507-13, 1973, Ando, et al., J. Amer. Chem. Soc. 96, 6766-8, 1974, Ando and Migita, ibid 97, 5028-9, 1975, Wasserman and Terao, Tetra. Lett. 21, 1735-38, 1975, Ando and Watanabe, ibid 47, 4127-30, 1975, Zaklika, et al., Photochemistsry and Photobiology 30, 35-44, 1979, and Adam, et al., Tetra. Lett. 36, 7853-4, 1995. See also, U.S. Pat. No. 5,756,726.

The formation of dioxetanes is obtained by the reaction of singlet oxygen with an activated olefin substituted with an eTag reporter at one carbon atom and the binding compound at the other carbon atom of the olefin. See, for example, U.S. Pat. No. 5,807,675. These compounds may be depicted by the following formula:

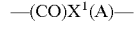
(eTag reporter–W)(X)$_n$C$_\alpha$=C$_\beta$(Y)(Z)

wherein:

W may be a bond, a heteroatom, e.g. O, S, N, P, M (intending a metal that forms a stable covalent bond), or a functionality, such as carbonyl, imino, etc., and may be bonded to X or C$_\alpha$;

at least one X will be aliphatic, aromatic, alicyclic or heterocyclic and bonded to C$_\alpha$ through a hetero atom, e.g. N, O, or S and the other X may be the same or different and may in addition be hydrogen, aliphatic, aromatic, alicyclic or heterocyclic, usually being aromatic or aromatic heterocyclic wherein one X may be taken together with Y to form a ring, usually a heterocyclic ring, with the carbon atoms to which they are attached, generally when other than hydrogen being from about 1 to 20, usually 1 to 12, more usually 1 to 8 carbon atoms and one X will have 0 to 6, usually 0 to 4 heteroatoms, while the other X will have at least one heteroatom and up to 6 heteroatoms, usually 1 to 4 heteroatoms;

Y will come within the definition of X, usually being bonded to C$_\beta$ through a heteroatom and as indicated may be taken together with X to form a heterocyclic ring;

Z will usually be aromatic, including heterocyclic aromatic, of from about 4 to 12, usually 4 to 10 carbon atoms and 0 to 4 heteroatoms, as described above, being bonded directly to C$_\beta$ or through a heteroatom, as described above;

n is 1 or 2, depending upon whether the eTag reporter is bonded to C$_\alpha$ or X;

wherein one of Y and Z will have a functionality for binding to the binding member or be bound to the binding member.

While not depicted in the formula, one may have a plurality of eTag reporters in a single molecule, by having one or more eTag reporters joined to one or both Xs.

Illustrative compounds include S-(eTag reporter)3-thiolacrylic acid, N-(eTag reporter), N-methyl4-amino-4-butenoic acid, O-(eTag reporter), 3-hydroxyacrolein, N-(4-carboxyphenyl)2-(eTag reporter) imidazole, oxazole, and thiazole.

Also of interest are N-alkyl acridinyl derivatives, substituted at the 9 position with a divalent group of the formula:

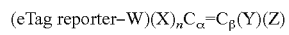
—(CO)X$^1$(A)— wherein:

X$^1$ is a heteroatom selected from the group consisting of O, S, N, and Se, usually one of the first three; and A is a chain of at least 2 carbon atoms and usually not more than 6 carbon atoms substituted with an eTag reporter, where preferably the other valences of A are satisfied by hydrogen, although the chain may be substituted with other groups, such as alkyl, aryl, heterocyclic, etc. groups, A generally being not more than 10 carbon atoms.

Also of interest are heterocyclic compounds, such as diheterocyclopentadienes, as exemplified by substituted imidazoles, thiazoles, oxazoles, etc., where the rings will usually be substituted with at least one aromatic group and in some instances hydrolysis will be necessary to release the eTag reporter.

Also of interest are tellurium (Te) derivatives, where the Te is bonded to an ethylene group having a hydrogen atom β to the Te atom, wherein the ethylene group is part of an alicyclic or heterocyclic ring, that may have an oxo group, preferably fused to an aromatic ring and the other valence of the Te is bonded to the eTag reporter. The rings may be coumarin, benzoxazine, tetralin, etc.

The mass-modifying region, when not including the charge-modifying region or the detectable label, will usually be a neutral organic group, aliphatic, alicyclic, aromatic or heterocyclic, where the heteroatoms will be neutral under the conditions employed for the assay protocol. The heteroatoms may be oxygen as oxy or non-oxo- or oxo-carbonyl, sulfur as thio or thiono, halo, nitrogen as amide, nitro or cyano, phosphorous as phosphite or phosphate triester, etc. Conveniently, the region may be methylene, including polymethyene, alkyleneoxy, including polyalkyleneoxy, particularly alkylene of 2-3 carbon atoms, aryl or substituted aryl, such as phenylene, diphenylene, cyanophenylene, nitrophenylene, thiophenylene, chlorophenylene, furanylene, amino acids, such as N-acyl glycinamide and polyglycinamide, including substituted glycinamides, cyclopentylene, bis-biphenylene-E, where E is carbonyl, oxy, thio, ureido, methylene, isopropylene, and the like; etc. The mass-modifying region will generally be from about 1 to 100, more usually 1 to 60 atoms other than hydrogen, generally having at least one carbon atom and up to 60 carbon atoms and from about 0 to 40 heteroatoms, usually about 0 to 30 heteroatoms.

The charge-modifying region will vary depending upon the other groups present and whether one wishes to reduce the number of unneutralized charges in the molecule or increase the number of unneutralized charges. Charges in the molecule may come from other than the charge-modifying group, such as the label, connecting groups between regions may be included in the charge modifying region, the linking region, and any residue of the binding compound that is retained with the eTag reporter. For the most part, the eTag reporter will have an overall negative charge, although in some instances, there may be an overall positive charge, particularly if positive and negative eTag reporters are to be determined in the same electrophoretic separation. Negative charges can be provided by phosphate, including phosphonate, phosphinate, thiophosphate, etc., borate, carboxylate, sulfonate, enolate, phenoxide, etc. Positive charges can be provided by amines and substituted amines, e.g. ammonium, sulfonium, hydrazine, imine, amidine, metal ions, particularly as chelates and metallocenes, etc. The charge-modifying region may have from 1 to 60 atoms other than hydrogen, usually from about 1 to 30 atoms, where there will be at least one heteroatom, which may be oxygen, nitrogen, sulfur, boron, phosphorous, metal ion, etc.

One may combine the mass-modifying and charge-modifying functions in a single region in a convenient manner using poly(amino acids), where the naturally occurring aspartate and glutamate may serve to provide negative charges, and the naturally occurring lysine, arginine and histidine may serve to provide positive charges. However, one may wish to use unnatural amino acids, such as sulfonic, phosphonic, and boronic acid substituted amino acids. By appropriate choice in conjunction with the other regions, a large number of different mobilities can be achieved. When used in combination with mass-modifying regions, the number of eTag reporters having different mobilities is greatly expanded.

One may use combinations of substituted diols or diamines and dibasic acids, where the substituents are charged, to form diesters and diamides. Illustrative of such oligomers are the combination of diols or diamino, such as 2,3-dihydroxypropionic acid, 2,3-dihydroxysuccinic acid, 2,3-diaminosuccinic acid, 2,4-dihydroxyglutaric acid, etc. The diols or diamino compounds can be linked by dibasic acids, which dibasic acids include the inorganic dibasic acids indicated above, as well as dibasic acids, such as oxalic acid, malonic acid, succinic acid, maleic acid, furmaric acid, carbonic acid, citric acid, tartaric acid, etc. Alternatively, one may link the hydroxyls or amines with alkylene or arylene groups, dicarbonyls, activated dihalo compounds, etc. Other combinations include substituted dithiols, that can be copolymerized with dienes, activated dihalo compounds, etc. Thus, by appropriate selection of the different monomers, low order oligomers can be produced that may then be separated by molecular weight.

The detection region may include any label that can be detected spectrophotometrically and/or electrochemically. A wide variety of labels are available for detection in an electrophoretic device. Commonly used fluorescers include, fluorescein and fluorescein derivatives, lanthanide dyes, rhodamine and rhodamine derivatives, Cy-5, Cy-3, HEX, TET, squarates, and cyanine dyes. The dyes may be charged or uncharged, so as to add or diminish the overall charge of the molecule. Electrochemical labels also find use, such as ferrocene and ruthenium complexes.

For economic and operational reasons, it is generally desirable to use as few lasers for excitation as feasible. Therefore, it will be desirable to use combinations of energy absorbers/transmitters, frequently a fluorescer, and energy receivers/emitters, usually a fluorescer, keeping the energy absorber constant for excitation where energy exchange between the two entities allows for variation in the emission wavelength due to changes in the Stokes shift. Combinations of dyes include fluorescein and HEX, ($ex_{488\ nm}$, $em_{560\ nm}$), and phthalocyanine ($ex_{488\ nm}$, $em_{690\ nm}$). One can provide for various combinations of fluorescers to be bound in proper proximity for energy transfer. A ribosyl group in the linking region or the mass-modifying region provides for one hydroxyl group for linkage of a member of an energy transfer pair and two hydroxyls for insertion into the chain, while deoxyribose substituted with two fluorescers can react with an hydroxyl group as a side chain. The particular unit used to which the members of the energy transfer pair are bonded can be selected to provide mass-modification and/or charge-modification.

The mobility of the eTag reporter will not only depend on the mass/charge ratio according to the formula $(M/z)^{2/3}$, but will also depend on structure. Entities within the eTag reporter that are rigid and extend the molecule enhance the drag and therefore reduce the mobility. Therefore by using rigid groups, such as aromatics, 5- and 6-membered heterocyclics, e.g. tetrahydrofuran, polyenes and polyacetylenes, one can enhance differences in mobility even while the ratio of mass to charge is not significantly different.

Synthesis of eTags comprising nucleotides can be easily and effectively achieved via assembly on a solid phase support during probe synthesis using standard phosphoramidite chemistries. The eTag reporters are assembled at the 5'-end of probes after coupling of a final nucleosidic residue, which becomes part of the eTag reporter during the assay. One may have a nucleotide triphosphate bonded to one of the termini of the building blocks of the eTag reporter. In one approach, the eTag reporter is constructed sequentially from a single or several monomeric phosphoramidite building blocks (one containing a detectable region, e.g. dye), which are chosen to generate eTag reporters with unique electrophoretic mobilities based on their mass to charge ratio. The eTag reporter is thus composed of monomeric units of variable charge to mass ratios bridged by phosphate linkers (FIG. 1A). The separation of eTag reporters, which differ by 9 mass units (Table 1) has been demonstrated. The nucleosidic phosphoramidites employed for eTag reporter synthesis are initially either modified or natural residues. Fluorescein has been the initial dye employed but other dyes can be used as well, as illustrated in FIG. 1A.

Figure 1B:
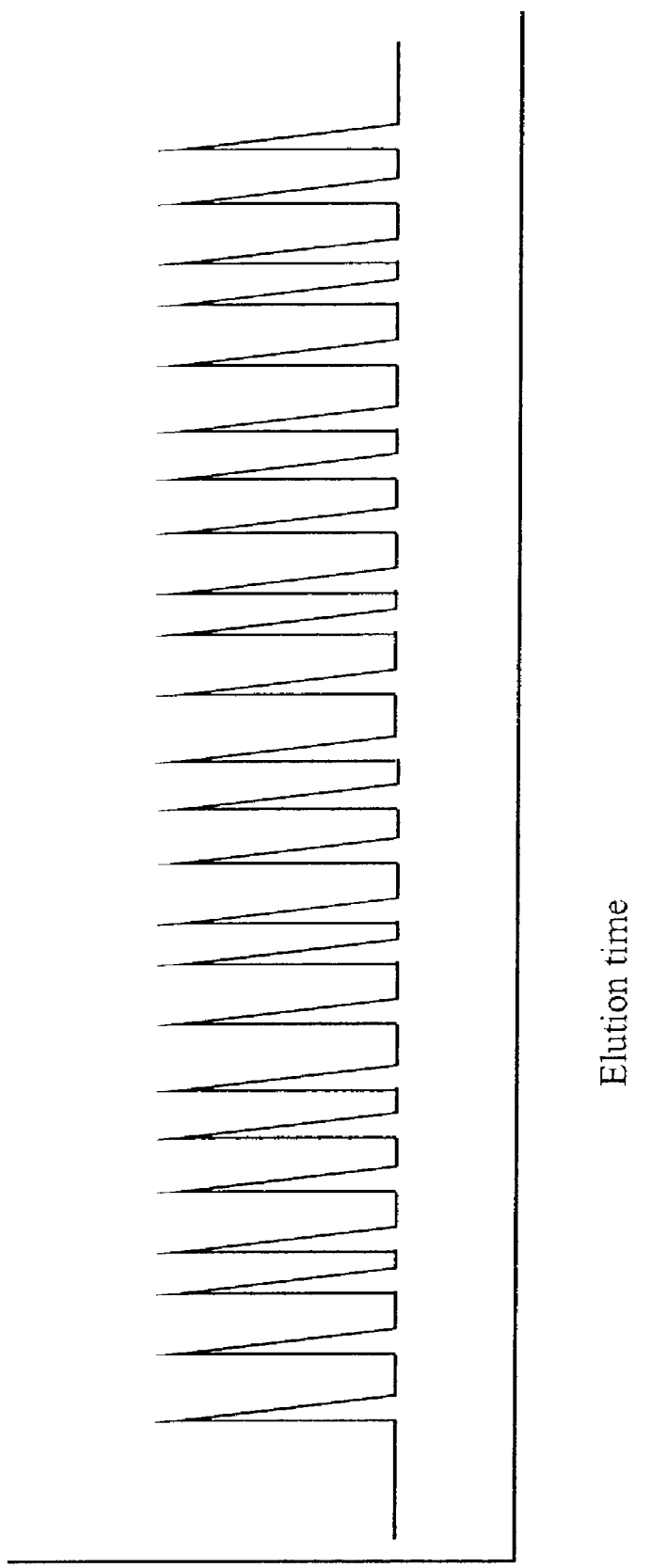
FIG. 1B illustrates separation of eTag reporters designed to possess unique charge to mass ratios.

Some of the combinations of phosphoramidite building blocks with their predicted elution times are presented in Table 2. As shown in Figure B, eTag reporters are synthesized to generate a continuous spectrum of signals, one eluting after another with none of them coeluting (FIG. 1B).

TABLE 1 eTag reporters that have been separated on a LabCard (See experimental section for description.)(detection: 4.7 cm; 200 V/cm).

| E-Tag | Elution Time on CE (sec) | Mass |
|---|---|---|
| [structure: fluorescein-amide-C6-phosphate-deoxythymidine] | 385 | 778 |
| [structure: tetrachlorofluorescein-amide-C6-phosphate-deoxyadenosine] | 428 | 925 |
| [structure: tetrachlorofluorescein-amide-C6-phosphate-deoxycytidine] | 438 | 901 |

TABLE 1-continued
eTag reporters that have been separated on a LabCard (See experimental section for description.)(detection: 4.7 cm; 200 V/cm).
| E-Tag | Elution Time on CE (sec) | Mass |
|---|---|---|
| 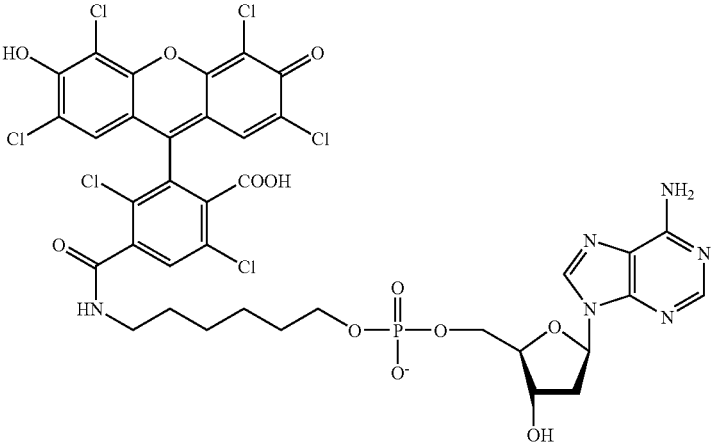 | 462 | 994 |
| 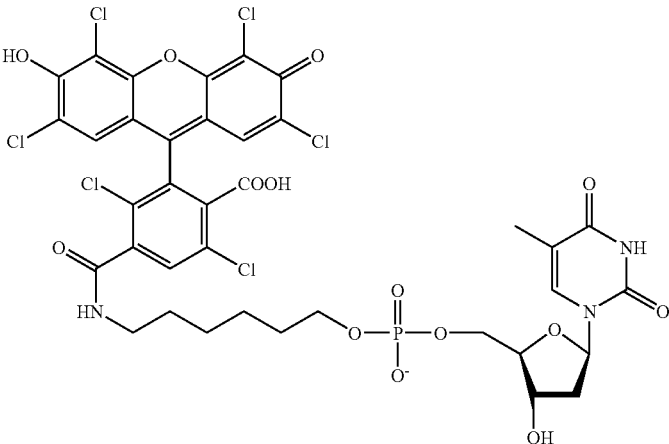 | 480 | 985 |
| 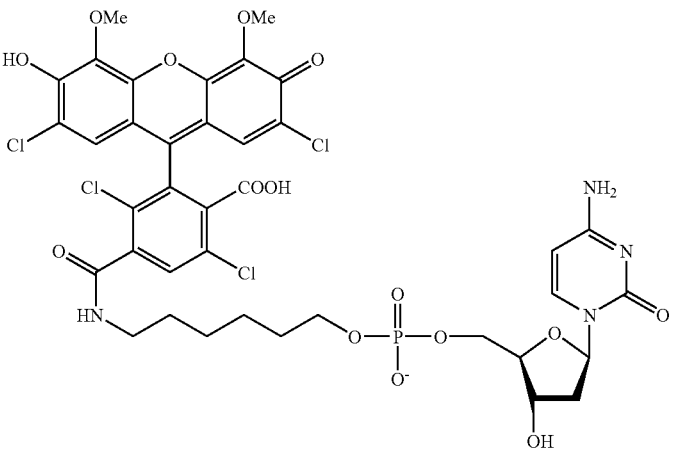 | 555 | 961 |

TABLE 2

Predicted and experimental (*) elution times of eTag reporters. $C_3$, $C_6$, $C_9$, $C_{18}$, are commercially available phosphoramidite spacers from Glen Research, Sterling VA. The units are derivatives of N,N-diisopropyl, O-cyanoethyl phosphoramidite, which is indicated by "Q". $C_3$ is DMT (dimethoxytrityl)oxypropyl Q; $C_6$ is DMToxyhexyl Q; $C_9$ is DMToxy(triethyleneoxy) Q; $C_{12}$ is DMToxydodecyl Q; $C_{18}$ is DMToxy(hexaethyleneoxy) Q.

| Etag | Charge | Elution Time |
|---|---|---|
| Fluorescein–(CH2)5–NH–C(O)–...–O–P(O)(O⁻)–C3C3C3C3C3C3–dC | −9 | 41.12 |
| Fluorescein–(CH2)5–NH–C(O)–...–O–P(O)(O⁻)–C3C3C3C3C3–dC | −8 | 43.72 |
| Fluorescein–(CH2)5–NH–C(O)–...–O–P(O)(O⁻)–O–C6C6C6C6C6C6–dC | −9 | 45.66 |
| Fluorescein–(CH2)5–NH–C(O)–...–O–P(O)(O⁻)–O–C6C6C6C6C6–dC | −8 | 48.14 |
| Fluorescein–(CH2)5–NH–C(O)–...–O–P(O)(O⁻)–O–C6C6C6C6–dC | −7 | 51.21 |
| Fluorescein–(CH2)5–NH–C(O)–...–O–P(O)(O⁻)–O–C3C3C9–dC | −6 | 53.53 |
| Fluorescein–(CH2)5–NH–C(O)–...–O–P(O)(O⁻)–O–C6C6C6–dC | −6 | 55.13 |
| Fluorescein–(CH2)5–NH–C(O)–...–O–P(O)(O⁻)–O–C3C3–dC | −5 | 57.66 |

TABLE 2-continued

Predicted and experimental (*) elution
times of eTag reporters. $C_3$, $C_6$, $C_9$, $C_{18}$, are commercially available
phosphoramidite spacers from Glen Research, Sterling VA. The units are derivatives of
N,N-diisopropyl, O-cyanoethyl phosphoramidite, which is indicated by "Q". $C_3$ is DMT
(dimethoxytrityl)oxypropyl Q; $C_6$ is DMToxyhexyl Q; $C_9$ is DMToxy(triethyleneoxy)
Q; $C_{12}$ is DMToxydodecyl Q; $C_{18}$ is DMToxy(hexaethyleneoxy) Q.

| Etag | Charge | Elution Time |
|---|---|---|
| 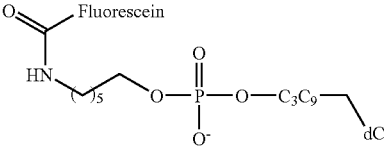 | −5 | 60.00 |
| 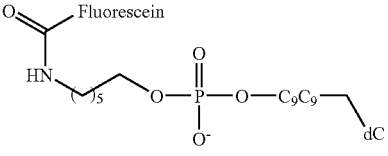 | −5 | 62.86 |
| 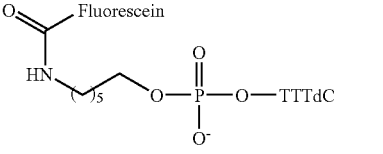 | −6 | 65.00* |
| 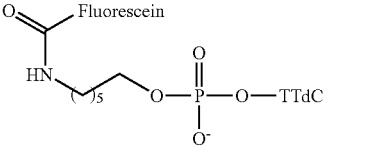 | −5 | 67.50* |
| 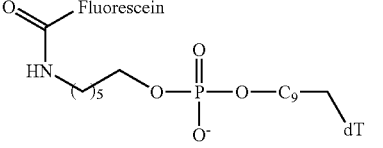 | −4 | 69.61 |
| 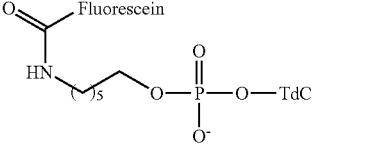 | −4 | 72.00* |

Figure 1C:
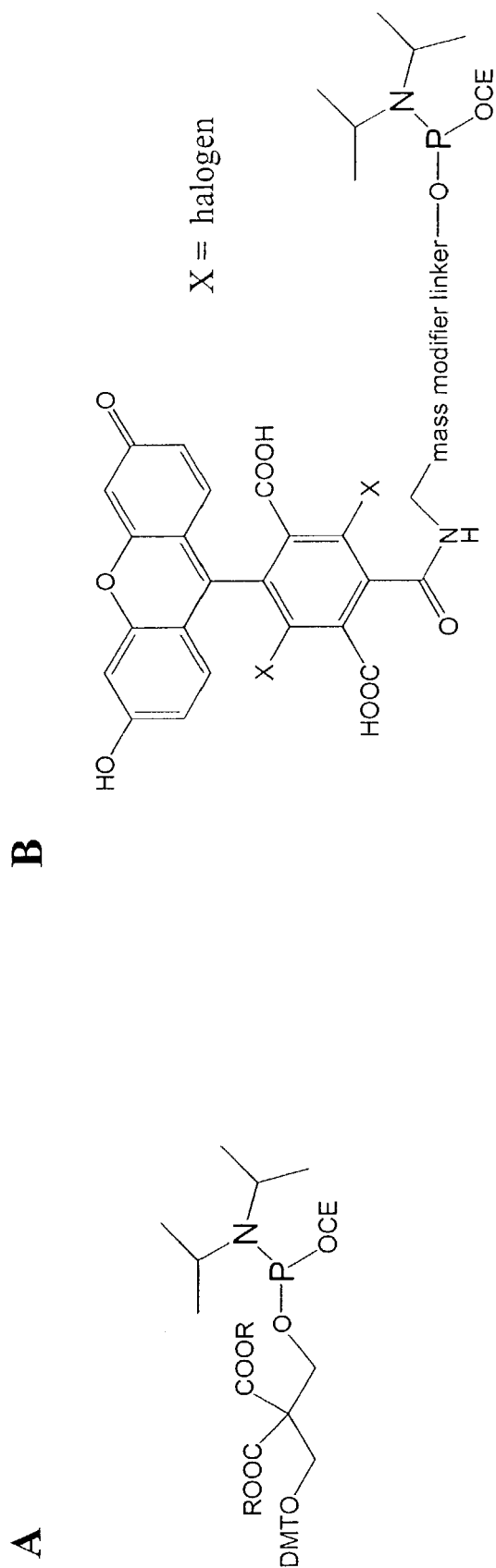
FIG. 1C shows charge modifier phosphoramidites. (EC or CE is cyanoethyl).
Figure 1D:
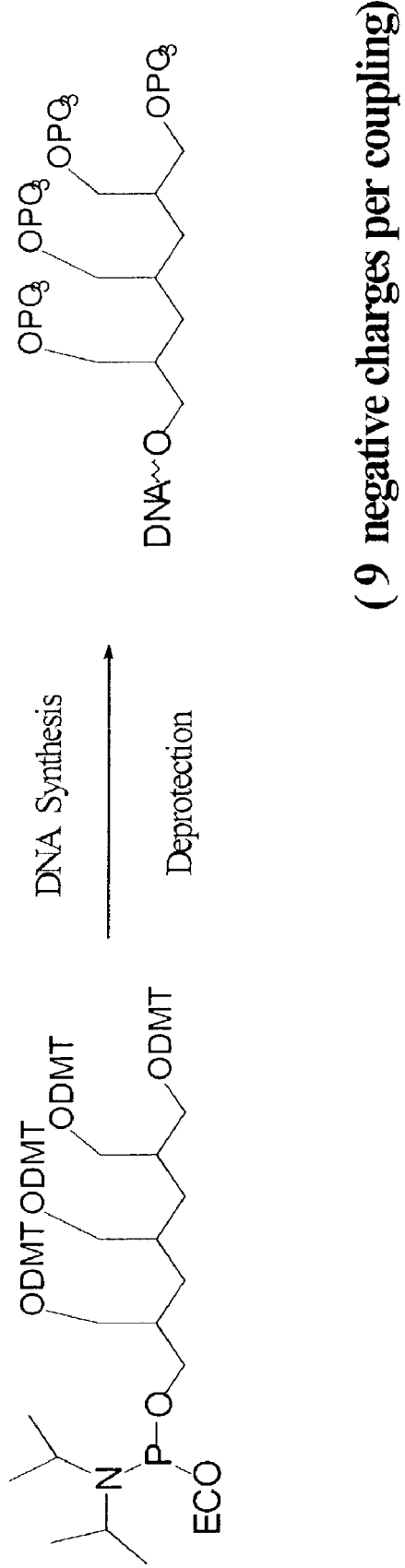
FIG. 1D shows polyhydroxylated charge modifier phosphoramidites.
Figure 2A:
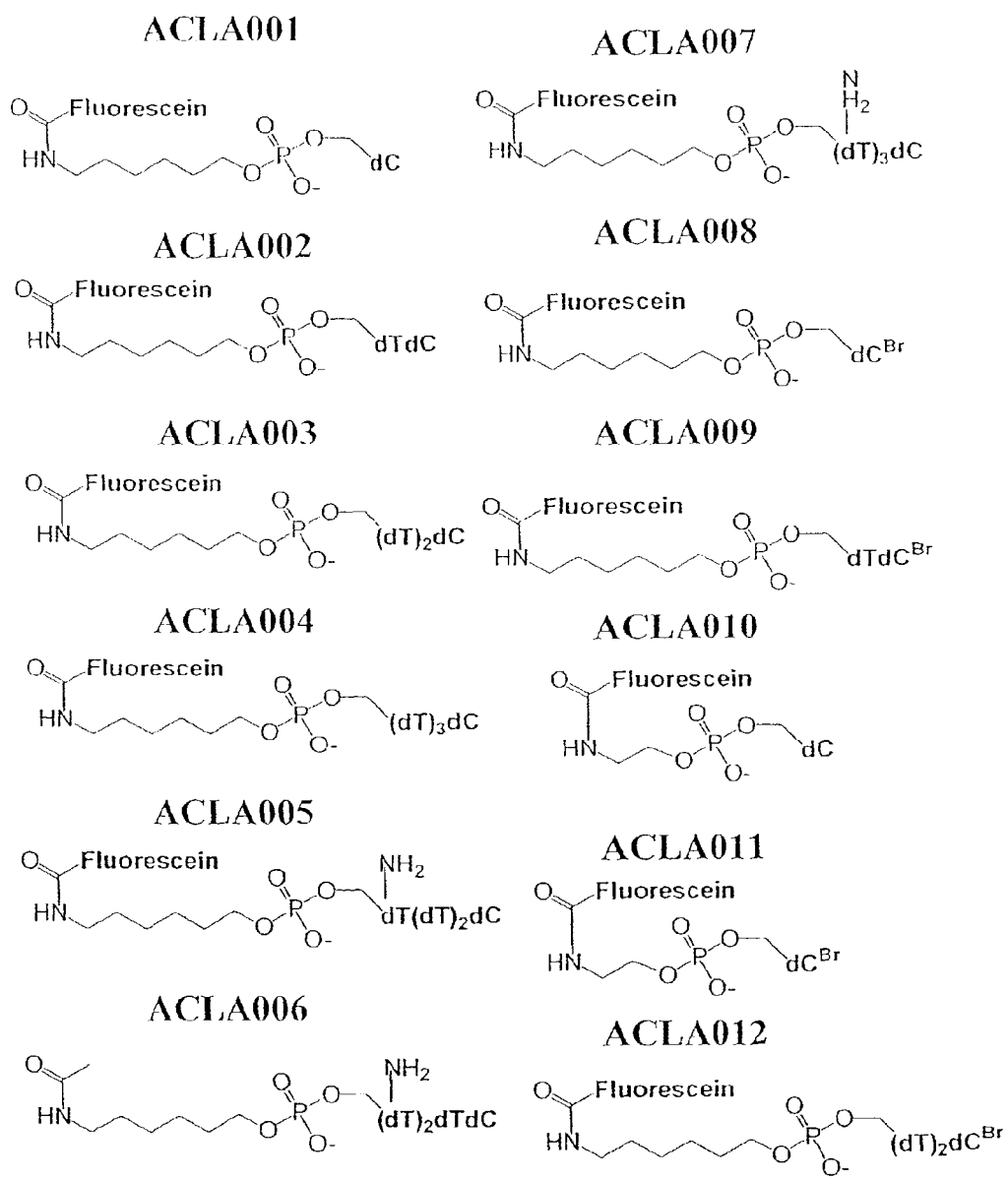
FIGS. 2A-2I show structures of different eTag reporters.
Figure 2B:
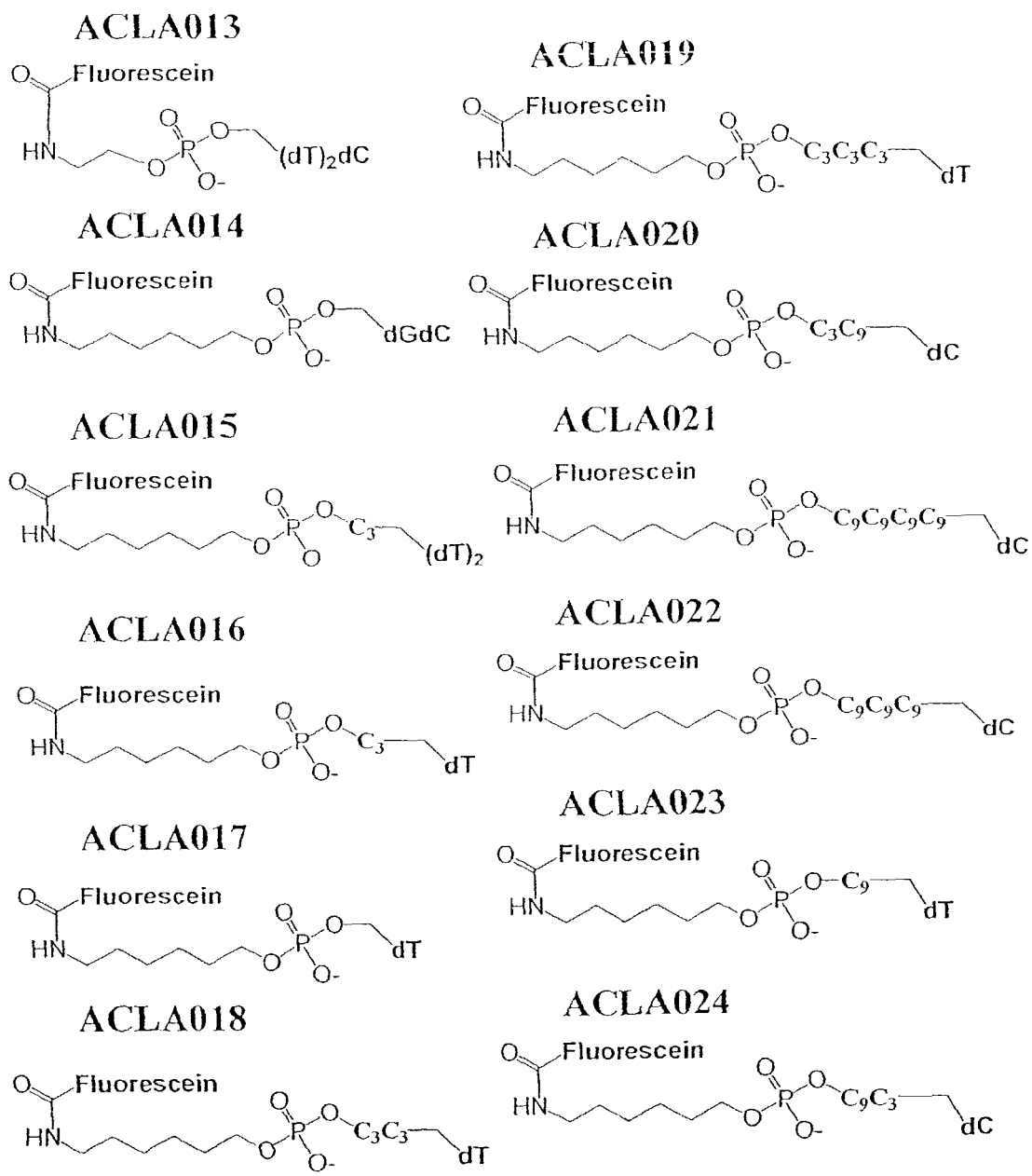
Figure 2C:
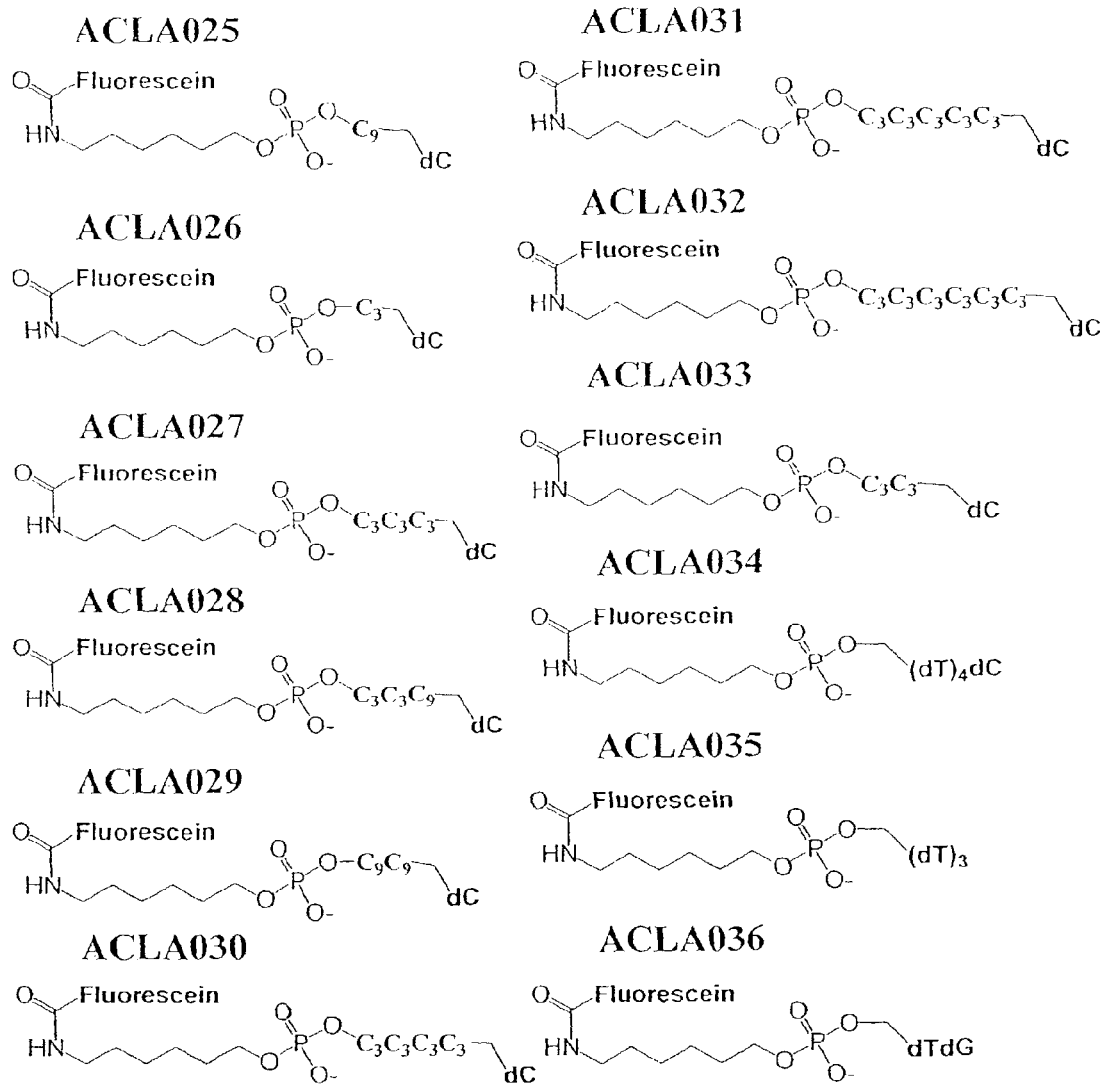
Figure 2D:
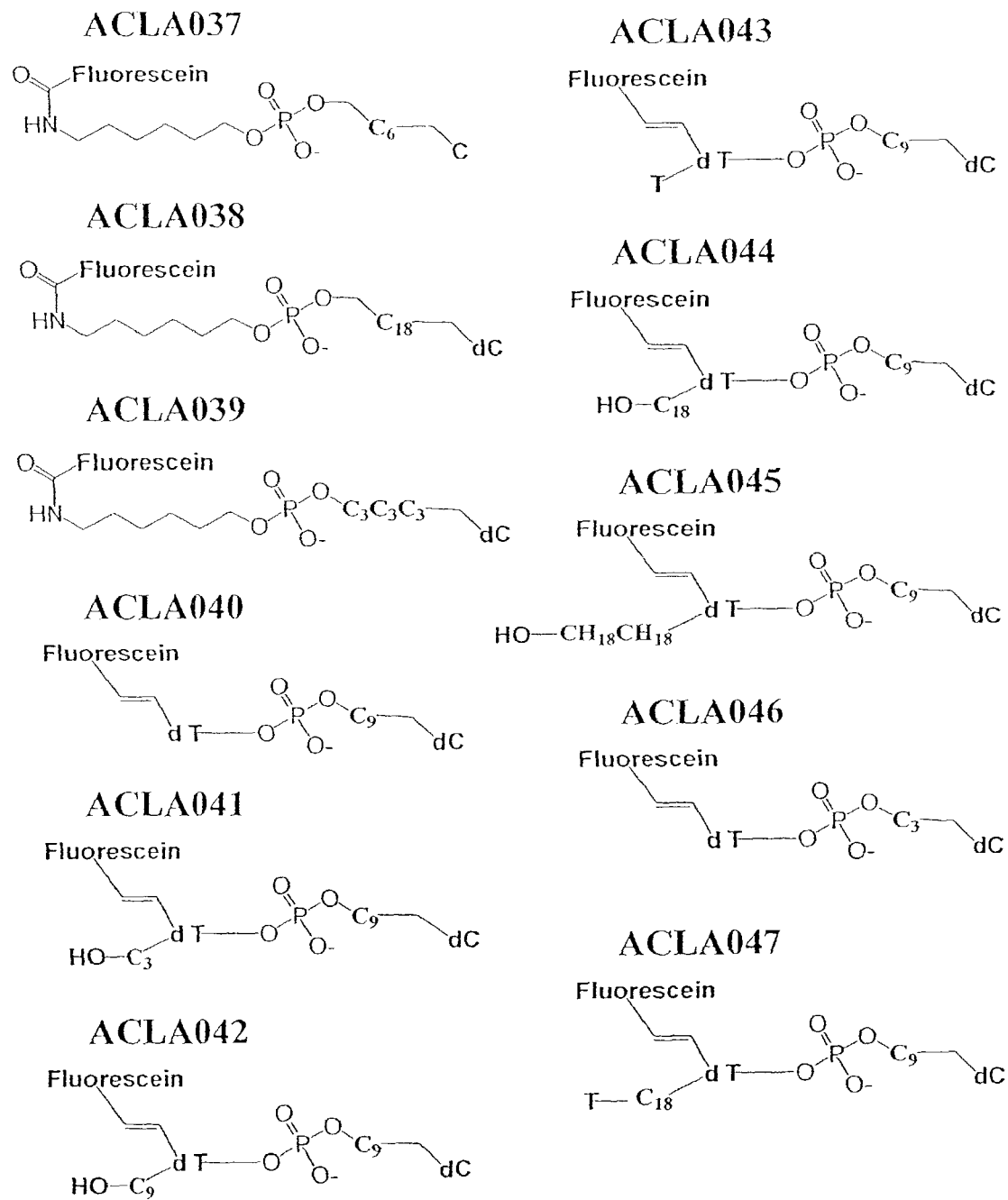
Figure 2E:
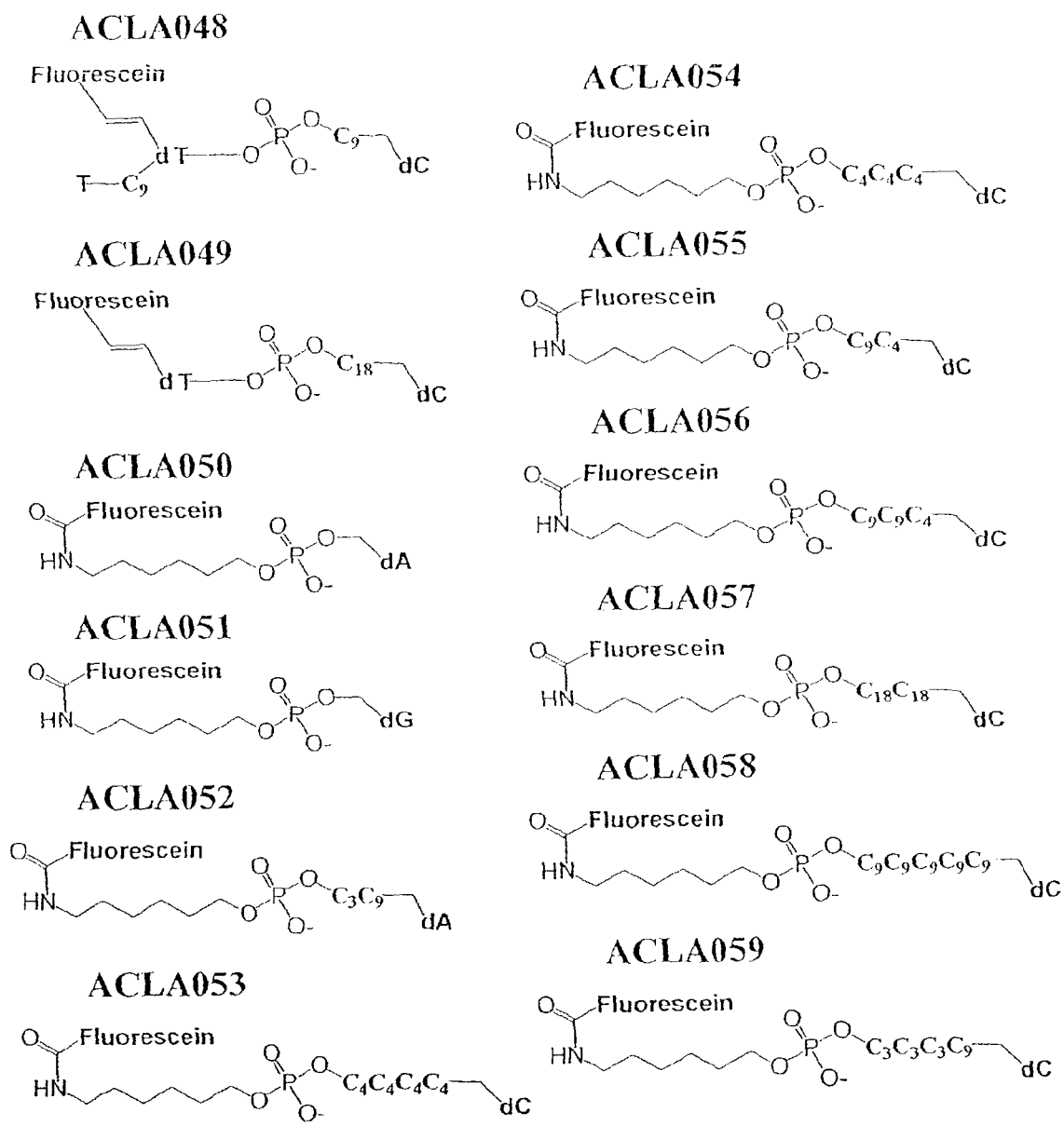
Figure 2F:
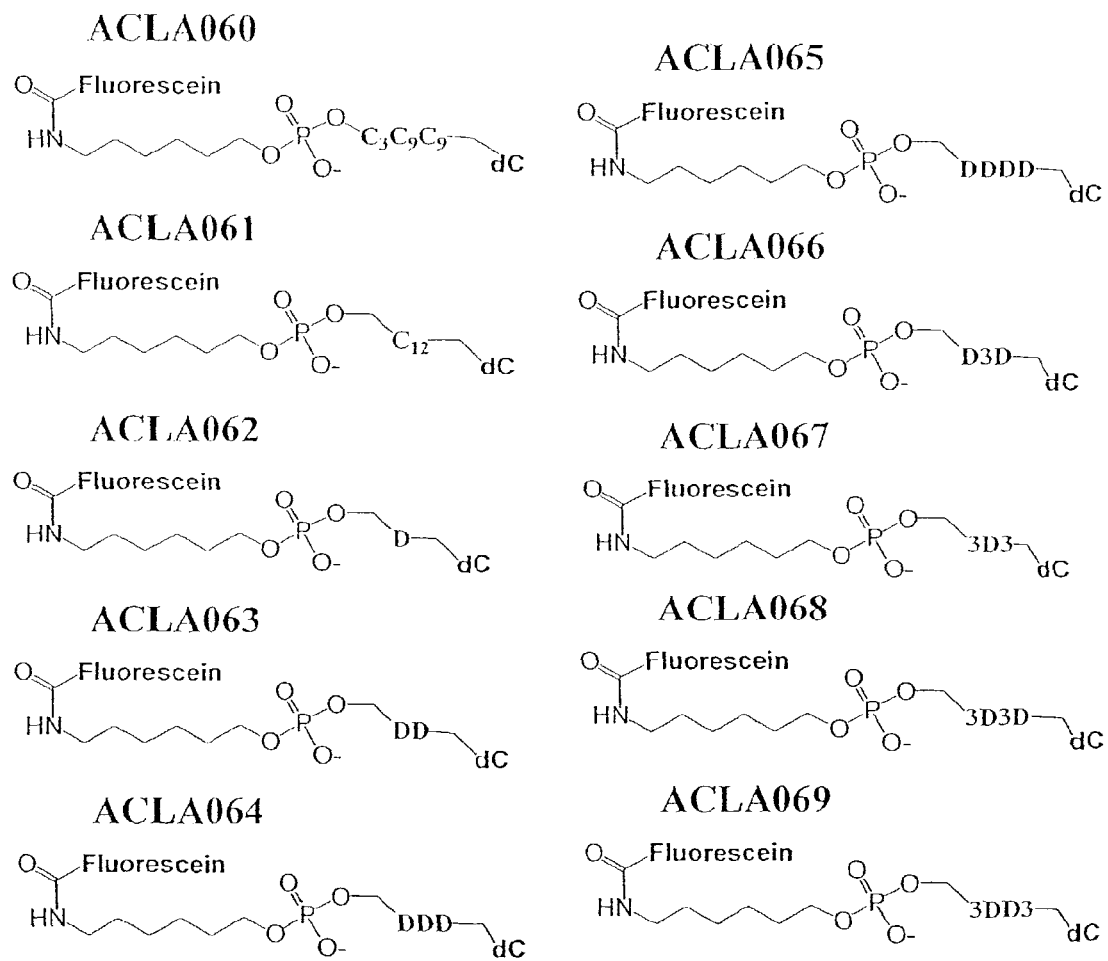
Figure 2G:
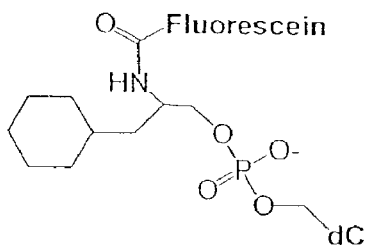
Figure 2G:
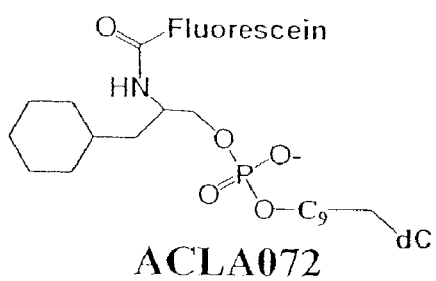
Figure 2G:
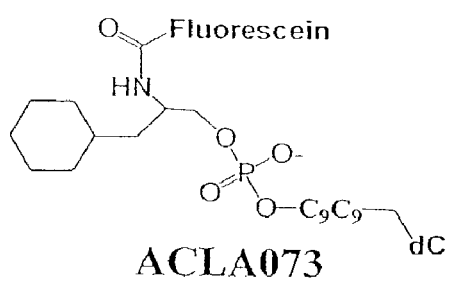
Figure 2G:
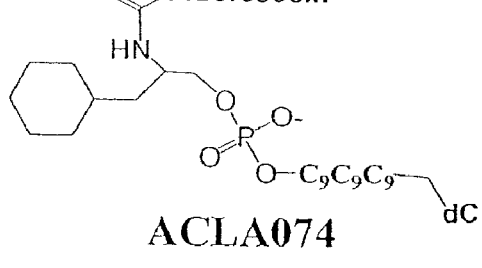
Figure 2G:
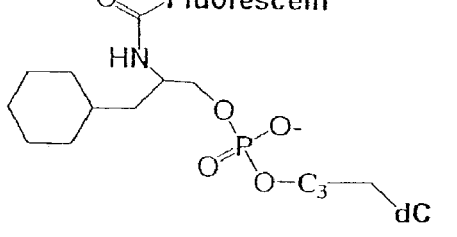
Figure 2G:
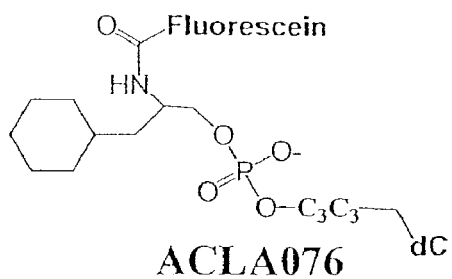
Figure 2G:
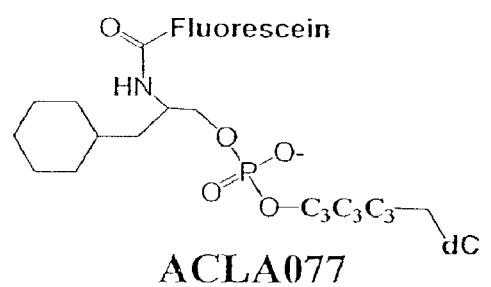
Figure 2G:
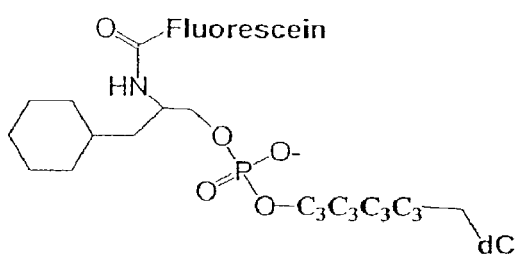
Figure 2G:
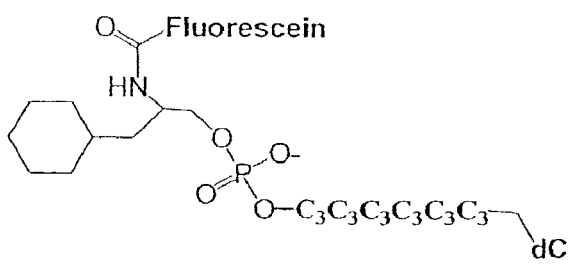
Figure 2H:
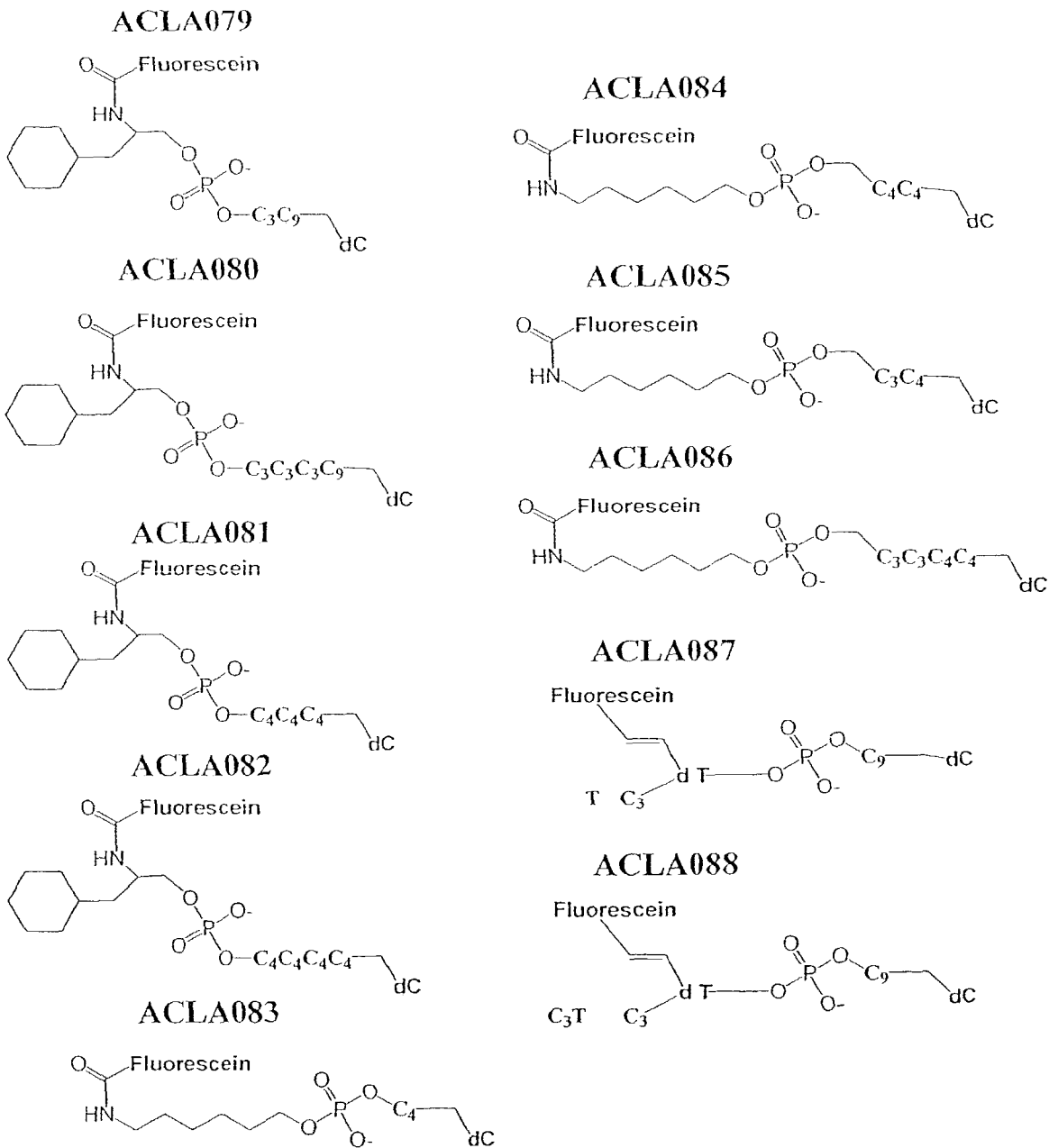
Figure 2I:
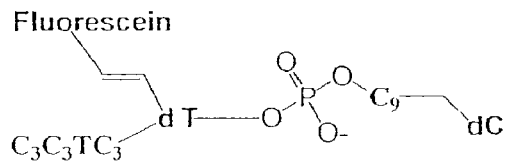
Figure 2I:
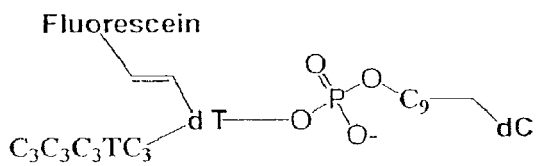
Figure 2I:
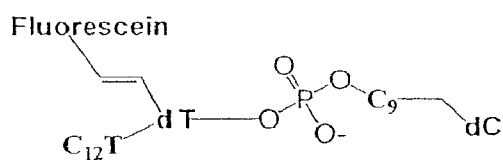
Figure 2I:
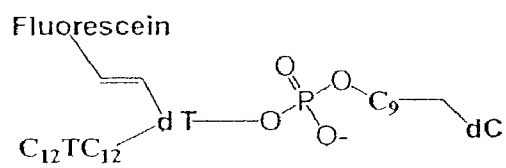
Figure 2I:
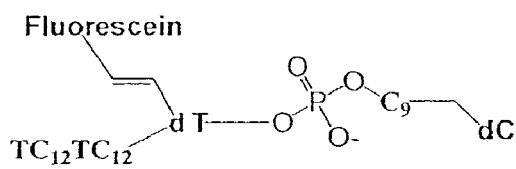
Figure 2I:
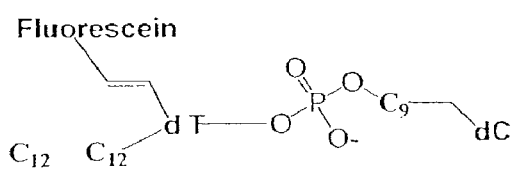
Figure 2I:
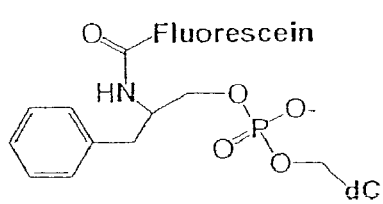
Figure 2I:
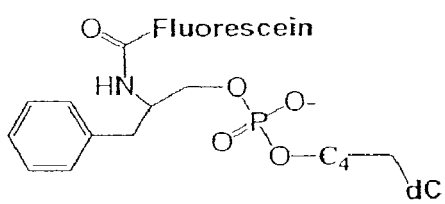
Figure 2I:
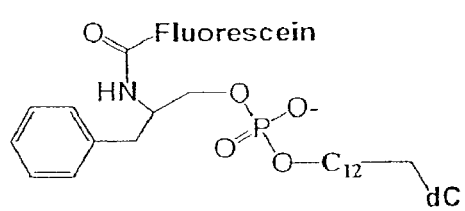

All of the above eTag reporters work well and are easily separable and elute after 40 minutes. To generate eTag reporters that elute faster, highly charged low molecular weight eTag reporters are required. Several types of phosphoramidite monomers allow for the synthesis of highly charged eTag reporters with early elution times. Use of dicarboxylate phosphoramidites (FIG. 1C), allows for the addition of 3 negative charges per coupling of monomer. Polyhydroxylated phosphoramidites (FIG. 1D) in combination with a common phosphorylation reagent enable the synthesis of highly phosphorylated eTag reporters. Combinations of these reagents with other mass modifier linker phosphoramidites allow for the synthesis of eTag reporters with early elution times.

The aforementioned label conjugates with different electrophoretic mobility permit a multiplexed amplification and detection of multiple targets, e.g. nucleic acid targets. The label conjugates are linked to oligonucleotides in a manner similar to that for labels in general, by means of linkages that are enzymatically cleavable. It is, of course, within the purview of the present invention to prepare any number of label conjugates for performing multiplexed determinations. Accordingly, for example, with 40 to 50 different label conjugates separated in a single separation channel and 96 different amplification reactions with 96 separation channels on a single microfluidic chip, one can detect 4000 to 5000 single nucleotide polymorphisms.

Figure 9:
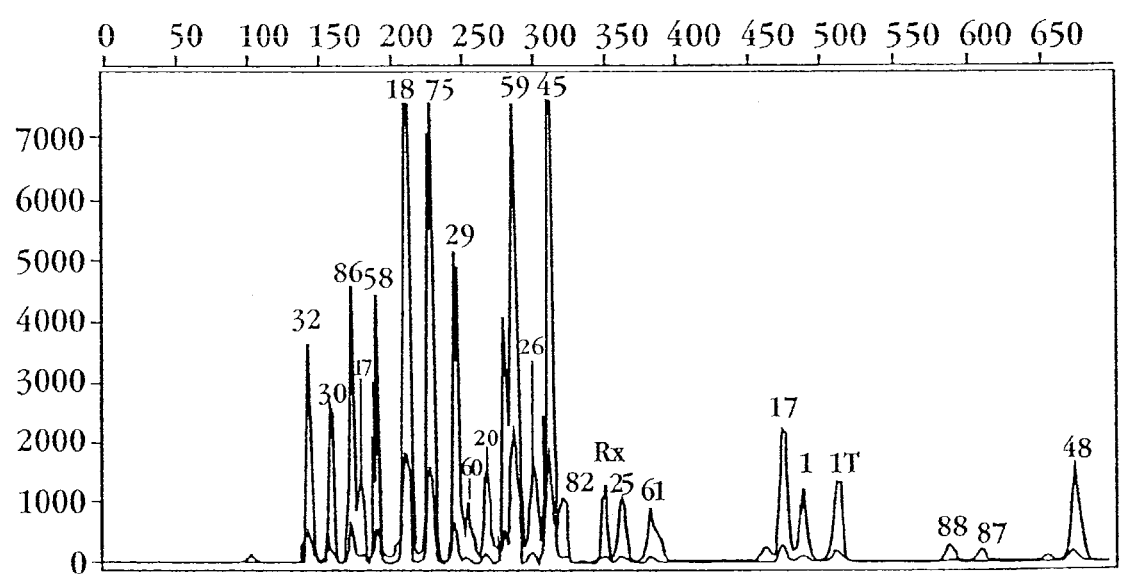
FIG. 9 is multiple electropherograms showing separation of individual eTAG reporters. The figure illustrates obtainable resolution of the reporters which are identified by their ACLA numbers.
Figure 10:
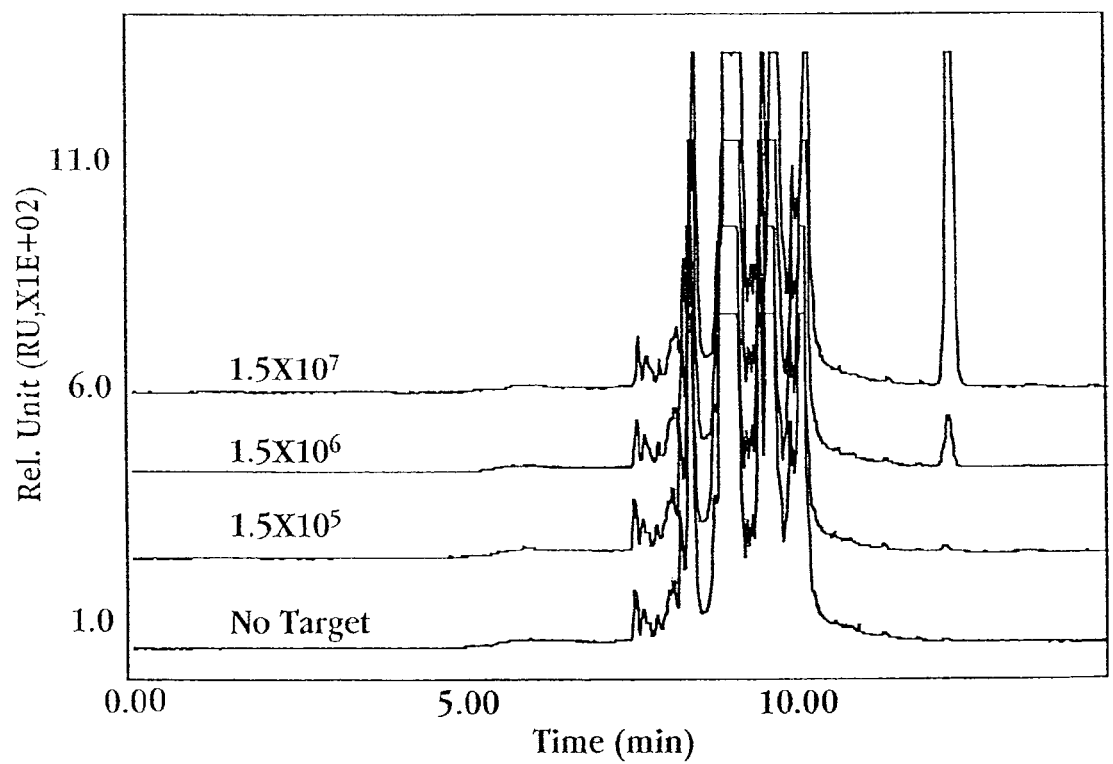
FIG. 10 is multiple electropherograms showing a separation on a 310 analyzer that has occurred after an amplification reaction, in the presence of probe and primer without the addition of avidin.
Figure 11:
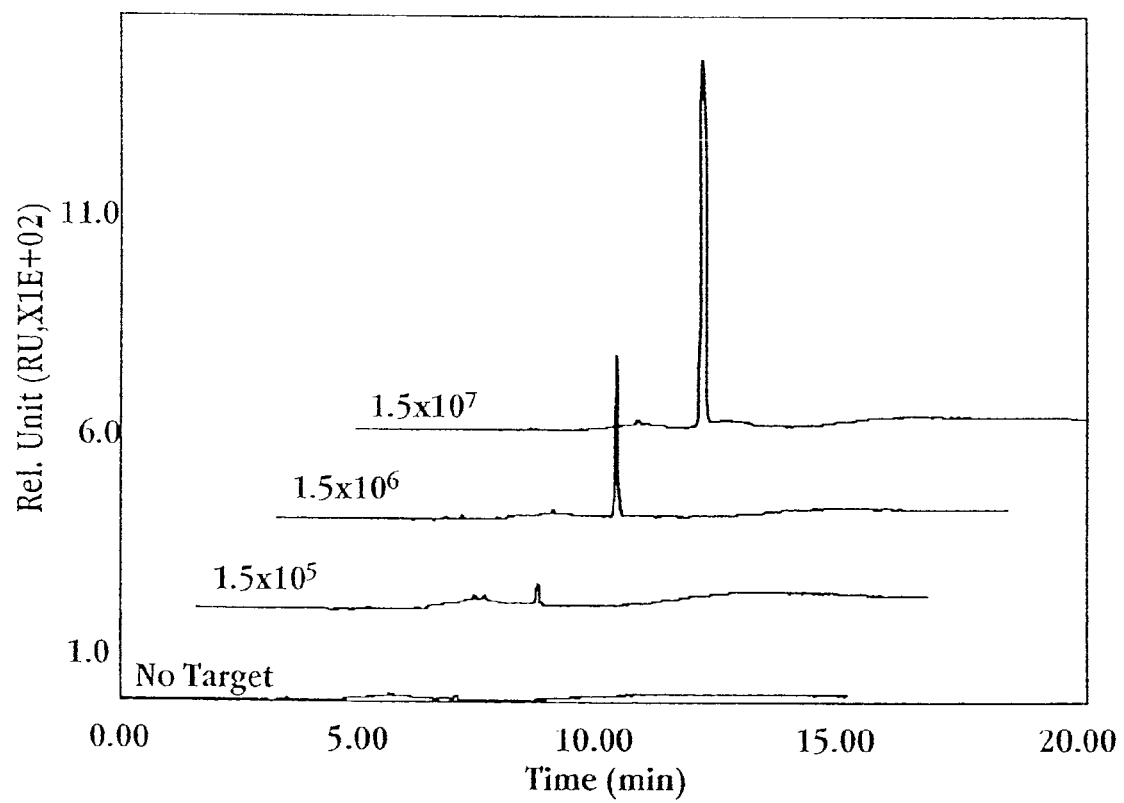
FIG. 11 is multiple electropherograms showing a separation on a 310 analyzer that has occurred after an amplification reaction, in the presence of probe and primer with the addition of avidin.

The separation of eTag reporters, which differ by 9 mass units (Table 1) has been demonstrated as shown in FIG. 9. The penultimate coupling during probe synthesis is initially carried out using commercially available modified (and unmodified) phosphoramidites (Table 2). This residue is able to form hydrogen bonds to its partner in the target strand and is considered a mass modifier but could potentially be a charge modifier as well. The phosphate bridge formed during this coupling is the linkage severed during a 5'-nuclease assay. The final coupling is done using a phosphoramidite analogue of a dye. Fluorescein is conveniently employed, but other dyes can be used as well.

One synthetic approach is outlined in Scheme 1. Starting with commercially available 6-carboxyfluorescein, the phenolic hydroxyl groups are protected using an anhydride. Isobutyric anhydride in pyridine was employed but other variants are equally suitable. It is important to note the significance of choosing an ester functionality as the protecting group. This species remains intact though the phosphoramidite monomer synthesis as well as during oligonucleotide construction. These groups are not removed until the synthesized oligo is deprotected using ammonia. After protection, the crude material is then activated in situ via formation of an N-hydroxy succinimide ester (NHS-ester) using DCC as a coupling agent. The DCU byproduct is filtered away and an amino alcohol is added. Many amino alcohols are commercially available some of which are derived from reduction of amino acids. Only the amine is reactive enough to displace N-hydroxy succinimide.

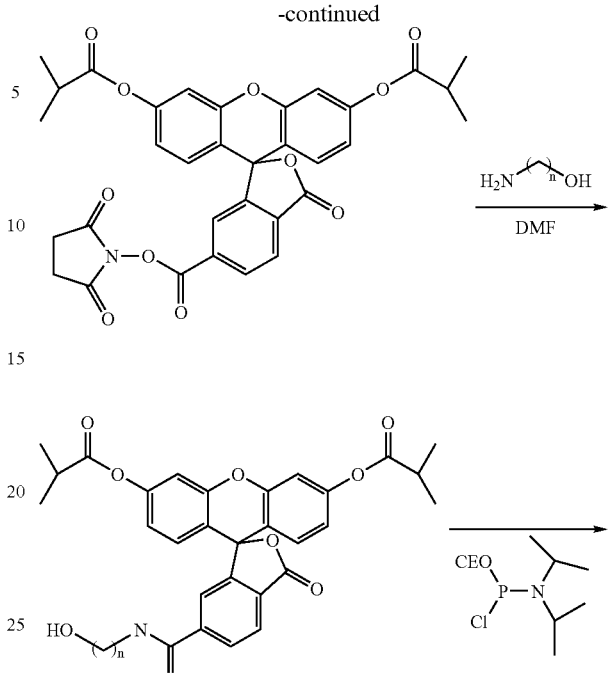

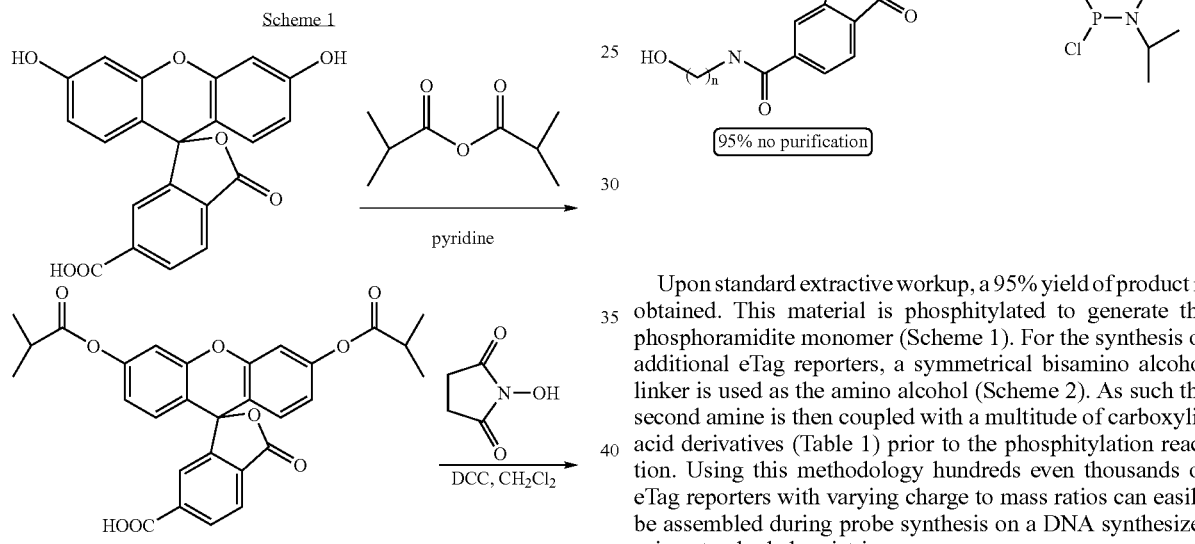

Upon standard extractive workup, a 95% yield of product is obtained. This material is phosphitylated to generate the phosphoramidite monomer (Scheme 1). For the synthesis of additional eTag reporters, a symmetrical bisamino alcohol linker is used as the amino alcohol (Scheme 2). As such the second amine is then coupled with a multitude of carboxylic acid derivatives (Table 1) prior to the phosphitylation reaction. Using this methodology hundreds even thousands of eTag reporters with varying charge to mass ratios can easily be assembled during probe synthesis on a DNA synthesizer using standard chemistries.

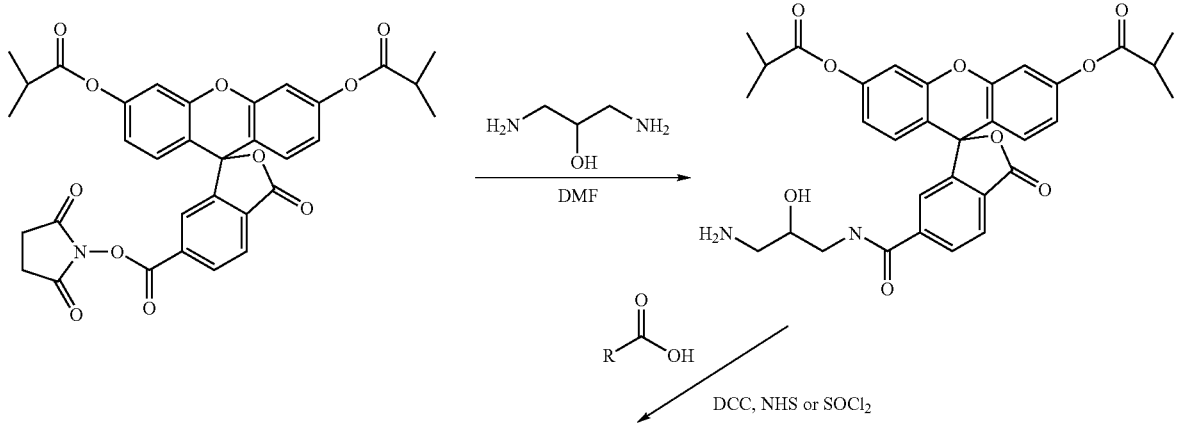

-continued

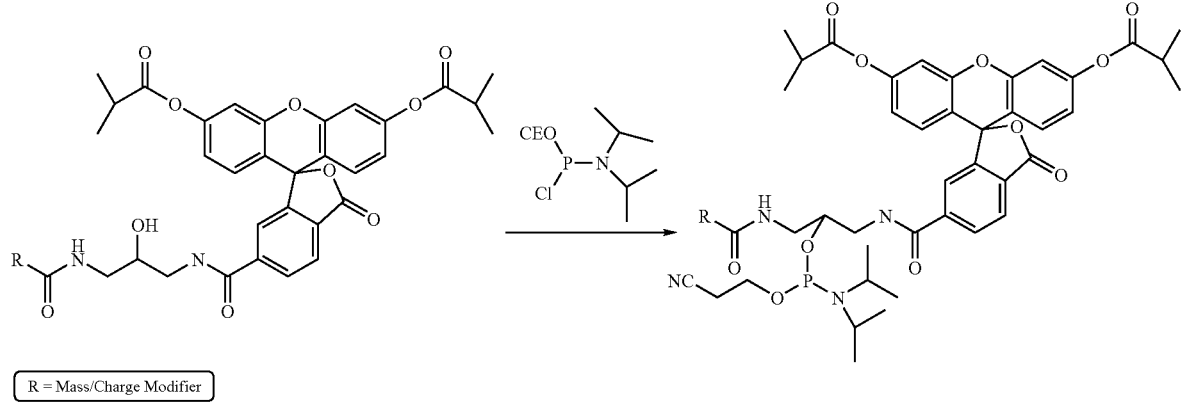

R = Mass/Charge Modifier

Additional eTag reporters are accessed via an alternative strategy which uses 5-aminofluorescein as starting material (Scheme 3). Addition of 5-aminofluorescein to a great excess of a diacid dichloride in a large volume of solvent allows for the predominant formation of the monoacylated product over dimer formation. The phenolic groups are not reactive under these conditions. Aqueous workup converts the terminal acid chloride to a carboxylic acid. This product is analogous to 6-carboxy fluorescein and using the same series of steps is converted to its protected phosphoramidite monomer (Scheme 3). There are many commercially available diacid dichlorides and diacids, which can be converted to diacid chlorides using $SOCl_2$ or acetyl chloride. This methodology is highly attractive in that a second mass modifier is used. As such, if one has access to 10 commercial modified phosphoramidites and 10 diacid dichlorides and 10 amino alcohols there is a potential for 1000 different eTag reporters. There are many commercial diacid dichlorides and amino alcohols (Table 3). These synthetic approaches are ideally suited for combinatorial chemistry.

TABLE 3

Mass and charge modifiers that can be used for conversion of amino dyes into eTag reporter phosphoramidite monomers.

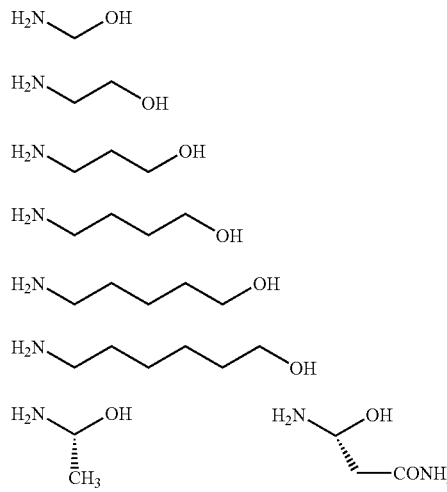

TABLE 3-continued

Mass and charge modifiers that can be used for conversion of amino dyes into eTag reporter phosphoramidite monomers.

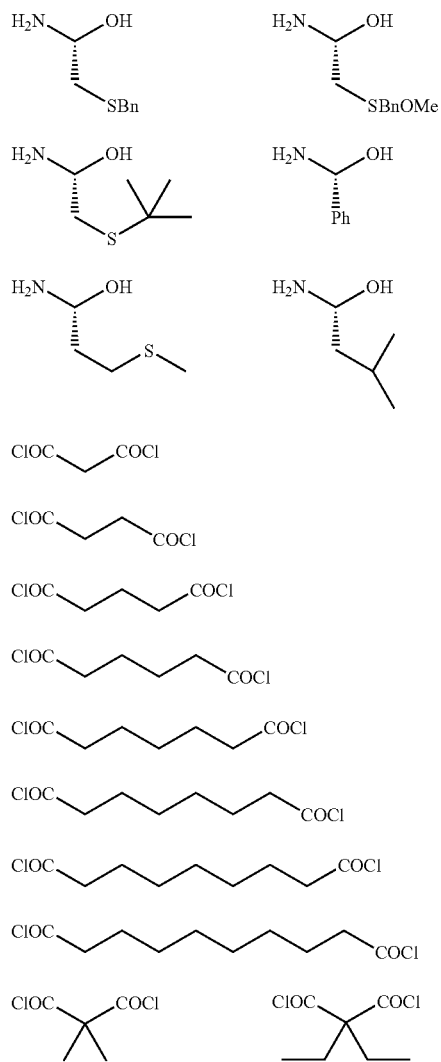

TABLE 3-continued

Mass and charge modifiers that can be used for conversion of amino dyes into eTag reporter phosphoramidite monomers.

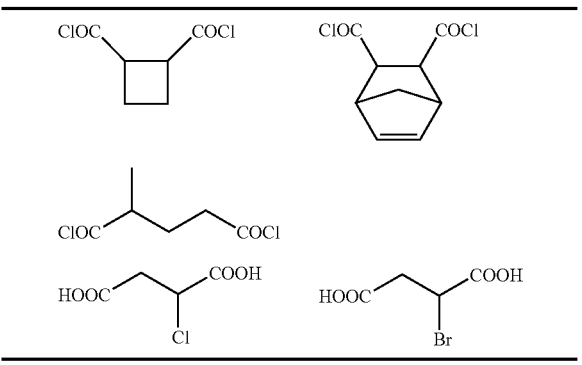

Scheme 3

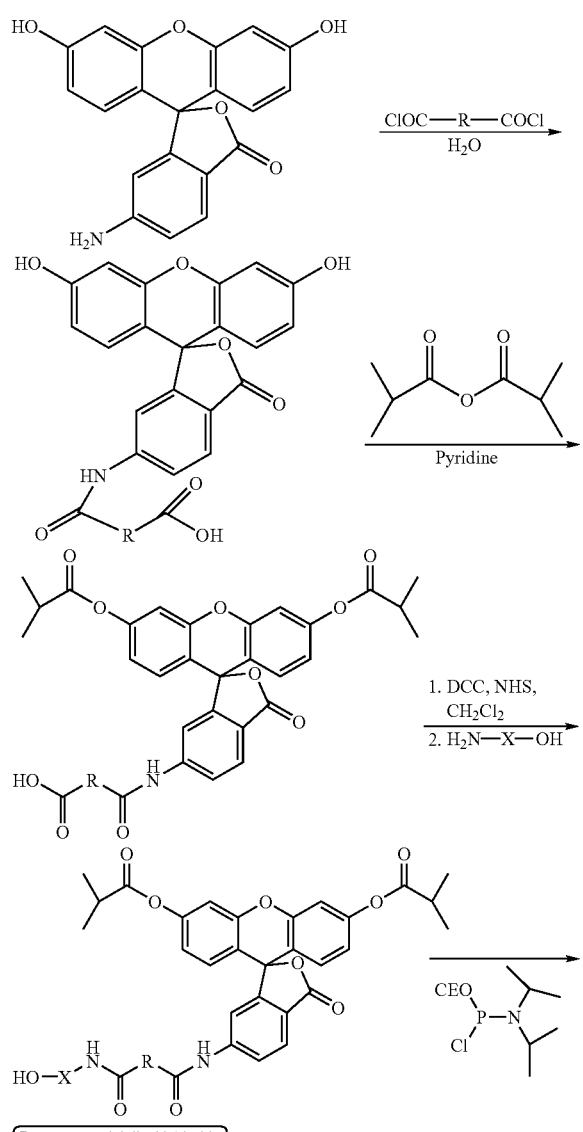

R = commercial diacidchloride
X = commercial amino alcohol

Substituted aryl groups can serve as both mass- and charge-modifying regions. (Table 4) Various functionalities may be substituted onto the aromatic group, e.g. phenyl, to provide mass as well as charges to the eTag reporter. The aryl group may be a terminal group, where only one linking functionality is required, so that a free hydroxyl group may be acylated, may be attached as a side chain to an hydroxyl present on the eTag reporter chain, or may have two functionalities, e.g. phenolic hydroxyls, that may serve for phophite ester formation and other substitutients, such as halo, haloalkyl, nitro, cyano, alkoxycarbonyl, alkylthio, etc. where the groups may be charged or uncharged.

TABLE 4

Benzoic acid derivatives as mass and charge modifiers. (Mass is written below each modifier)

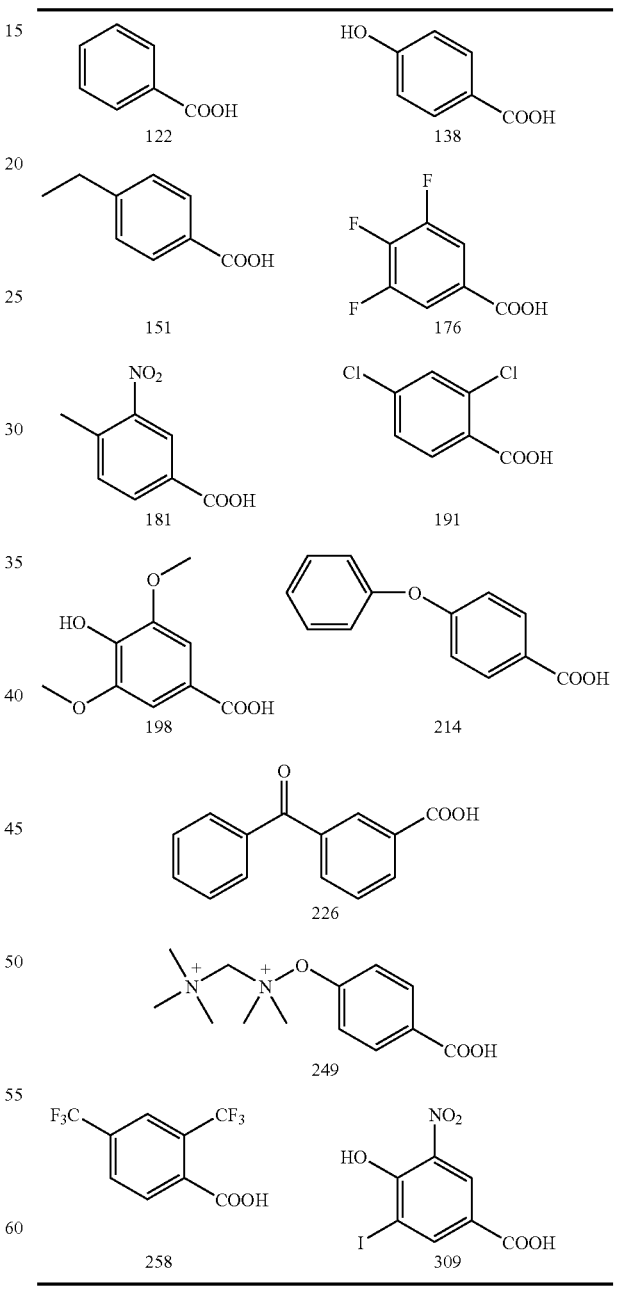

A variety of maleimide derivatized eTag reporters have also been synthesized. These compounds were subsequently bioconjugated to 5'-thiol adorned DNA sequences and subjected to the 5'-nuclease assay. The species formed upon cleavage are depicted in Table 5.

TABLE 5
eTag reporters derived from maleimide-linked precursors.
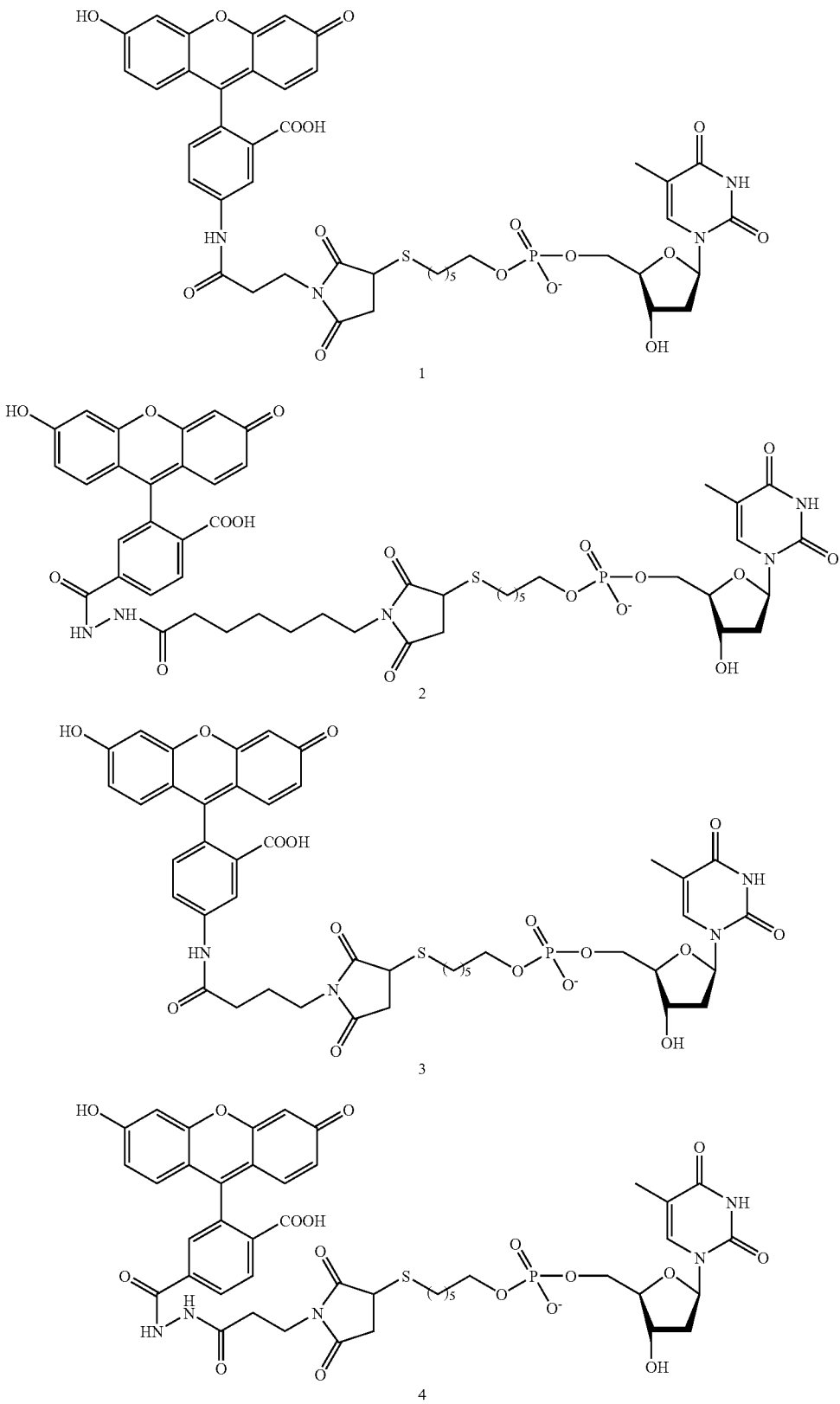

TABLE 5-continued
eTag reporters derived from maleimide-linked precursors.
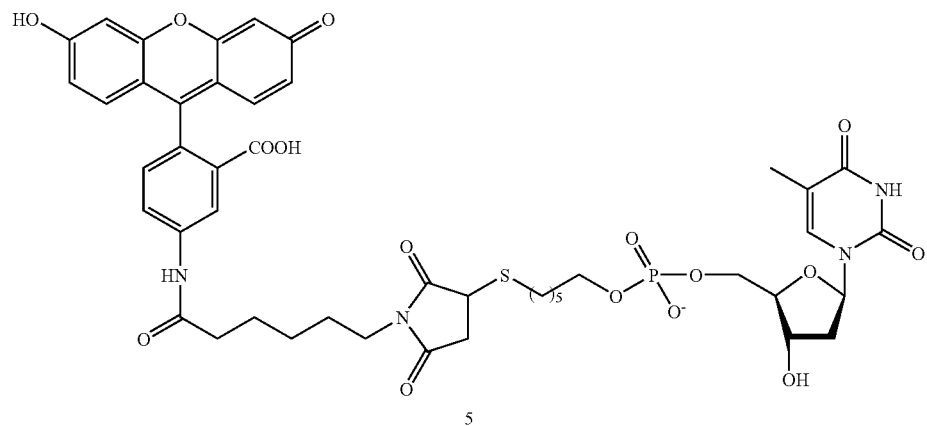
5
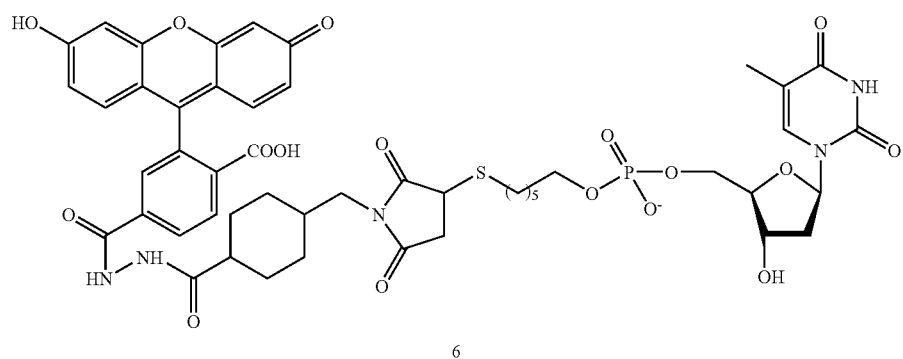
6
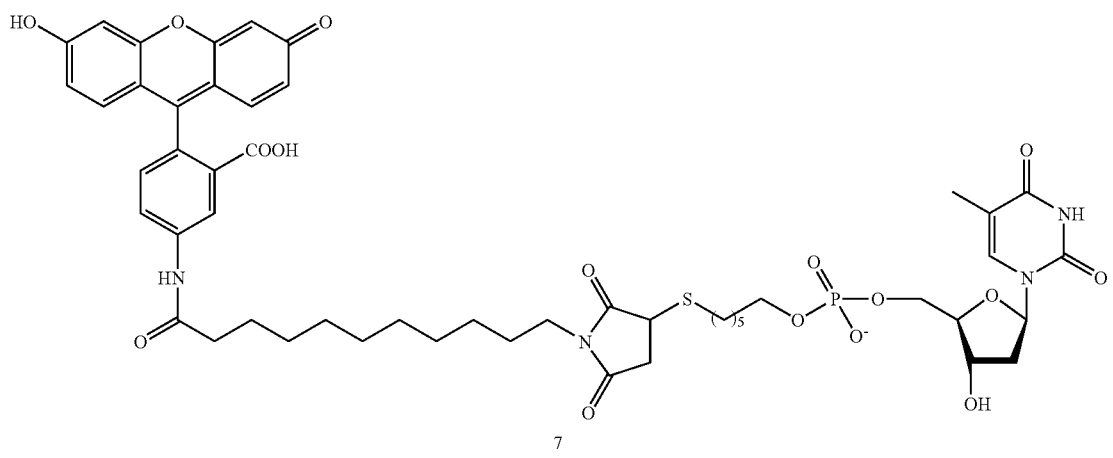
7

TABLE 5-continued eTag reporters derived from maleimide-linked precursors.

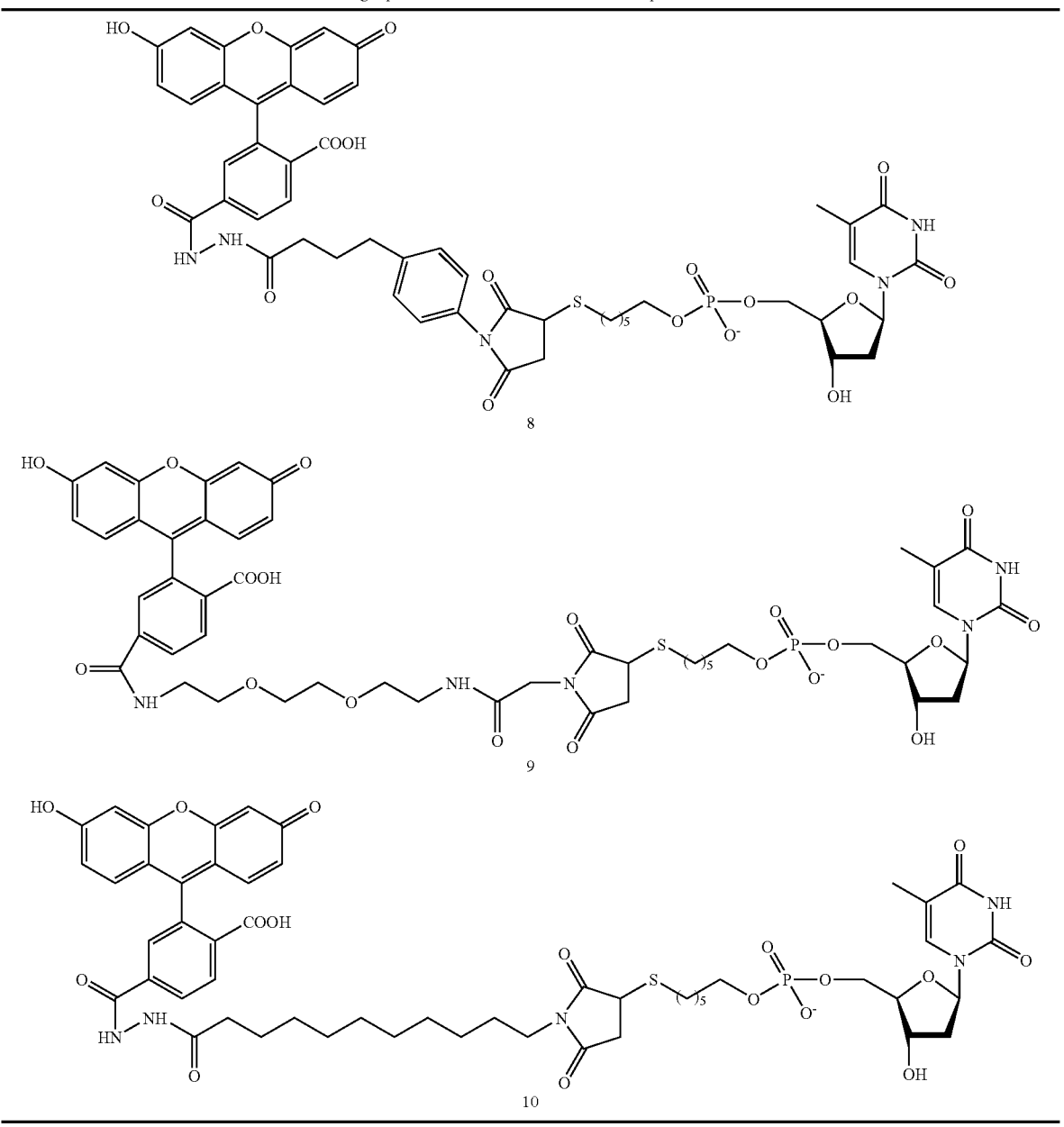

The eTag reporter may be assembled having an appropriate functionality at one end for linking to the binding compound. Thus for oligonucleotides, one would have a phosphoramidite or phosphate ester at the linking site to bond to an oligonucleotide chain, either 5' or 3', particularly after the oligonucleotide has been synthesized, while still on a solid support and before the blocking groups have been removed. While other techniques exist for linking the oligonucleotide to the eTag reporter, such as having a functionality at the oligonucleotide terminus that specifically reacts with a functionality on the eTag reporter, such as maleimide and thiol, or amino and carboxy, or amino and keto under reductive amination conditions, the phosphoramidite addition is preferred. For a peptide-binding compound, a variety of functionalities can be employed, much as with the oligonucleotide functionality, although phosphoramidite chemistry may only occasionally be appropriate. Thus, the functionalities normally present in a peptide, such as carboxy, amino, hydroxy and thiol may be the targets of a reactive functionality for forming a covalent bond.

Of particular interest in preparing eTag reporter labeled nucleic acid binding compounds is using the solid support phosphoramidite chemistry to build the eTag reporter as part of the oligonucleotide synthesis. Using this procedure, one attaches the next succeeding phosphate at the 5' or 3' position, usually the 5' position of the oligonucleotide chain. The added phosphoramidite may have a natural nucleotide or an unnatural nucleotide. Instead of phosphoramidite chemistry, one may use other types of linkers, such as thio analogs, amino acid analogs, etc. Also, one may use substituted nucleotides, where the mass-modifying region and/or the charge-modifying region may be attached to the nucleotide, or a ligand may be attached to the nucleotide. In this way, phosphoramidite links are added comprising the regions of the eTag reporter, whereby when the synthesis of the oligonucleotide chain is completed, one continues the addition of the regions of the eTag reporter to complete the molecule. Conveniently, one would provide each of the building blocks of the different regions with a phosphoramidite or phosphate ester at one end and a blocked functionality, where the free functionality can react with a phosphoramidite, mainly a hydroxyl. By using molecules for the different regions that have a phosphoramidite at one site and a protected hydroxyl at another site, the eTag reporter can be built up until the terminal region, which does not require the protected hydroxyl.

Illustrative of the synthesis would be to employ a diol, such as an alkylene diol, polyalkylene diol, with alkylene of from 2 to 3 carbon atoms, alkylene amine or poly(alkylene amine) diol, where the alkylenes are of from 2 to 3 carbon atoms and the nitrogens are substituted, for example with blocking groups or alkyl groups of from 1-6 carbon atoms, where one diol is blocked with a conventional protecting group, such as a dimethyltrityl group. This group can serve as the mass-modifying region and with the amino groups as the charge-modifying region as well. If desired, the mass modifier can be assembled by using building blocks that are joined through phosphoramidite chemistry. In this way the charge modifier can be interspersed between the mass modifier. For example, one could prepare a series of polyethylene oxide molecules having 1, 2, 3, n units. Where one wished to introduce a number of negative charges, one could use a small polyethylene oxide unit and build up the mass and charge-modifying region by having a plurality of the polyethylene oxide units joined by phosphate units. Alternatively, by employing a large spacer, fewer phosphate groups would be present, so that without large mass differences, one would have large differences in mass-to-charge ratios.

The chemistry that is employed is the conventional chemistry used in oligonucleotide synthesis, where building blocks other than nucleotides are used, but the reaction is the conventional phosphoramidite chemistry and the blocking group is the conventional dimethoxyltrityl group. Of course, other chemistries compatible with automated synthesizers can also be used, but there is no reason to add additional complexity to the process.

For the peptides, the eTag reporters will be linked in accordance with the chemistry of the linking group and the availability of functionalities on the peptide binding compound. For example, with Fab fragments specific for a target compound, a thiol group will be available for using an active olefin, e.g. maleimide, for thioether formation. Where lysines are available, one may use activated esters capable of reacting in water, such as nitrophenyl esters or pentafluorophenyl esters, or mixed anhydrides as with carbodiimide and half-ester carbonic acid. There is ample chemistry for conjugation in the literature, so that for each specific situation, there is ample precedent in the literature for the conjugation.

Once the binding compound conjugated with the eTag reporter has been prepared, it may find use in a number of different assays, many of which have already been discussed. The samples may be processed using lysing, nucleic acid separation from proteins and lipids and vice versa, and enrichment of different fractions. For nucleic acid related determinations, the source of the DNA may be any organism, prokaryotic and eukaryotic cells, tissue, environmental samples, etc. The DNA or RNA may be isolated by conventional means, RNA may be reverse transcribed, DNA may be amplified, as with PCR, primers may be used with ligands for use in subsequent processing, the DNA may be fragmented using restriction enzymes, specific sequences may be concentrated or removed using homologous sequences bound to a support, or the like. Proteins may be isolated using precipitation, extraction, and chromatography. The proteins may be present as individual proteins or combined in various aggregations, such as organelles, cells, viruses, etc. Once the target components have been preliminarily treated, the sample may then be combined with the eTag reporter targeted binding proteins.

For a nucleic acid sample, after processing, the probe mixture of eTag reporters for the target sequences will be combined with the sample under hybridization conditions, in conjunction with other reagents, as necessary. Where the reaction is heterogeneous, the target sequence will have a ligand for binding to a reciprocal binding member for sequestering hybrids to which the eTag reporter is bound. In this case, all of the DNA sample carrying the ligand will be sequestered, both with and without eTag reporter labeled probe. After sequestering the sample, and removing non-specific binding eTag reporter labeled probe under a predetermined stringency based on the probe sequence, using washing at an elevated temperature, salt concentration, organic solvent, etc., the eTag reporter is released into an electrophoretic buffer solution for analysis.

For a homogeneous assay, the sample, eTag reporter labeled probe mixture and ancillary reagents are combined in a reaction mixture supporting the cleavage of the linking region. The mixture may be processed to separate the eTag reporters from the other components of the mixture. The mixture, with or without eTag reporter enrichment, may then be transferred to an electrophoresis device, usually a microfluidic or capillary electrophoresis device and the medium modified as required for the electrophoretic separation. Where one wishes to remove from the separation channel intact eTag reporter molecules, a ligand is bound to the eTag reporter that is not released when the eTag reporter is released. Alternatively, by adding a reciprocal binding member that has the opposite charge of the eTag reporter, so that the overall charge is opposite to the charge of the eTag reporter, these molecules will migrate toward the opposite electrode from the released eTag reporter molecules. For example, one could use biotin and streptavidin, where streptavidin carries a positive charge. In the case of an oligonucleotide, the eTag reporter label would be bonded to at least two nucleotides, where cleavage occurs between the two nucleotides with release of the eTag reporter, with the terminal nucleotide of the dinucleotide labeled with a biotin (the eTag reporter would be released without the biotinylated nucleotide). In the case of a peptide analyte, one would have cleavage at a site, where the ligand remains with the peptide analyte. For example, one could have the eTag reporter substituted for the methyl group of methionine. Using the pyrazolone of the modified methionine, one could bond to an available lysine. The amino group of the pyrazolone would be substituted with biotin. Cleavage would then be achieved with cyanogen bromide, releasing the eTag reporter, but the biotin would remain with the peptide and any eTag reporter that was not released from the binding member. Avidin is then used to change the polarity or sequester the eTag reporter conjugated to the binding compound.

The separation of the eTag reporters by electrophoresis can be performed in conventional ways. See, for example, U.S. Pat. Nos. 5,750,015; 5,866,345; 5,935,401; 6,103,199, and 6,110,343 and WO98/5269, and references cited therein. Also, the sample can be prepared for mass spectrometry in conventional ways. See, for example, U.S. Pat. Nos. 5,965, 363; 6,043,031; 6,057,543 and 6,111,251.

For convenience, kits can be provided comprising building blocks for preparation of eTag reporters in situ or have assembled eTag reporters for direct bonding to the binding compound. For preparing the eTag reporter in situ during the synthesis of oligonucleotides, one would provide phosphoramidites or phosphates, where the esters would include alkyl groups, particularly of from 1 to 3 carbon atoms, and cyanoethyl groups, while for the phosphoramidite, dialkylamino, where the alkyl groups are of from 1-4 carbon atoms, while the other group would be a protected hydroxy, where the protecting group would be common to oligonucleotide synthesis, e.g. dimethoxytrityl. For large numbers of eTag reporters, that is, 20 or more, one kit would supply at least 3 each of mass-modifying regions and charge-modifying regions, each having at least the phosphate linking group and a protected hydroxyl. The two functional groups may be separated by 2 or more atoms, usually not more than about 60 atoms, and may be vicinal ($\alpha,\beta$ to $\alpha,\omega$). The nature of the compounds has been discussed previously. In the simplest case, the phosphorous acid derivative would serve as the charge-modifying region, so that the mass-modifying region and the charge-modifying region would be added as a single group. In addition, one would have at least 2 detectable regions, which would be a fluorescer having the phosphate linker and other functionalities protected for purposes of the synthesis. Alternatively, instead of having the detection region the terminal region, where the detectable region allows for the presence of two functionalities that can be used for linking, one of the other regions may serve as the terminal region. Also, one of the regions may be conveniently linked to a mono- or dinucleotide for direct linking to the oligonucleotide chain, where cleavage will occur at the 3' site of the nucleotide attached to the eTag reporter. By using tri- or tetrasubstituted groups, one can provide a detectable region that provides the pair for energy transfer. One need only have one or two different energy transfer agents, while having a plurality of emitting agents to greatly expand the number of different eTag reporters.

Other reagents that are useful include a ligand-modified nucleotide and its receptor. Ligands and receptors include biotin and strept/avidin, ligand and antiligand, e.g. digoxin or derivative thereof and antidigoxin, etc. By having a ligand conjugated to the oligonucleotide, one can sequester the eTag conjugated oligonucleotide probe and its target with the receptor, remove unhybridized eTag reporter conjugated oligonucleotide and then release the bound eTag reporters or bind an oppositely charged receptor, so that the ligand-receptor complex with the eTag reporter migrates in the opposite direction.

Where one prepares the eTag reporter, there will be the additional linking region, which in the above description is served by the phosphorous acid derivative or the mono- or dinucleotide unit phosphorous acid derivative. For these eTag reporters, one need not be restricted to phosphate links, but may use other convenient chemistries, particularly chemistries that are automated. Thus, instead of phosphorous acid and protected alcohol, one can use carboxy and alcohol or amino, activated olefin and thiol, amino and oxo-carbonyl, particularly with reductive amination, an hydroxy with an active halide or another hydroxy to form an ether, and the like. One may employ compounds that are difunctional with the same or different functionalities, where one could have a diacid and a diol or an hydroxyacid or cyclic ester for producing the eTag reporter. Numerous examples of these types of compounds have already been described and are well known in the literature. By appropriate selection of the monomers and conditions, one can select a particular order of reaction, namely the number of monomers that react or one may separate the mixture by the different mobilities.

For separations based on sorption, adsorption and/or absorption, the nature of the eTag reporters to provide for differentiation can be relatively simple. By using differences in composition, such as aliphatic compounds, aromatic compounds and halo derivatives thereof, one may make the determinations with gas chromatography, with electron capture or negative ion mass spectrometry, when electronegative atoms are present. In this way one may use hydrocarbons or halo-substituted hydrocarbons as the eTag reporters bonded to a releasable linker. See, U.S. Pat. Nos. 5,565,324 and 6,001, 579, which are specifically incorporated by reference as to the relevant disclosure concerning cleavable groups and detectable groups.

The kits will include at least two detectable regions and sufficient reagents to have at least 10, usually at least 20 and frequently at least 50 or more different eTag reporters that can be separated by their mobility.

For 20 different eTag reporters, one only requires 5 different mass-modifying regions, one phosphate link and four different detectable regions. For 120 eTag reporters, one need only have 10 different mass-modifying regions, 3 different charge-modifying regions and 4 different detectable regions. For 500 different eTag reporters, one need only have 25 different mass-modifying regions, 5 different charge-modifying regions and 4 different detectable regions.

For an inclusive but not exclusive listing of the various manners in which the subject invention may be used, the following table is provided.

Recognition event leads to generation or modification of eTag reporters.

| Recognition Event | eTag reporter Activation | Amplification Mode | Format |
|---|---|---|---|
| Binding Assays (solution Phase eTag reporter generation followed by separation by CE, HPLC or Mass Spectra) | | | Multiplexed assays (2-1000) leading to release of library of eTag reporters. Every eTag reporter codes for a unique binding event or assay. |

| Recognition Event | eTag reporter Activation | Amplification Mode | Format |
|---|---|---|---|
| Hybridization followed by enzyme recognition | 5' Nuclease assay | PCR, Invader | Sequence recognition for example for multiplexed gene expression, SNP's scoring etc . . . |
| | 3' Nuclease assay | | Multiplexed assays Sequence recognition |
| | Restriction enzymes | | Multiplexed assays Sequence recognition |
| | Ribonuclease H | | Multiplexed assays Sequence recognition |
| Hybridization followed by channeling | Singlet Oxygen | Single eTag reporter release per binding event | Multiplexed assays Sequence recognition |
| Hybridization followed by channeling | Singlet Oxygen | Amplification due to turnover of eTag reporter binding moiety | Multiplexed assays Sequence recognition |
| | | Amplification due to release of multiple eTag reporters (10 to 100,000) per binding event | Multiplexed assays Sequence recognition |
| | Hydrogen peroxide | Amplification due to turnover of eTag reporter binding moiety | Multiplexed assays Sequence recognition |
| | | Amplification due to release of multiple eTag reporters (10 to 100,000) per binding event | Multiplexed assays Sequence recognition |
| | Light; Energy Transfer | Amplification due to turnover (Photocleavage) of eTag reporter binding moiety | Multiplexed assays Sequence recognition |
| | | Amplification due to release of multiple eTag reporters (10 to 100,000) per binding event | Multiplexed assays Sequence recognition |
| IMMUNOASSAYS | | | |
| Sandwich assays Antibody-1 decorated with Sensitizer while antibody-2 Is decorated with singlet oxygen cleavable eTag reporters | Singlet Oxygen | A few (2-10) eTag reporters release per binding event | Proteomics Multiplexed Immunoassays |
| | Singlet Oxygen | Amplification due to release of multiple eTag reporters (10 to 100,000) per binding event | Proteomics Multiplexed Immunoassays |
| Sandwich assays Antibody-1 decorated with Glucose oxidase while antibody-2 Is decorated with hydrogen peroxide cleavable eTag reporters | Hydrogen Peroxide | A few (2-10) eTag reporters release per binding event | Proteomics Multiplexed Immunoassays |
| | Hydrogen Peroxide | Amplification due to release of multiple eTag reporters (10 to 100,000) per binding event | Proteomics Multiplexed Immunoassays |
| Competition assays Antibody-1 decorated with Sensitizer while Antigen Is decorated with singlet oxygen cleavable eTag reporters | Singlet Oxygen | A few (2-10) eTag reporters release per binding event | |

The following examples are offered by way of illustration and not by way of limitation.

EXPERIMENTAL

Synthetic Preparation of Modified Fluorescein Phosphoramidites

Pivaloyl protected carboxyfluorescein: Into a 50 mL round bottom flask was placed 5(6)-carboxyfluorescein (0.94 g, 2.5 mmol), potassium carbonate (1.0 g, 7.5 mmol) and 20 mL of dry DMF. The reaction was stirred under nitrogen for 10 min, after which trimethylacetic anhydride (1.1 mL, 5.5 mmol) was added via syringe. The reaction was stirred at room temperature overnight, and then filtered to remove excess potassium carbonate and finally poured into 50 mL of 10% HCl. A sticky yellow solid precipitated out of solution. The aqueous solution was decanted off and the residual solid was dissolved in 10 mL of methanol. Dropwise addition of this solution to 10% HCl yielded a fine yellow precipitate, which was filtered and air dried to yield an off white solid (0.88 g, 62%). TLC (45:45:10 Hxn,EtOAc,MeOH)

NHS ester of protected pivaloyl carboxyfluorescein. Into a 200 mL round bottom flask was placed the protected carboxyfluorescein (2.77 g, 5.1 mmol) and 50 mL of dichloromethane. N-hydroxysuccinimide (0.88 g, 7.6 mmol) and dicyclohexylcarbodiimide (1.57 g, 7.6 mmol) were added and the reaction was stirred at room temperature for 3 hours. The reaction was then filtered to remove the precipitated dicyclohexyl urea byproduct and reduced to approx. 10 mL of solvent in vacuo. Dropwise addition of hexanes with cooling produced a yellow-orange colored solid, which was triturated with hexanes, filtered and air dried to yield 3.17 g (95%) of product. TLC (45:45:10 Hxn,EtOAc,MeOH)

Alcohol. Into a 100 mL round bottom flask was placed the NHS ester (0.86 g, 1.34 mmol) and 25 mL of dichloromethane. The solution was stirred under nitrogen after which aminoethanol (81 µL, 1 eq) was added via syringe. The reaction was monitored by TLC (45:45:10 Hxn,EtOAc, MeOH) and was found to be complete after 10 min. The dichloromethane was then removed in vacuo and the residue dissolved in EtOAc, filtered and absorbed onto 1 g of silica gel. This was bedded onto a 50 g silica column and eluted with Hxn:EtOAc:MeOH (9:9:1) to give 125 mg (20%) of clean product.

Phosphoramidite. Into a 10 mL round bottom flask containing 125 mg of the alcohol was added 5 mL of dichloromethane. Diisopropyl ethylamine (139 µl, 0.8 mmol) was added via syringe. The colorless solution turned bright yellow. 2-cyanoethyl diisopropylchlorophosphoramidite (81 µl, 0.34 mmol) was added via syringe and the solution immediately went colorless. After 1 hour TLC (45:45:10 Hxn:EtOAc:TEA) showed the reaction was complete with the formation of two closely eluting isomers. Material was purified on a silica column (45:45:10 Hxn:EtOAc:TEA) isolating both isomers together and yielding 130 mg (85%).

Carboxylic acid. Into a 4 mL vial was placed 12-aminododecanoic acid (0.1 g, 0.5 mmol) and 2 mL of pyridine. To this suspension was added chlorotrimethyl silane (69 µL, 1.1 eq) via syringe. After all material dissolved (10 min) NHS ester (210 mg, 0.66 eq) was added. The reaction was stirred at room temperature overnight and then poured into water to precipitate a yellow solid, which was filtered, washed with water, and air dried. TLC (45:45:10 Hxn:EtOAc:MeOH) shows a mixture of two isomers.

General Procedure for Remaining Syntheses. The carboxylic acid formed described above is to be activated by NHS ester formation with 1.5 eq each of N-hydroxysuccinimide and dicyclohexylcarbodiimide in dichloromethane. After filtration of the resulting dicyclohexylurea, treatment with 1 eq of varying amino alcohols will effect amide bond formation and result in a terminal alcohol. Phosphitylation using standard conditions described above will provide the phosphoramidite.

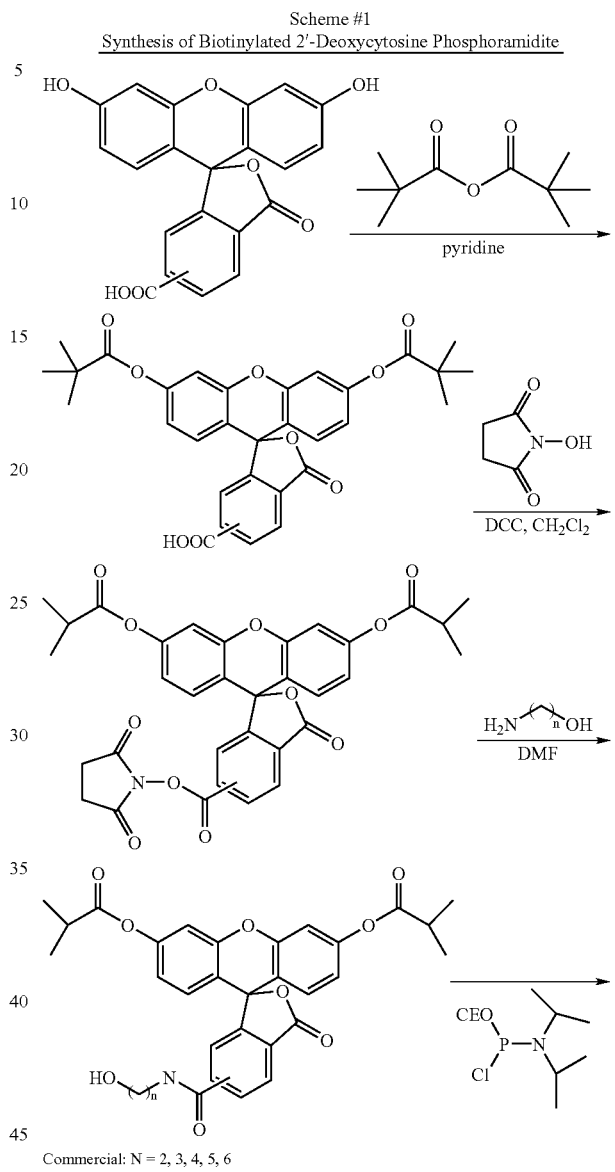

Scheme #1
Synthesis of Biotinylated 2'-Deoxycytosine Phosphoramidite

Commercial: N = 2, 3, 4, 5, 6

Synthesis of 3',5'-O-di-t-butyldimethylsilyl-2'-Deoxyuridine(1)

2'-Deoxyuridine (4 gm, 17.5 mmol) and imidazole (3.47 gm, 52.5 mmol) were dissolved in 30 ml of dry DMF and t-butyldimethyl-silyl chloride (7.87 gm, 52.5 mmol) added to the stirring solution at room temperature. After 3 hrs, TLC on silica gel (10% MeOH+90% CH$_2$Cl$_2$) showed that all starting material had been converted to a new compound with higher R$_f$. The solution was concentrated into a small volume, then about 200 ml of ether was added and washed three times with saturated aqueous NaCl solution. The organic layer was dried over anhydrous Na$_2$SO$_4$, and the filtrate was evaporated to give a colorless gummy material which converted to a white solid product (eight gm, 100%). This product was identified with HNMR and ES-MS.

Synthesis of 3',5'-O-di-t-butyldimethylsilyl-N⁴-(1,2,4-triazolo)-2'-Deoxycytidine(2)

1,2,4-Triazole (19.45 gm, 282 mmol) was suspended in 300 ml of anhydrous $CH_3CN$ at 0° C., 8 ml of $POCl_3$, then 50 ml of triethylamine was added slowly in 5 min. After an hour, 3',5'-O-Di-t-butyldimethylsilyl-2'-Deoxyuridine (1) (9 gm, 19.7 mmol) was dissolved in 200 ml of dry $CH_3CN$ and added to the reaction over 20 min. After stirring the reaction for 16 hours at RT, TLC (100% ether) showed that all starting material was converted to a new compound with lower $R_f$. The reaction mixture was filtered, reduced the volume of $CH_3CN$, diluted with ethyl acetate and washed with saturated aqueous $NaHCO_3$ then twice with saturated aqueous NaCl. The organic layer was dried over anhydrous $Na_2SO_4$ and the solvent was evaporated, co-evaporated from toluene to give a yellow solid product (10 gm. 100%). This product was identified with HNMR and ES-MS.

Synthesis of 3',5-O-di-t-butyldimethylsilyl-N⁴-(4,7,10-trioxa-1-tridecaneamino)-2'-Deoxycytidine (3)

4,7,10-Trioxa-1,13-tridecanediamine (10.44 gm, 47.4 mmol) was dissolved in 100 ml dioxane, then 3',5-O-di-t-butyldimethylsilyl4-(1,2,4-triazolo)-2-deoxycytidine (2) (8.03 gm, 15.8 mmol) was dissolved in 200 ml of dioxane (heated to about 50 C and cooling it dawn to RT) and added dropwise in 10 min., to the solution of 4,7,10-Trioxa-1,13-tridecanediamine with vigorous stirring at RT. After 5 hrs, TLC on silica gel showed that all starting material was converted to a new product with lower $R_f$, the resulting mixture was evaporated to dryness. The residue was dissolved in dichloromethane and washed twice with 5% sodium bicarbonate solution and saturated sodium chloride solution. The organic layer was dried over sodium sulphate, filtered and evaporated to dryness to give a yellow gummy product (7.87 gm). The product was purified on a silica gel column eluted with a gradient of 0 to 10% methanol in dichloromethane with 1% triethylamine. The product was obtained as a yellowish gum (5.66 gm, 54%). This product was identified with HNMR and ES-MS.

Synthesis of 3',5'-O-di-t-butyldimethylsilyl-4-N-(4,7,10-trioxa-1-tridecaneaminobiotin)-2'-Deoxycytidine (4)

3', 5'-O-di-t-butyldimethylsilyl-4-N-(4,7,10-trioxa-1-tridecaneamino)-2'-deoxycytidine(3)(2.657 gm, 4.43 mmol) and Biotin-NHS ester (1.814 gm, 5.316 mmol) were dissolved in 20 ml of dry DMF and about 1 ml of triethylamine was added. After stirring the reaction mixture for 4 hrs at RT, the reaction was stopped by evaporating all DMF to give a yellow gum material (4.36 gm). This material was dissolved in dichloromethane and washed three times with saturated solution of NaCl, dried over sodium sulphate and evaporated to dryness. TLC on silica gel (5% MeOH+1% TEA+94% $CH_2Cl_2$) indicated the formation of a new product which was higher $R_f$. This product was purified with column chromatography on silica gel using (99% $CH_2Cl_2$+1% TEA) to (1% MeOH+1% TEA+98% $CH_2Cl_2$) to yield a yellow foamy product (2.13 gm, 60%). This product was identified with HNMR and ES-MS.

Synthesis of 4-N-(4,7,10-trioxa-1-tridecaneaminobiotin)-2'-Deoxycytidine(5)

3',5'-O-di-t-butyldimethylsilyl-4-N-(4,7,10-trioxa-1-tridecaneaminobiotin)-2'-deoxycytidine(4) (1.6 gm, 1.8 mmol) was dissolved in 50 ml of dry THF, then about 5.5 ml of tetrabutylammonium fluoride in THF was added in 2 min. while stirring at RT. After 3 hrs, TLC on silica gel (10% MeOH+1% TEA+89% $CH_2Cl_2$) showed that a new product with lower $R_f$ formed. The solvent was evaporated to give a yellow oily product. Column chromatography on silica gel eluted with (99% $CH_2Cl_2$+1% TEA) to (7% MeOH+1% TEA+92% $CH_2Cl_2$) permitted the purification of the product as a gummy colorless product (1.14 gm, 97%). This product was identified with HNMR and ES-MS.

t-Butylbenzoylation of the biotin of 4-N-(4,7,10-trioxa-1-tridecaneaminobiotin)-2'-deoxycytidine (6)

4-N-(4,7,10-trioxa-1-tridecaneaminobiotin)-2'-Deoxycytidine (5) (14.14 gm, 21.5 mmol) was dissolved in 100 ml of dry pyridine. Chlorotrimethyl silane (11.62 gm, 107.6 mmol) was added and the mixture was stirred for 2 hrs at RT. 4-t-butylbenzoyl chloride (5.07 gm, 25.8 mmol) was added and the mixture was stirred for another 2 hrs at RT. The reaction mixture was cooled with ice-bath and the reaction stopped by adding 50 ml of water and 50 ml of 28% aqueous ammonia solution. The solution kept stirring at RT for 20 min., then evaporated to dryness in high vacuum and finally co-evaporated twice from toluene. The material was dissolved in dichloromethane and extracted twice with 5% aqueous sodium bicarbonate solution. The organic layer was dried over sodium sulphate, evaporated to dryness, re-dissolved in dichloromethane and applied to a silica gel column. The column was eluted with gradient from 0 to 10% of methanol in dichloromethane and obtained a product as a white foam (9.4 gm, 53.5%). This product was identified with HNMR and ES-MS.

Synthesis of 5'-O-(4,4'-dimethoxytriphenylmethyl)-4-N-(4,7,10-trioxa-1-tridecaneaminobiotin)-2'-Deoxycytidine (7)

Compound (6) (10.82 gm, 13.3 mmol) was co-evaporated twice from dry pyridine, then dissolved in pyridine (100 ml) and 4,4'-dimethoxytritylchloride (DMT-Cl) (6.76 gm, 19.95 mmol) was added and the resulting mixture stirred for 3 hrs. TLC (10% MeOH+1% TEA+89% $CH_2Cl_2$) showed the formation of new product with higher $R_f$, and some starting material remained unreacted, then another amount of DMTCl (2 gm) was added and kept stirring for 2 hrs. The reaction stopped by adding ethanol and the mixture was stirred for 15 min. After evaporation to dryness and co-evaporation from toluene, the material was dissolved in dichloromethane. The organic layer washed twice with 5% aqueous sodium bicarbonate solution, dried over sodium sulphate, evaporated to dryness. The product was purified on a silica column using a gradient of methanol from 0 to 5% in dichloromethane/1% TEA. The product was obtained as a white foam (4.55 gm, 31%). This product was identified with HNMR and ES-MS.

Synthesis of 3'-O-[(diisopropylamine)(2-cyanoethoxy) phosphino)]-5'-O-(4,4'-dimethoxytriphenylmethyl)-4-N-(4,7,10-trioxa-1-tridecaneaminobiotin)-2'-Deoxycytidine (8)

The 5'-DMT-Biotin-dC (7) (507 mg, 0.453 mmol) was dissolved in dry acetonitrile (30 ml) and dichloromethane (5 ml), then diisopropylamine (73 mg, 0.56 mmol), tetrazole (1.15 ml, 0.52 mmol) and 2-cyanoethyl N,N,N'N'-tetraisopropylphosphane 214 mg, 234 ul, 0.7 mmol) were added and the mixture stirred under nitrogen at RT. After 2 hrs, TLC on silica gel (45%/45%/5%/5%: Ethyl acetate/dichloromethane/triethylamine/methanol) showed that only about 30% of product was formed and about 70% of starting material was unreacted. More reagents were added until most of starting material was converted, only about 5% left unreacted. The solvent was evaporated to dryness, dissolved in dry dichloromethane, washed with sodium bicarbonate solution (5%), saturated brine solution, then the organic layer dried over sodium sulphate, evaporated to dryness. Column chromatography on silica gel using (48%/48%/4%: Ethyl acetate/dichloromethane/triethylamine) to (47%/47%/5%/1%: Ethyl acetate/dichloromethane/triethylamine/methanol). The desired product was obtained as a colorless gummy product (406 mg, 70%). This material was co-evaporated three times from a mixture of dry benzene and dichloromethane, then was kept in desiccated containing $P_2O_5$ and NaOH pellets under vacuum for 26 hrs before used in DNA synthesis.

Synthesis of Biotinylated 2'-Deoxyadenosine Phosphoramidite

Scheme#2

Synthesis of 8-Bromo-2'-Deoxyadenosine

2'-Deoxyadenosine (7 gm. 25.9 mmol) was dissolved in sodium acetate buffer (150, 1 M, pH5.0) by worming it to about 50 C, then was cooled dawn to 30 C, then 3 ml of bromine in 100 ml of the same buffer was added dropwise at RT for 15 min., to the reaction. After, 6 hrs the TLC on silica gel (20% MeOH in CH2Cl2) showed that all starting material was converted to a new product. The reaction was discolored by adding some sodium metabisulfite ($Na_2S_2O_5$) while it was stirring, the color changed to a white solution, the pH of the reaction was neutralized by adding NaOH (1M solution). The reaction mixture was kept at 4° C. (refrigerator) for 16 hrs. Next day the solid material was filtered, washed with cold water, then acetone to give a solid yellow powder product (5.75 gm. 64%). The structure of this product was confirmed by H NMR and ES-MS.

Synthesis of $N^6$-Benzoyl-8-bromo-5'-O-(4,4'-dimethoxytrityl)-2'-Deoxyadenosine (1)

8-Bromo-2'-Deoxyadenosine (7.7 gm. 22.17 mmol) was dried by co-evaporation with dry pyridine and the solid was suspended in 200 ml of dry pyridine followed by the addition of 4,4'-dimethoxytriphenylmethyl chloride (DMT-Cl) (9 gm, 26.6 mmol). After stirring for 4 hrs at RT, TLC on silica gel showed that a new product was formed and some starting material was unreacted. Another amount of DMT-Cl (3 gm) was added and stirred at RT for 2 hrs. When TLC showed that all starting material was converted to new product with higher Rf, the reaction mixture was cooled to 0 C and trimethylchlorosilane (12.042 gm., 14 ml, 110.85 mmol) was added dropwise while cooling and after 40 min. while stirring benzoyl chloride (15.58 gm, 12.88 ml, 110.85 mmol) was similarly added. The reaction was allowed to react at RT over 2 hrs. The reaction was quenched by slow addition of cold water (50 ml), followed by addition of concentrated ammonia (30%, 50 ml). After 30 min. the reaction mixture was evaporated to dryness. The residue was dissolved in water, and the solution was extracted with ethyl acetate three times, the organic layer washed with saturated sodium bicarbonate solution, and then brine. The organic phase was dried over sodium sulphate, evaporated to dryness. The product was purified on a silica column chromatography, to give a yellowish solid product (6.79 gm, 41.6%). The structure of this product was confirmed by H NMR and ES-MS.

Synthesis of $N^6$-benzoyl-8-bromo-3'-O-t-butyldimethylsilyl-5'-O-(4,4'-dimethoxytrityl)-2'-deoxyadenosine 6N-Benzoyl-8-bromo-5'-O-(4,4'-dimethoxytrityl)-2'-Deoxyadenosine(1) (14 gm. 19 mmol) and imidazole (1.94 gm, 28.5 mmol) were dissolved in 100 ml of dry DMF and t-butyldimethyl-silyl chloride (4.3 gm, 28.5 mmol) added to the stirring solution at room temperature. After 4 hrs, TLC on silica gel (2.5% MeOH in $CH_2Cl_2$) showed that all starting material had been converted to a new product with higher $R_f$. The solution was concentrated into a small volume, then about 400 ml of ether was added and washed three times with saturated aqueous NaCl solution. The organic layer was dried over anhydrous $Na_2SO_4$, and the filtrate was evaporated to give an off-white foamy product (16.18 gm, 100%). H NMR and ES-MS confirmed the structure.

Synthesis of $N^6$-benzoyl-8-(4,7,10-trioxa-1-tridecaneamino)-3'-O-t-butyldimethylsilyl-5'-O-(4,4'-dimethoxytrityl)-2'-deoxyadenosine (2)

$N^6$-Benzoyl-8-bromo-3'-O-t-butyldimethylsilyl-5'-O-(4,4'-dimethoxytrityl)-2'-deoxyadenosine (8.31 gm. 9.7 mmol) was dissolved in 200 ml of ethanol then 4,7,10-trioxa-1,13-tridecanediamine (6.75 gm. 6.7 ml. 30 mmol) was added at once and kept stirring at 50 C. After 16 hrs TLC showed that all starting material was converted to a one major product with lower Rf and other minor products. The solvent was evaporated to dryness, dissolved in dichloromethane, washed three times with solution of brine, dried over anhydrous $Na_2SO_4$, evaporated to give a yellow gummy material. Column chromatography (1% TEA+$CH_2Cl_2$) to (1% TEA+5% MeOH+$CH_2Cl_2$) permitted the purification of the major product as an off-white gummy material (4.53 gm. 47%). This product was identified with HNMR and ES-MS.

Synthesis of $N^6$-benzoyl-8-(4,7,10-trioxa-1-tridecaneaminobiotin)-3'-O-t-butyldimethylsilyl-5'-O-(4,4'-dimethoxytrityl)-2'-deoxyadenosine $N^6$-benzoyl-8-(4,7,10-trioxa-1-tridecaneamino)-3'-O-t-butyldimethylsilyl-5'-O-(4,4'-dimethoxytrityl)-2'-deoxyadenosine (4.53 gm. 4.57 mmol) and biotin-NHS ester (3.12 gm. 9.13 mmol) were dissolved in 75 ml of DMF and few drops of TEA were added and the reaction was stirred at RT. After, 2 hrs TLC on silica gel (5% MeOH+1% TEA+94 $CH_2Cl_2$) showed the formation of one major product less polar than starting material and another minor spot has lower Rf. The solvent was evaporated to dryness, then dissolved in $CH_2Cl_2$ and washed three times with a saturated solution of NaCl, dried the organic layer, evaporated to dryness to leave a yellow gummy material. This material was purified with column chromatography on silica gel by using (1% TEA+$CH_2Cl_2$) to (1% TEA+2.5% MeOH+$CH_2Cl_2$) as eluant. After evaporating the fractions containing the product, gave a yellowish solid material (3.16 g, 78%). HNMR and ES-MS confirmed the structure.

Synthesis of $N^6$-benzoyl-8-(4,7,10-trioxa-1-tridecaneaminobiotin)-5'-O-(4,4'-dimethoxytrityl)-2'-deoxyadenosine (3)

$N^6$-benzoyl-8-(4,7,10-trioxa-1-tridecaneaminobiotin)-3'-O-t-butyldimethylsilyl-5'-O-(4,4'-dimethoxytrityl)-2'-deoxyadenosine (3.16 gm, 2.6 mmol) was dissolved in 100 ml of dry THF, and then about (3.25 ml, 3.25 mmol) of tetrabutylammonium fluoride in THF was added in 5 min. while stirring at RT. After 8 hrs, TLC on silica gel (10% MeOH+1% TEA+89% $CH_2Cl_2$) showed that a new product with lower $R_f$ formed. The solvent was evaporated to give a yellow oily material. Column chromatography on silica gel eluted with (99% $CH_2Cl_2$+1% TEA) to (5% MeOH+1% TEA+94% $CH_2Cl_2$) permitted the purification of the product as a white foamy product (2.86 gm, 100%). HNMR and ES-MS confirmed the structure.

Synthesis of $N^6$-benzoyl-8-(4,7,10-trioxa-1-trideca-neaminobiotin)-3'-O-[(diisopropylamine)(2-cyanoethoxy)phosphino)]-5'-O-(4,4'-dimethoxytrityl)-2'-deoxyadenosine (4)

$N^6$-benzoyl-8-(4,7,10-trioxa-1-tridecaneaminobiotin)-5'-O-(4,4'-dimethoxytrityl)-2'-deoxyadenosine (0.959 gm, 0.86 mmol) was dissolved in a mixture of dry acetonitrile (200 ml) and dichloromethane (50 ml), and diisopropylamine (224 ul, 1.29 mmol) followed by the addition of 2-cyanoethyl N, N, N', N'-tetraisopropylphosphane (404 ul, 1.29 mmol) and tetrazole (2.6 ml, 1.2 mmol, 0.45 M solution in dry acetonitrile). The addition and subsequent reaction are performed under argon while stirring at RT. After 1.5 h, TLC on silica gel (5% MeOH+5% TEA+45% EA+45% $CH_2Cl_2$) showed that only about 50% of starting material (SM) was converted to a new product. The same above amount of reagents were added to the reaction and kept stirring for another 2 hrs at RT. TLC showed that about 95% of SM was converted to a new product with higher $R_f$. The solvent was evaporated to dryness then was dissolved in dichloromethane, extracted once with 5% solution of bicarbonate, followed by saturated brine solution and then dried over anhydrous sodium sulfate and evaporated to dryness. Column chromatography on silica gel (10% TEA+45% EA+45% $CH_2Cl_2$) first then (5% TEA+5% MeOH+45% EA+45% $CH_2Cl_2$). After evaporating the fractions containing the product, gave a yellow gummy material (774 mg). This material was co-evaporated three times from a mixture of dry benzene and dichloromethane, then was kept in desiccated containing $P_2O_5$ and NaOH pellets under vacuum for 24 hrs before used in DNA synthesis.

Synthesis of Oligonucleotides Containing Biotin-dC and Biotin-dA

The syntheses of oligonucleotides containing biotin-dC and Biotin-dA, site-specifically located, were performed on a CPG support using a fully automated DNA synthesizer and the commercially available fully protected deoxynucleosides phosphoramidites. Syntheses of all these oligonucleotides were carried out at 1.0 and 0.4 µmol scale. The coupling time for the biotin-dC and dA were extended to 900 seconds. The coupling efficiency of the biotin-dC and dA phosphoramidites was found greater than 96%. After coupling of the biotinylated phosphoramidites, the remaining residues comprising the eTAG reporter of interest were added. Upon completion of the synthesis of the oligonucleotides, they were deprotected with concentrated ammonia at 65° C. for 1 hour. These oligonucleotides were purified by reverse-phase HPLC and desalted by OPC column, then used as such.

Synthetic Preparation of ACLA1 on an ABI 394 DNA Synthesizer

6-Carboxyfluorescein (6-FAM) phosphoramidite is prepared by the addition of 2.96 ml of anhydrous acetonitrile to a 0.25 gram bottle of the fluorescein phosphoramidite, to give a 0.1M solution. The bottle is then loaded onto the ABI 394 DNA synthesizer at position 8 using the standard bottle change protocol. The other natural ($dA^{bz}$(0.1M: 0.25 g/2.91 mL anhydrous acetonitrile), $dC^{Ac}$(0.1M: 0.25 g/3.24 mL anhydrous acetonitrile), dT(0.1M: 0.25 g/3.36 mL anhydrous acetonitrile), $dG^{dmf}$(0.1M: 0.25 g/2.81 mL anhydrous acetonitrile) phosphoramidite monomers are loaded in a similar fashion to ports 1-4. Acetonitrile is loaded onto side port 18, standard tetrazole activator is loaded onto port 9, CAP A is loaded onto port 11, CAP B is loaded onto port 12, oxidant is loaded onto port 15, and deblock solution is loaded onto port 14 all using standard bottle change protocols.

Standard Reagents Employed for DNA Synthesis:
Oxidizer: 0.02 M Iodine (0.015 for MGB Probes)
DeBlock: 3% Trichloracetic Acid in Dichloromethane
Activator: 1H-Tetrazole in Anhydrous Acetonitrile
HPLC Grade Acetonitrile (0.002% water)
Cap A: Acetic Anhydride
Cap B: N-Methyl Imidazole.

The target sequence of interest is then input with a terminal coupling from port 8 to attach ACLA1 to the 5'-end of the sequence. A modified cycle is then chosen such that the desired scale (0.2(mol, 1.0(mol, . . . etc) of DNA is synthesized. The modified cycle contains an additional wait step of 800 seconds after any addition of 6-FAM. A standard DNA synthesis column containing the support upon which the DNA will be assembled is then loaded onto one of four positions of the DNA synthesizer. DNA containing eTag reporters have been synthesized on various standard 500 Å CPG supports (Pac-dA-CPG, dmf-dG-CPG, Ac-dC-CPG, dT-CPG) as well as specialty supports containing 3'-biotin, 3'-amino linker, and minor grove binding species.

Upon completion of the synthesis, the column is removed from the synthesizer and either dried under vacuum or by blowing air or nitrogen through the column to remove residual acetonitrile. The column is then opened and the CPG is removed and placed in a 1-dram vial. Concentrated ammonia is added (2.0 mL) and the vial is sealed and placed into a heat block set at 65° C. for a minimum of two hours. After two hours the vial is allowed to cool to room temperature after which the ammonia solution is removed using a Pasteur pipette and placed into a 1.5 mL Eppendorf tube. The solution is concentrated in vacuo and submitted for HPLC purification.

Synthetic Preparation of ACLA2 on an ABI 394 DNA Synthesizer

6-Carboxyfluorescein (6-FAM) phosphoramidite is prepared by the addition of 2.96 ml of anhydrous acetonitrile to a 0.25 gram bottle of the fluorescein phosphoramidite, to give a 0.1M solution. The bottle is then loaded onto the ABI 394 DNA synthesizer at position 8 using the standard bottle change protocol. The other natural ($dA^{bz}$(0.1M: 0.25 g/2.91 mL anhydrous acetonitrile), $dC^{Ac}$(0.1M: 0.25 g/3.24 mL anhydrous acetonitrile), dT(0.1M: 0.25 g/3.36 mL anhydrous acetonitrile), $dG^{dmf}$(0.1M: 0.25 g/2.81 mL anhydrous acetonitrile) phosphoramidite monomers are loaded in a similar fashion to ports 1-4. Acetonitrile is loaded onto side port 18, standard tetrazole activator is loaded onto port 9, CAP A is loaded onto port 11, CAP B is loaded onto port 12, oxidant is loaded onto port 15, and deblock solution is loaded onto port 14 all using standard bottle change protocols. The target sequence of interest is then input with a terminal coupling from port 8 and a penultimate coupling of thymidine to the 5'-end of the sequence to assemble ACLA2. A modified cycle is then chosen such that the desired scale (0.2 µmol, 1.0 µmol, . . . etc) of DNA is synthesized. The modified cycle contains an additional wait step of 800 seconds after any addition of 6-FAM. A standard DNA synthesis column containing the support upon which the DNA will be assembled is then loaded onto one of four positions of the DNA synthesizer. DNA containing eTag reporters have been synthesized on various standard 500 Å CPG supports (Pac-dA-CPG, dmf-dG-CPG, Ac-dC-CPG, dT-CPG) as well as specialty supports containing 3'-biotin, 3'-amino linker, and minor grove binding species.

Upon completion of the synthesis the column is removed from the synthesizer and either dried under vacuum or by blowing air or nitrogen through the column to remove residual acetonitrile. The column is then opened and the CPG is removed and placed in a 1-dram vial. Concentrated ammonia is added (2.0 mL) and the vial is sealed and placed into a heat block set at 65° C. for a minimum of two hours. After two hours the vial is allowed to cool to room temperature after which the ammonia solution is removed using a Pasteur pipette and placed into a 1.5 mL Eppendorf tube. The solution is concentrated in vacuo and submitted for HPLC purification.

Synthetic Preparation of ACLA3 on an ABI 394 DNA Synthesizer

6-Carboxyfluorescein (6-FAM) phosphoramidite is prepared by the addition of 2.96 ml of anhydrous acetonitrile to a 0.25 gram bottle of the fluorescein phosphoramidite, to give a 0.1M solution. The bottle is then loaded onto the ABI 394 DNA synthesizer at position 8 using the standard bottle change protocol. The other natural ($dA^{bz}$(0.1M: 0.25 g/2.91 mL anhydrous acetonitrile), $dC^{Ac}$(0.1M: 0.25 g/3.24 mL anhydrous acetonitrile), dT(0.1M: 0.25 g/3.36 mL anhydrous acetonitrile), $dG^{dmf}$(0.1M: 0.25 g/2.81 mL anhydrous acetonitrile) phosphoramidite monomers are loaded in a similar fashion to ports 1-4. Acetonitrile is loaded onto side port 18, standard tetrazole activator is loaded onto port 9, CAP A is loaded onto port 11, CAP B is loaded onto port 12, oxidant is loaded onto port 15, and deblock solution is loaded onto port 14 all using standard bottle change protocols. The target sequence of interest is then input with a terminal coupling from port 8 and two penultimate couplings of thymidine to the 5'-end of the sequence to assemble ACLA3. A modified cycle is then chosen such that the desired scale (0.2 umol, 1.0 (mol, . . . etc) of DNA is synthesized. The modified cycle contains an additional wait step of 800 seconds after any addition of 6-FAM. A standard DNA synthesis column containing the support upon which the DNA will be assembled is then loaded onto one of four positions of the DNA synthesizer. DNA containing eTags have been synthesized on various standard 500 Å CPG supports (Pac-dA-CPG, dmf-dG-CPG, Ac-dC-CPG, dT-CPG) as well as specialty supports containing 3'-biotin, 3'-amino linker, and minor grove binding species.

Upon completion of the synthesis, the column is removed from the synthesizer and either dried under vacuum or by blowing air or nitrogen through the column to remove residual acetonitrile. The column is then opened and the CPG is removed and placed in a 1-dram vial. Concentrated ammonia is added (2.0 mL) and the vial is sealed and placed into a heat block set at 65° C. for a minimum of two hours. After two hours the vial is allowed to cool to room temperature after which the ammonia solution is removed using a Pasteur pipet and placed into a 1.5 mL Eppendorf tube. The solution is concentrated in vacuo and submitted for HPLC purification.

Synthetic Preparation of ACLA16 on an ABI 394 DNA Synthesizer

6-Carboxyfluorescein (6-FAM) phosphoramidite is prepared by the addition of 2.96 ml of anhydrous acetonitrile to a 0.25 gram bottle of the fluorescein phosphoramidite, to give a 0.1M solution. The bottle is then loaded onto the ABI 394 DNA synthesizer at position 8 using the standard bottle change protocol. Spacer phosphoramidite C3 (0.25 g) is dissolved in 5.0 mL of anhydrous acetonitrile and loaded onto position 5 of the synthesizer. The other natural ($dA^{bz}$(0.1M: 0.25 g/2.91 mL anhydrous acetonitrile), $dC^{Ac}$(0.1M: 0.25 g/3.24 mL anhydrous acetonitrile), dT(0.1M: 0.25 g/3.36 mL anhydrous acetonitrile), $dG^{dmf}$(0.1M: 0.25 g/2.81 mL anhydrous acetonitrile) phosphoramidite monomers are loaded in a similar fashion to ports 1-4. Acetonitrile is loaded onto side port 18, standard tetrazole activator is loaded onto port 9, CAP A is loaded onto port 11, CAP B is loaded onto port 12, oxidant is loaded onto port 15, and deblock solution is loaded onto port 14 all using standard bottle change protocols. The target sequence of interest is then input with a terminal coupling from port 8 and a penultimate coupling of the C3 spacer from port 5 to assemble ACLA16. A modified cycle is then chosen such that the desired scale (0.2 μmol, 1.0 μmol, . . . etc) of DNA is synthesized. The modified cycle contains an additional wait step of 800 seconds after any addition of 6-FAM. A standard DNA synthesis column containing the support upon which the DNA will be assembled is then loaded onto one of four positions of the DNA synthesizer. DNA containing eTag reporters have been synthesized on various standard 500 Å CPG supports (Pac-dA-CPG, dmf-dG-CPG, Ac-dC-CPG, dT-CPG) as well as specialty supports containing 3'-biotin, 3'-amino linker, and minor grove binding species.

Upon completion of the synthesis the column is removed from the synthesizer and either dried under vacuum or by blowing air or nitrogen through the column to remove residual acetonitrile. The column is then opened and the CPG is removed and placed in a 1-dram vial. Concentrated ammonia is added (2.0 mL) and the vial is sealed and placed into a heat block set at 65° C. for a minimum of two hours. After two hours the vial is allowed to cool to room temperature after which the ammonia solution is removed using a Pasteur pipette and placed into a 1.5 mL Eppendorf tube. The solution is concentrated in vacuo and submitted for HPLC purification.

All other eTag reporters are synthesized in a similar manner to that described above.

FIGS. 2A-2I provide a list of different eTag reporters with their structures, where the symbols are as defined in Table 2 and are repeated here for convenience. $C_3$, $C_6$, $C_9$ and $C_{18}$ are commercially available phosphoramidite spacers from Glen Research, Sterling, Va. The units are derivatives of N,N-diisopropyl, O-cyanoethyl phosphoramidite, which is indicated by Q. The subscripts indicate the number of atoms in the chain, which comprises units of ethyleneoxy terminating in Q with the other terminus protected with DMT. The letters without subscripts A, T, C and G indicate the conventional nucleotides, while $T^{NH_2}$ intends amino thymidine and $C^{Br}$ intends bromocytidine. In FIG. 9, the numbers indicate the eTag reporter as numbered in FIGS. 2A-2I.

S1 Nuclease Digestion of eTag Reporter Probes

In a 1.5 ml tube, add 10 μl of eTag reporter probe at a concentration of 10 μM, add 1.5 μl of 10×S1 nuclease reaction buffer, add 0.5 μl of S1 nuclease (Promega, Cat#M5761, 20-100 unit/μl), and add 3 μl of Tris-EDTA buffer to bring the final volume to 15 μl. Incubate the reaction at 37° C. for 20 min followed by 25 min at 96° C. to inactivate the nuclease.

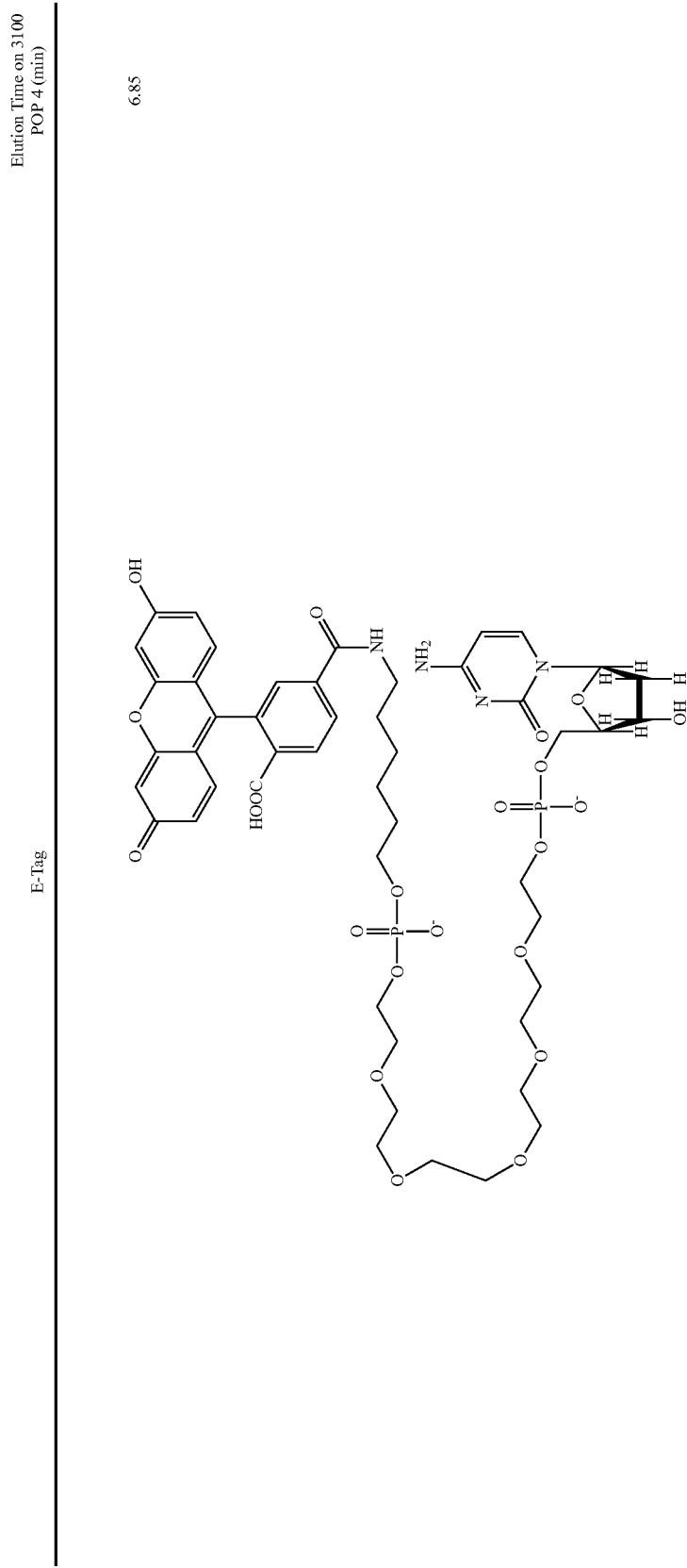

| -continued | | Elution Time on 3100 POP 4 (min) |
|---|---|---|
| | E-Tag 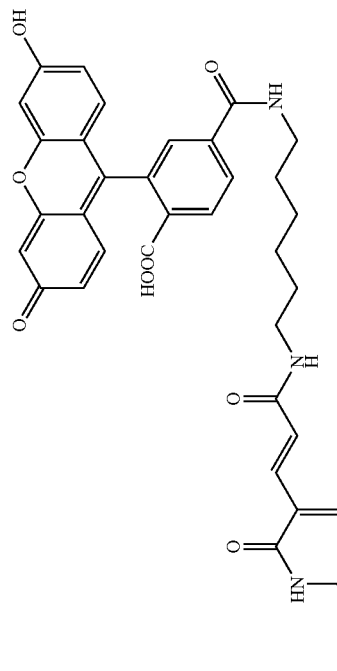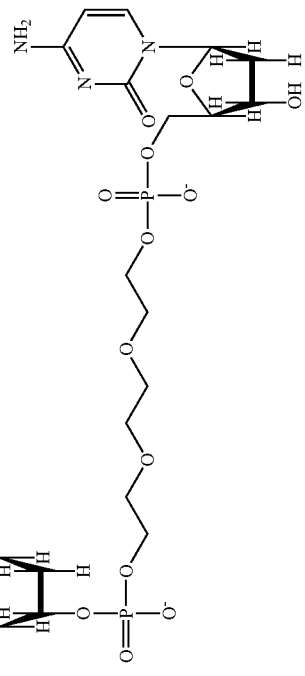 | 8.06 |

| -continued | |
|---|---|
| E-Tag | Elution Time on 3100 POP 4 (min) |
| 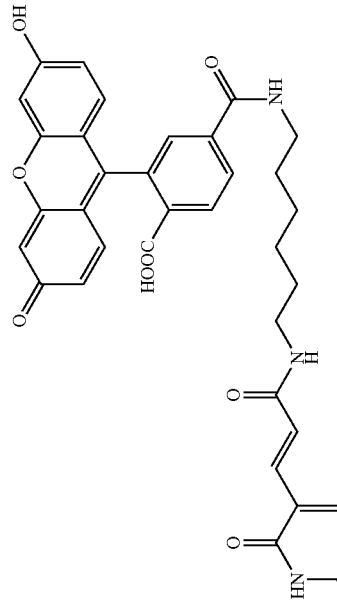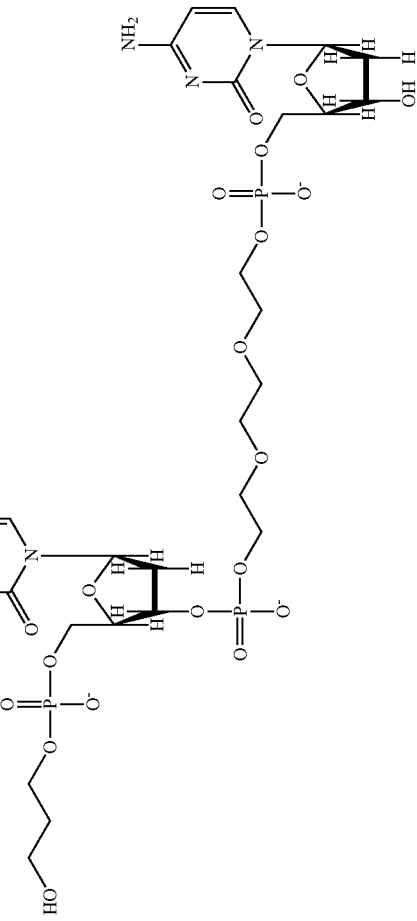 | 8.05 |

| E-Tag | Elution Time on 3100 POP 4 (min) |
|---|---|
| 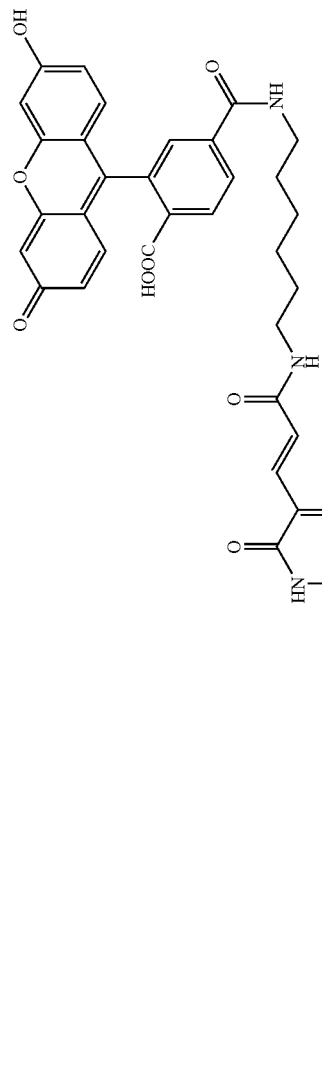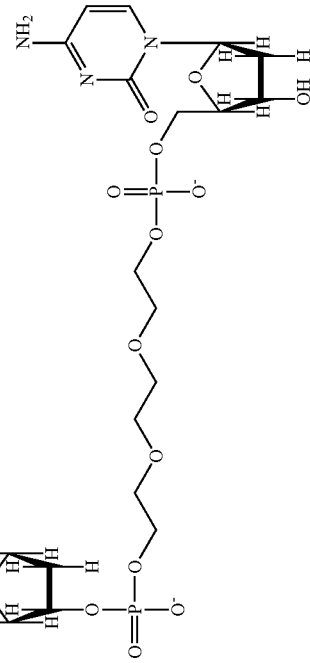 | 6.43 |

-continued
| E-Tag | Elution Time on 3100 POP 4 (min) |
|---|---|
| 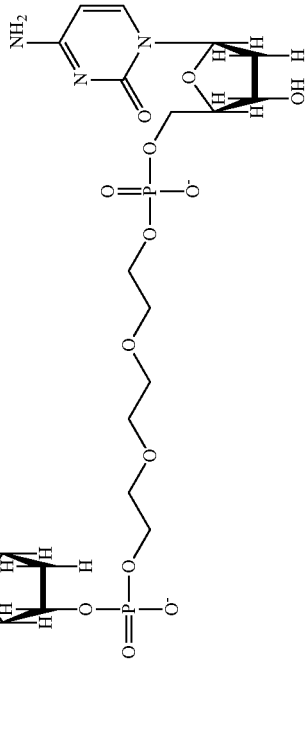 | 6.57 |

| E-Tag | Elution Time on 3100 POP 4 (min) |
|---|---|
| 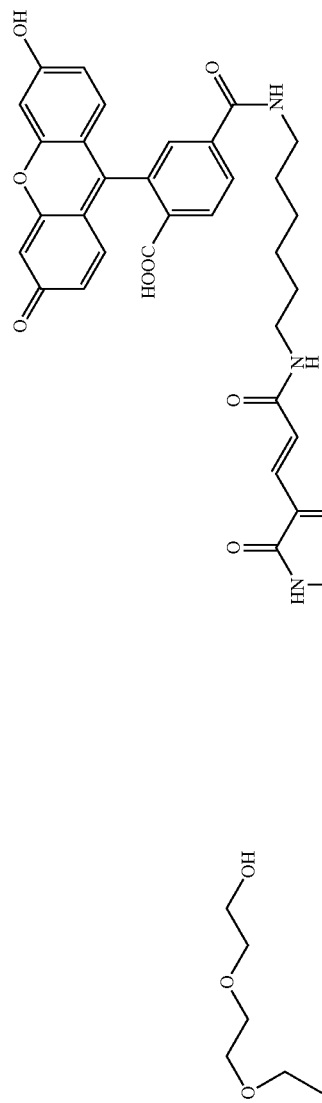 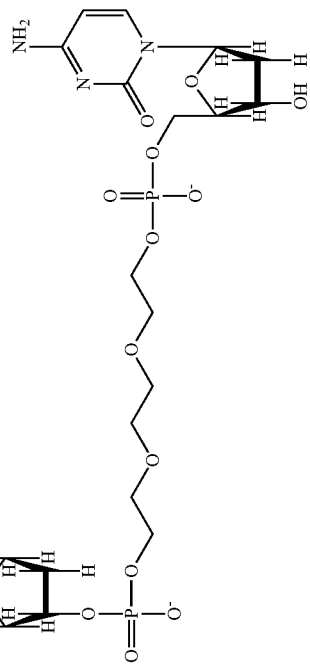 | 7.02 |

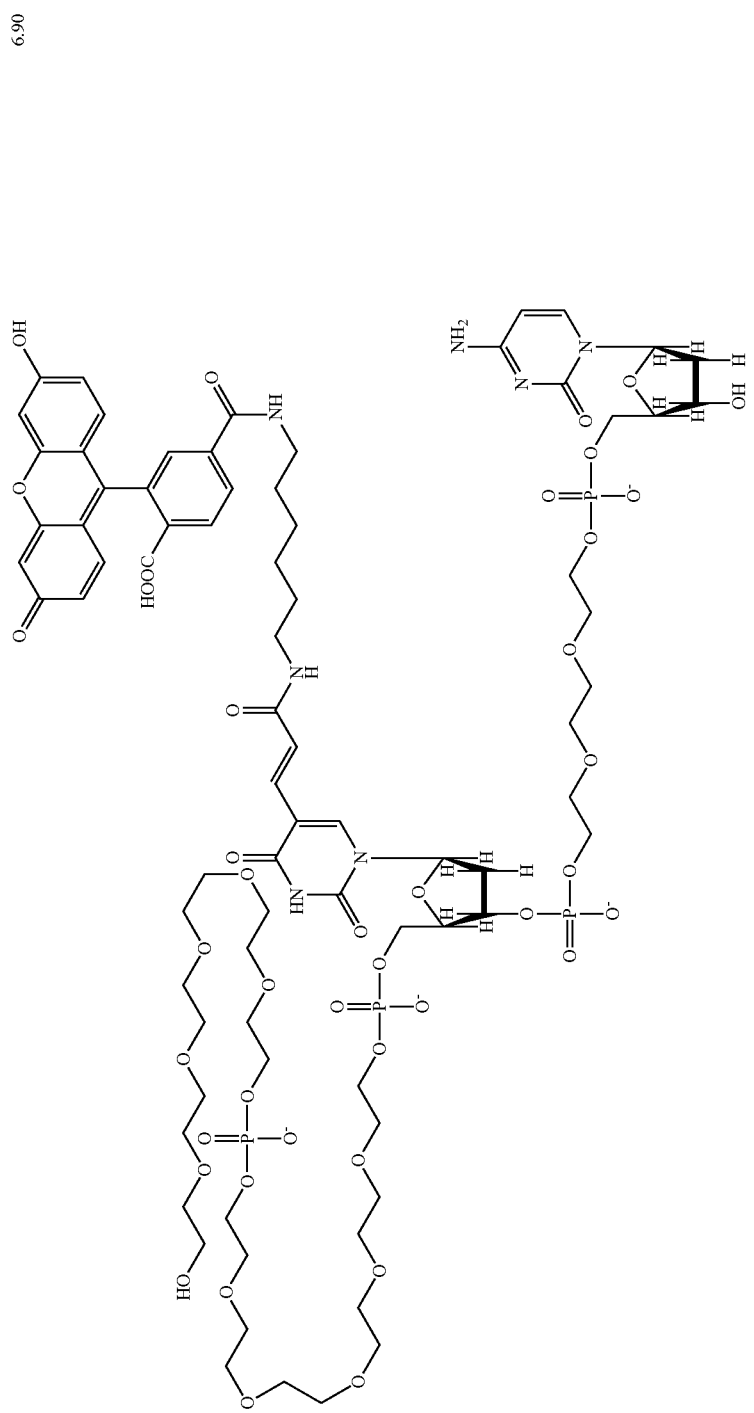

| E-Tag | Elution Time on 3100 POP 4 (min) |
|---|---|
| 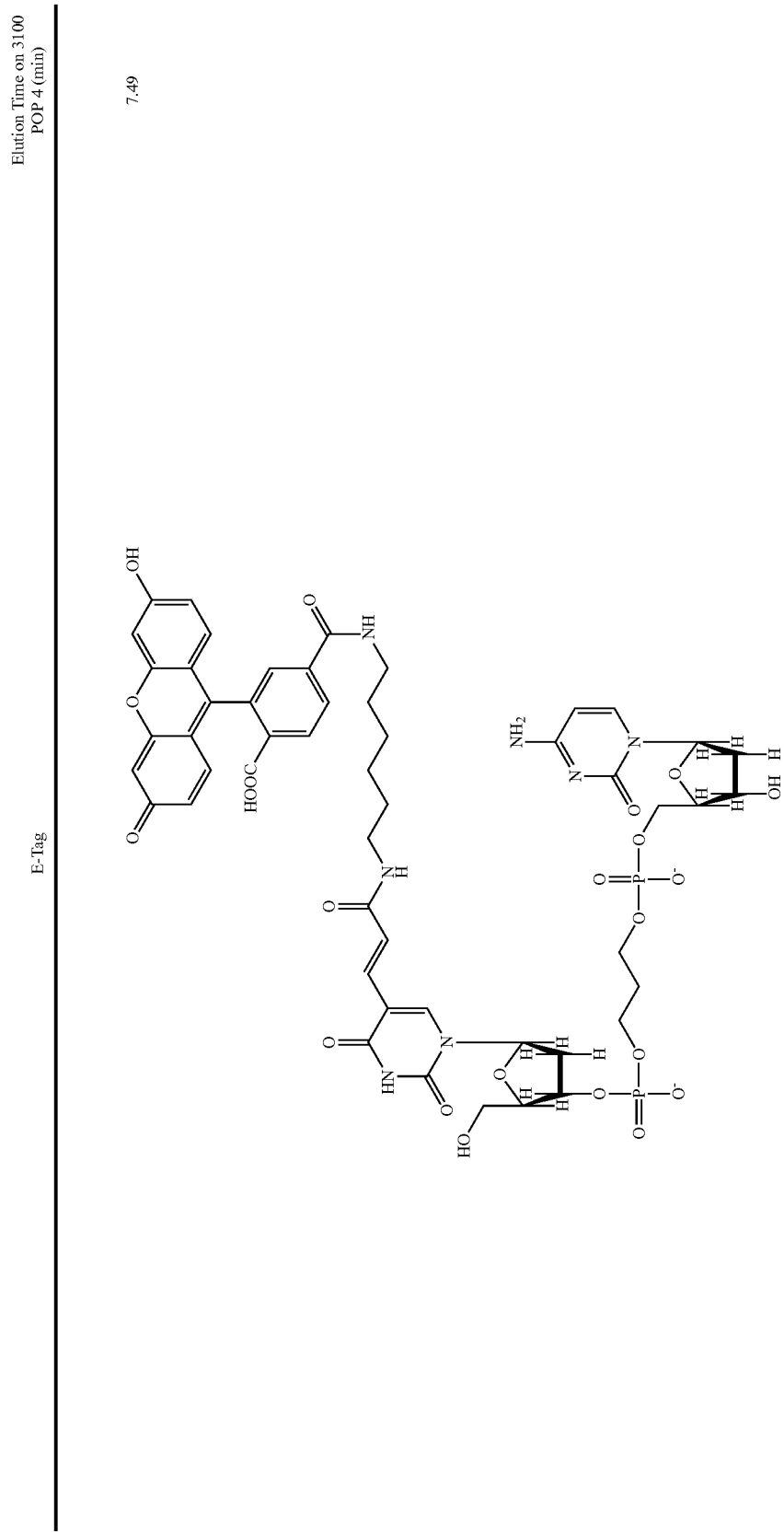 | 7.49 |

| E-Tag | Elution Time on 3100 POP 4 (min) |
|---|---|
| 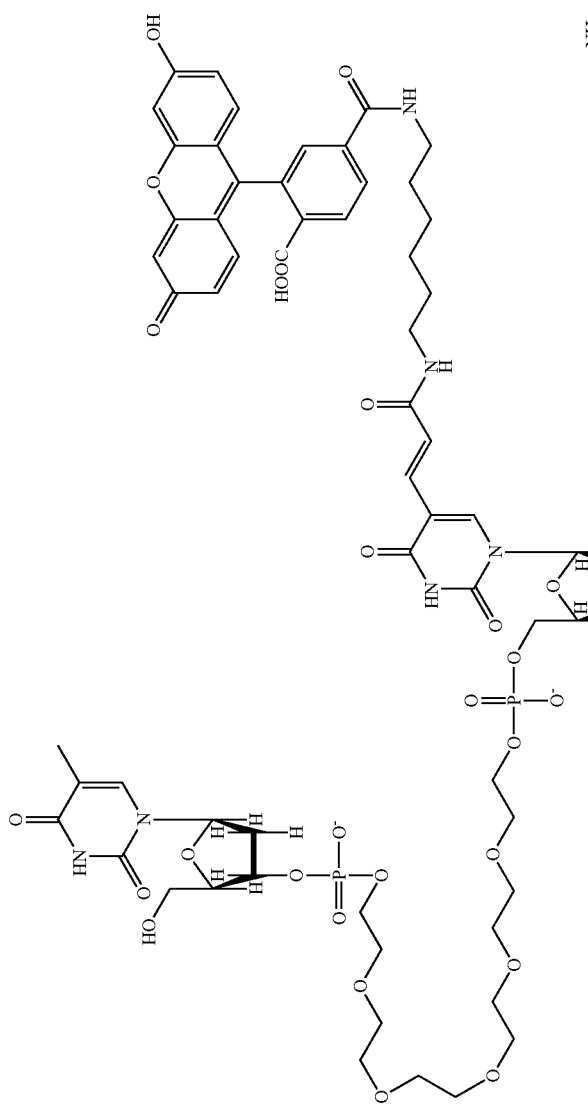 | 5.81 |

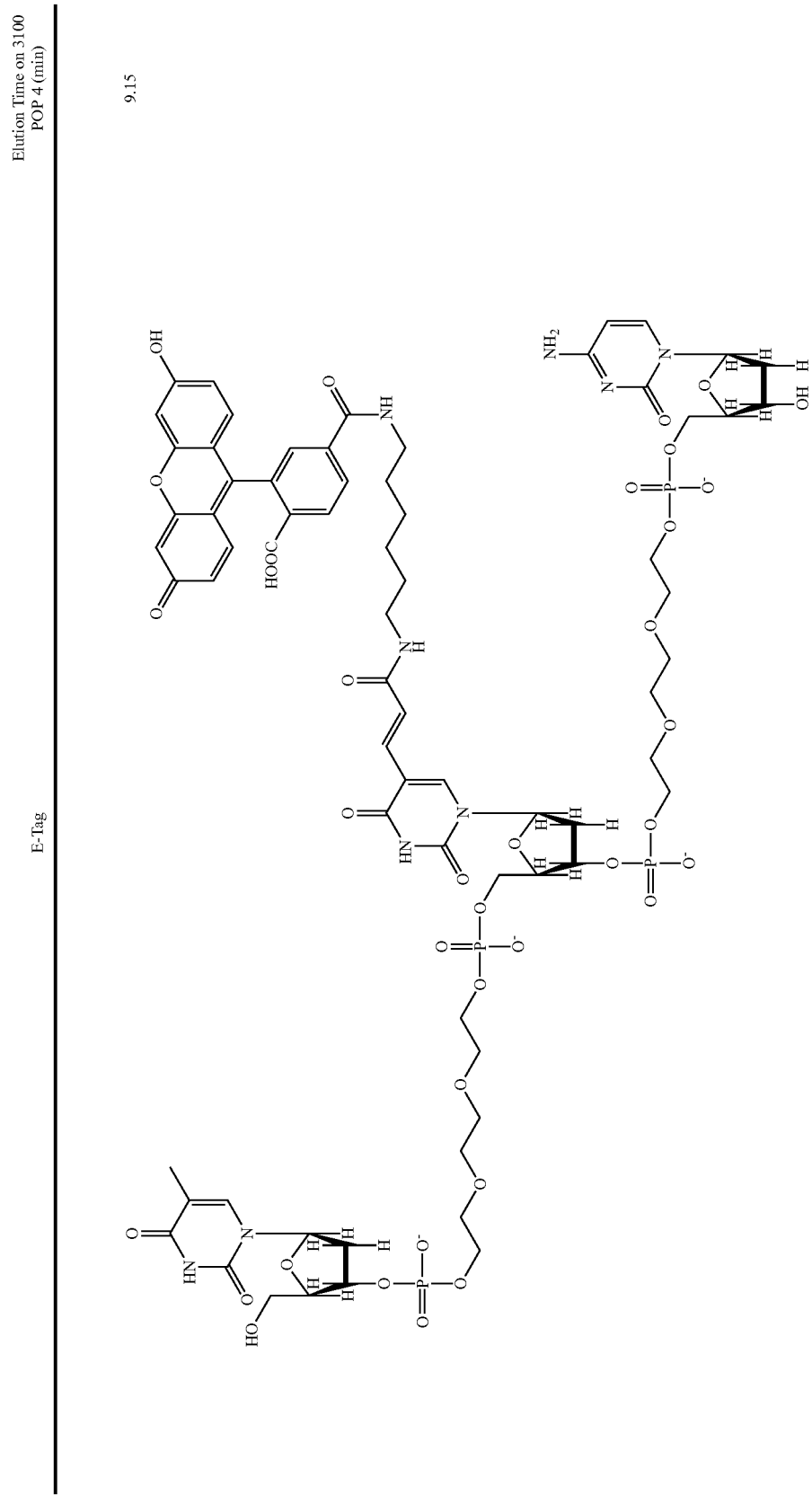
| E-Tag | Elution Time on 3100 POP 4 (min) |
|---|---|
| | 9.15 |

| -continued | | |
|---|---|---|
| | E-Tag | Elution Time on 3100 POP 4 (min) |
| | 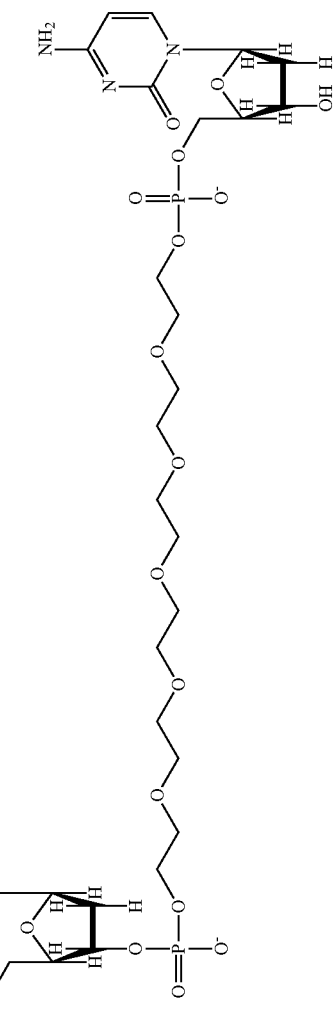 | 6.43 |

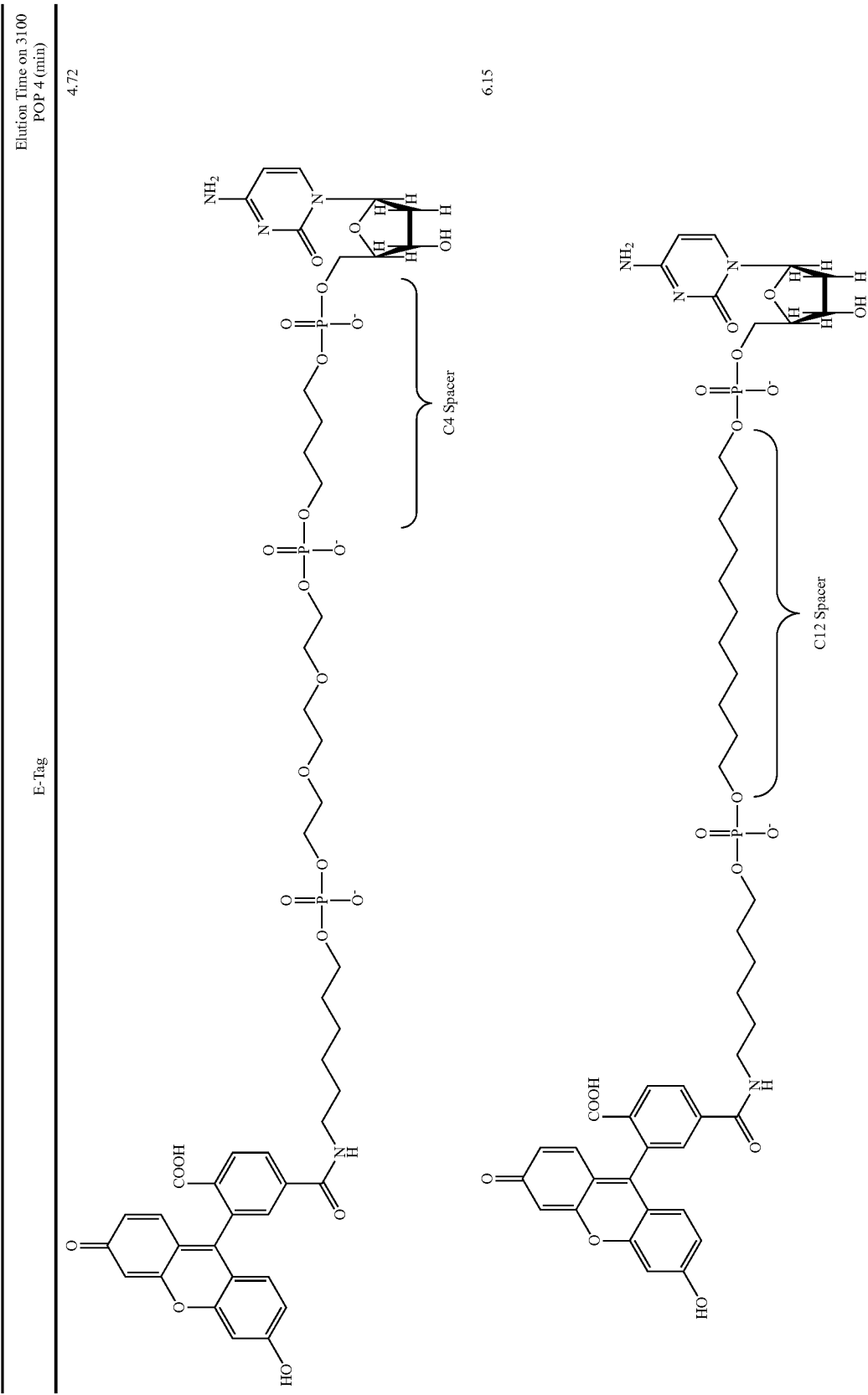

-continued

| E-Tag | Elution Time on 3100 POP 4 (min) |
|---|---|
| | 3.82 |
| | 4.55 |
| | 4.26 |
| | 4.45 |
| | 3.51 |
| | 2.98 |
| | 4.50 |

TABLE 6

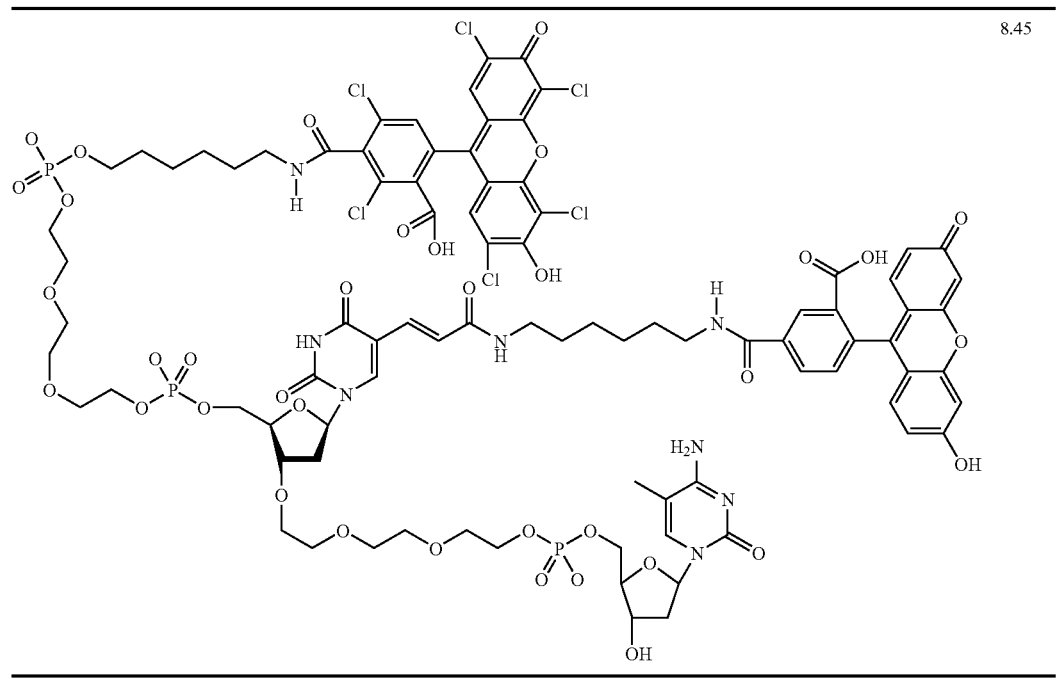

8.45

5'Nuclease Assays for Monitoring Specific mRNA Expression in Cell Lysates

THP-1 cells (American Type Culture Collection, Manassas, Va.) were cultured in the presence or absence of 10 nM phorbol 12-myristate 13-acetate (Sigma-Aldrich, St. Louis, Mo.) in RPMI 1640 medium with 10% fetal bovine serum (v/v), 2 mM L-glutamine, 10 mM HEPES, 0.05 mM 2-mercaptoethanl. Twenty-four hours after the induction, cells were harvested and washed twice with PBS before lysed with lysis buffer (20 nM Tris pH7.5, 0.5% Nonidet P-40, 5 mM MgCl2, 20 ng/ul tRNA) at 25° C., for 5 min. The lysate was heated at 75° C. for 15 min before tested in 5' nuclease assay.

Figure 8:
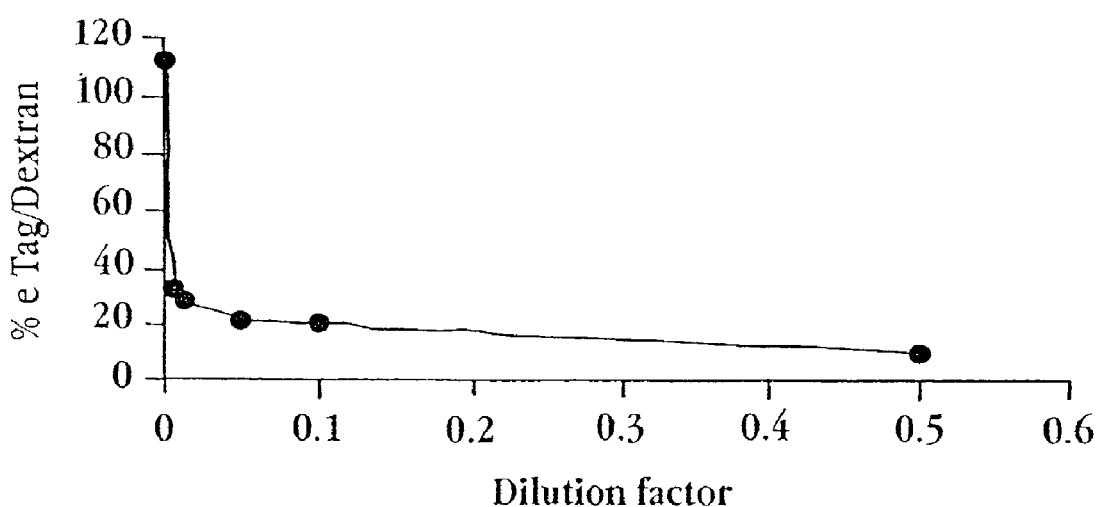
FIG. 8 is a data curve showing the effect of the concentration of labeled aminodextran on the eTag reporter release, demonstrated in this figure, the lower concentration of labeled aminodextran for a given concentration of sensitizer beads leads to more efficient eTag reporter release (or higher ratio of eTag reporter released to the amount of labeled aminodextran). Results were obtained using a $CE^2$ LabCard. Experimental conditions: Separation buffer 20.0 mM HEPES pH=7.4, and 0.5% PEO; voltage configurations as shown in FIG. 3; assay mixture had 29 μg/ml of sensitizer beads and was irradiated for 1 min at 680 nm using 680±10 nm filter and a 150 W lamp.

Ten microliter cell lysate was combined with a single stranded upstream invader DNA oligo, (5'CTC-TCA-GTT-CT) (SEQ ID NO: 1), a single stranded downstream biotinylated signal DNA oligo (eTag-labeled), and 2 ng/ul 5' nuclease (Cleavase IX) in 20 ul of buffer (10 mM MOPS pH 7.5, 0.05% Tween-20 and 0.05% Nonidet P-40, 12.5 mM MgCl2, 100 uM ATP, 2 U/ul Rnase inhibitor). The reactions were carried out at 60° C. for 4 hours before analyzed by capillary electrophoresis. To eliminate background signal, due to the non-specific activity of the enzyme, 1 ul of 1 mg/ml avidin was added to the reactions to remove all the eTag-labeled uncleaved oligo, or eTag-labeled non-specifically cleaved oligos. FIGS. 8 and 9 show separations that were conducted both with and without the addition of avidin.

PCR Amplification with 5' Nuclease Activity Using eTag Reporters

The eTag reporters are described in FIGS. 2A-2I. The eTag reporters that were prepared were screened to provide 20 candidates that provided sharp separations. 31 eTag reporters were generated with synthetic targets using the TaqMan (reagents under conditions as shown in the following tabular format. There were 62 reactions with the synthetic targets (1 reaction and one negative control for eTag reporter). The master mix involves preparing a solution of TaqMan master mix, primer (both reverse and forward) and water. This mix is then aliquoted into individual PCR tubes followed by the addition of probe and template.

| Stock | Stock Conc. | Volume (1 (25(μl/reax) | Final conc. | Master mix | (Vol*64) |
|---|---|---|---|---|---|
| TagMan mix | 2× | 6.25 | 0.5× | 400 | |
| Probe (eTag reporter) | 4 μM | 1.25 | 200 nM | | |
| Primer | 5 μM | 2.5 | 500 nM | 160 | |
| Template | 100 fM | 1.25 | 5 fm | | |
| Water | | 13.75 | | 880 | |
| | Total | 25 μl | | | 1440/64 = 22.5 (+1.25 μl (probe) + 1.25 μl (template) = 25 μl.reax |

All the individual reactions were then run on an ABI 3100 using POP4 as the separation matrix. The samples were diluted 1:20 in 0.5× TaqMan buffer and 1(1 of avidin (10 mg/ml) was added to bind to any intact probe. The sample was further diluted 1:2 with formamide before injecting the sample into the ABI 3100 capillaries. The following on the conditions used with the ABI 3100 for the separation.

| | |
|---|---|
| Temperature | 60 (C. |
| Pre-run voltage | 15 KV |
| Pre-run time | 180 sec |
| Matrix | POP4 |
| Injection voltage | 3 KV |
| Injection time | 10 sec |
| Run voltage | 15 KV |
| Run time | 900 sec |
| Run module | eTag reporter POP4 |
| Dye set | D |

Subsequent separation of multiple eTAG reporters in a single run were accomplished as shown in FIG. 9, the structures of which are identified in FIGS. 2A-2I.

eTag Reporter Proteomic Analog Assay

1-Labeling of Aminodextran (MW ~500,000) with eTag Reporter and Biotin.

Aminodextran was used as a model for demonstrating eTag reporter release in relation to a high molecular weight molecule, which also serves as a model for proteins. The number of amino groups for 10 mg aminodextran was calculated as $2 \times 10^{-8}$ moles. For a ratio of 1:4 biotin to eTag reporter, the number of moles of biotin NHS ester employed was $1.85 \times 10^{-6}$ and the number of moles of maleimide NHS ester was $7.4 \times 10^{-6}$. 10.9 mg of aminodextran was dissolved in 6 ml of 0.1% PBS buffer. Then, 10 mg of Biotin-x-x NHS ester and 23.7 mg of EMCS were dissolved together in 1 ml of DMF. This DMF solution was added in 50 µl portion (30 min interval) to the aminodextran solution while it was stirring and keeping away from the light. After final addition of the DMF solution, the mixtured was kept overnight (while stirring and away from the light). Then, the mixture was dialyzed using membrane with cut off molecular weight of 10,000. The membrane immersed in a beaker containing 2 l of water while stirring. This water was changed four times (2 h interval). The membrane was kept in the water overnight (while stirring and keeping away from the light). Then the solution was lyophilized and the lyophilized powder was used for eTag reporter labeling.

2-Reaction of Biotin and Maleimide Labeled Aminodextran with the eTag Reporter, SAMSA.

SAMSA [5-((2-(and-3)-S-acetylmercapto)succinoyl) amino)fluorescein]was employed as an eTag reporter to react with maleimide in the aminodextran molecule. For this purpose 0.3 mg (~$5.3 \times 10^{-9}$ moles) of biotin and EMCS labeled with aminodextran were dissolved in 10 µl of water and then reacted with 10 times the mol ratio of SAMSA, for the complete conversion of the maleimide to the eTag reporter. Therefore, 1.1 mg of SAMSA (~$1.2 \times 10^{-6}$ moles) is dissolved in 120 µl of 0.1 M NaOH and incubated at room temperature for 15 min (for the activation of the thiol group). Then the excess of NaOH was neutralized by the addition of 2 µl of 6M HCl, and the pH of the solution was adjusted to 7.0 by the addition of 30 µl of phosphate buffer (200 mM, pH=7.0). The activated SAMSA solution was added to the 10 µl solution of the labeled aminodextran and incubated for 1 h. The eTag reporter labeled aminodextran was purified with gel filtration using Sephadex G-25 (Amersham), and purified samples were collected.

3—The Release of eTag from Labeled Aminodextran.

Figure 3:
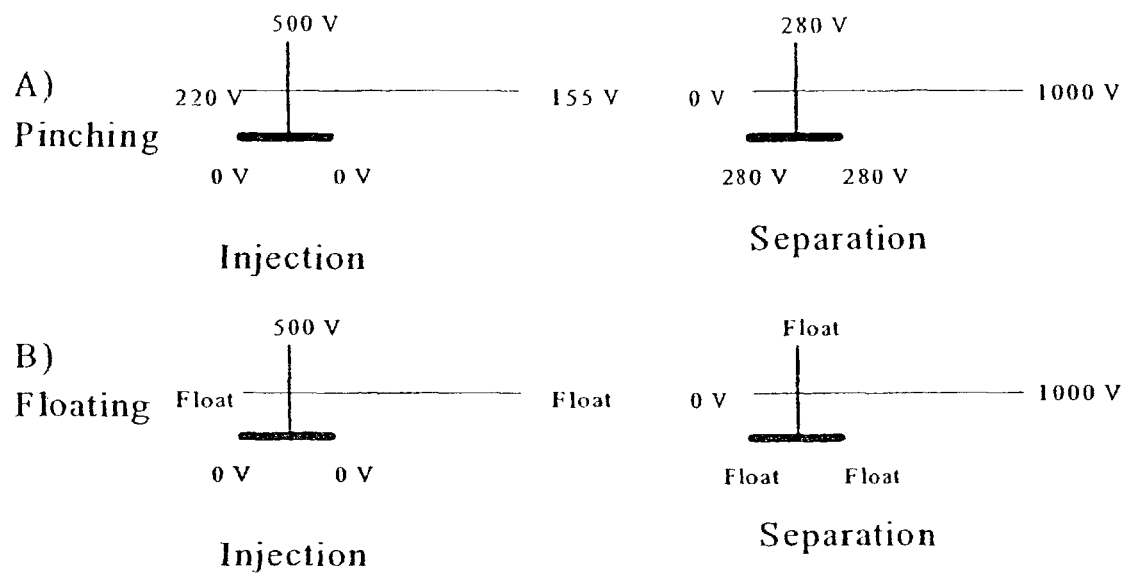
FIG. 3 is a schematic illustrating exemplary high voltage configurations utilized in a $CE^2$ LabCard™ device during an enzyme assay.

2 µl of streptavidin coated sensitizer beads (100 µg/ml) were added carefully in the dark to the 5 µl of purified labeled aminodextran and incubated in the dark for 15 min. Then the solution was irradiated for 1 min at 680 nm. The release of the eTag reporter was examined be CE using $CE^2$ LabCard™ device. As shown in FIG. 3, the $CE^2$ LabCard consists of two parts; evaporation control and injection/separation. The evaporation control incorporates a channel (450 µm wide and 50 µm deep) with two buffer reservoirs (2 mm in diameter) and the evaporation control well (1 mm diameter) right in the center of the channel. The volume of the side wells (replenishment wells) are 4.7 µl while the volume of the middle well is only 1.2 µl and the volume of the channel beneath the middle well is about 40 nl. The second part of the $CE^2$ device which is the injection/separation part consists of injection and separation channels with dimensions of 120 µm wide and 50 µm deep. The injection channel is connected directly to the evaporation control well. The channels are closed by laminating a film (MT40) on the LabCard™.

After filling the $CE^2$ LabCard device with the separation buffer (20 mM HEPES, pH=7.4 and 0.5% PEO), 300 nl of the assay mixture was added to the middle well (sample well) and separated by CE as is shown in FIG. 3.

Figure 4:
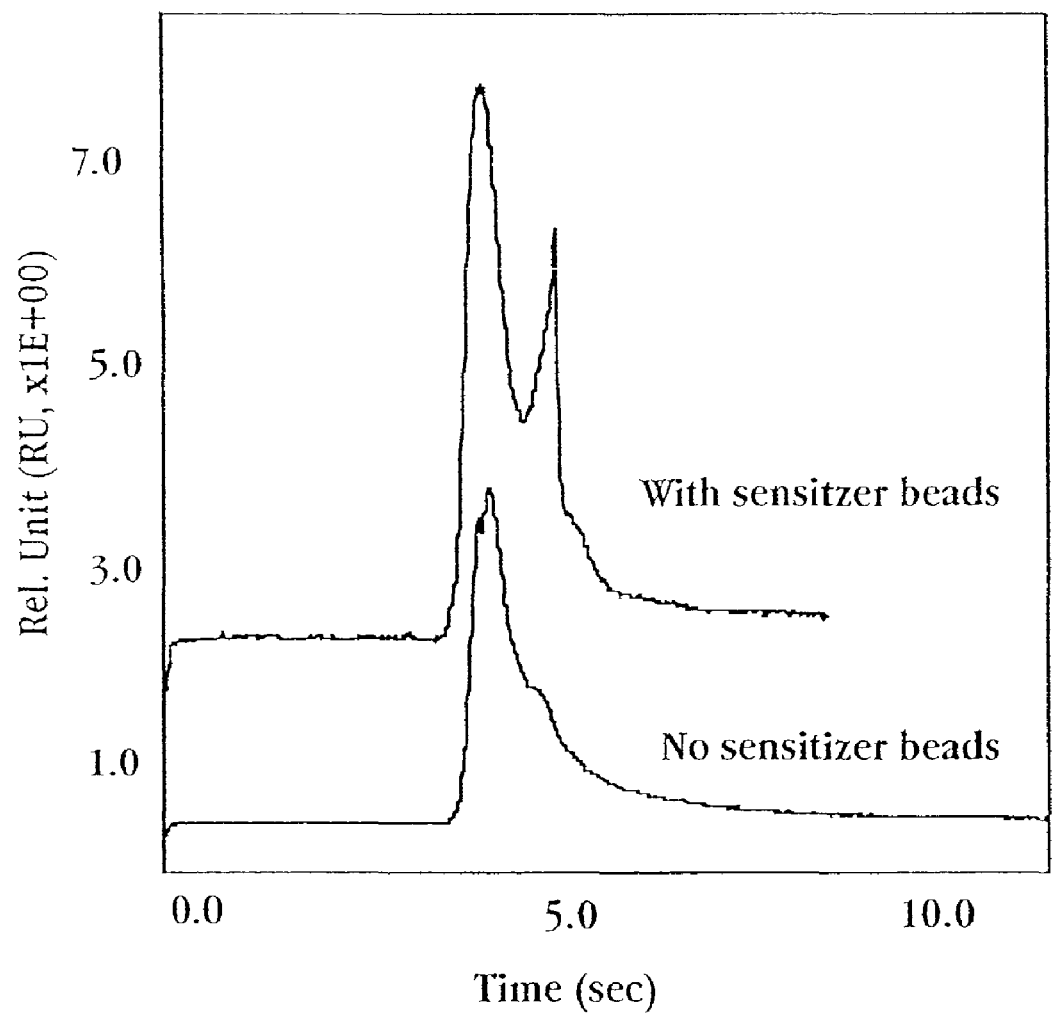
FIG. 4 is two electropherograms demonstrating eTag reporter analysis using a $CE^2$ LabCard. The figure shows the separation of purified labeled aminodextran with and without sensitizer beads. The addition of the sensitizer beads lead to the release of the eTag reporter from the aminodextran using singlet oxygen produced by sensitizer upon the irradiation at 680 nm. Experimental conditions: Separation buffer 20.0 mM HEPES pH=7.4, and 0.5% PEO; voltage configurations as shown in FIG. 3; assay mixture had 29 µg/ml streptavidin coated sensitizer beads and irradiated for 1 min at 680 nm using 680±10 nm filter and a 150 W lamp.
Figure 5:
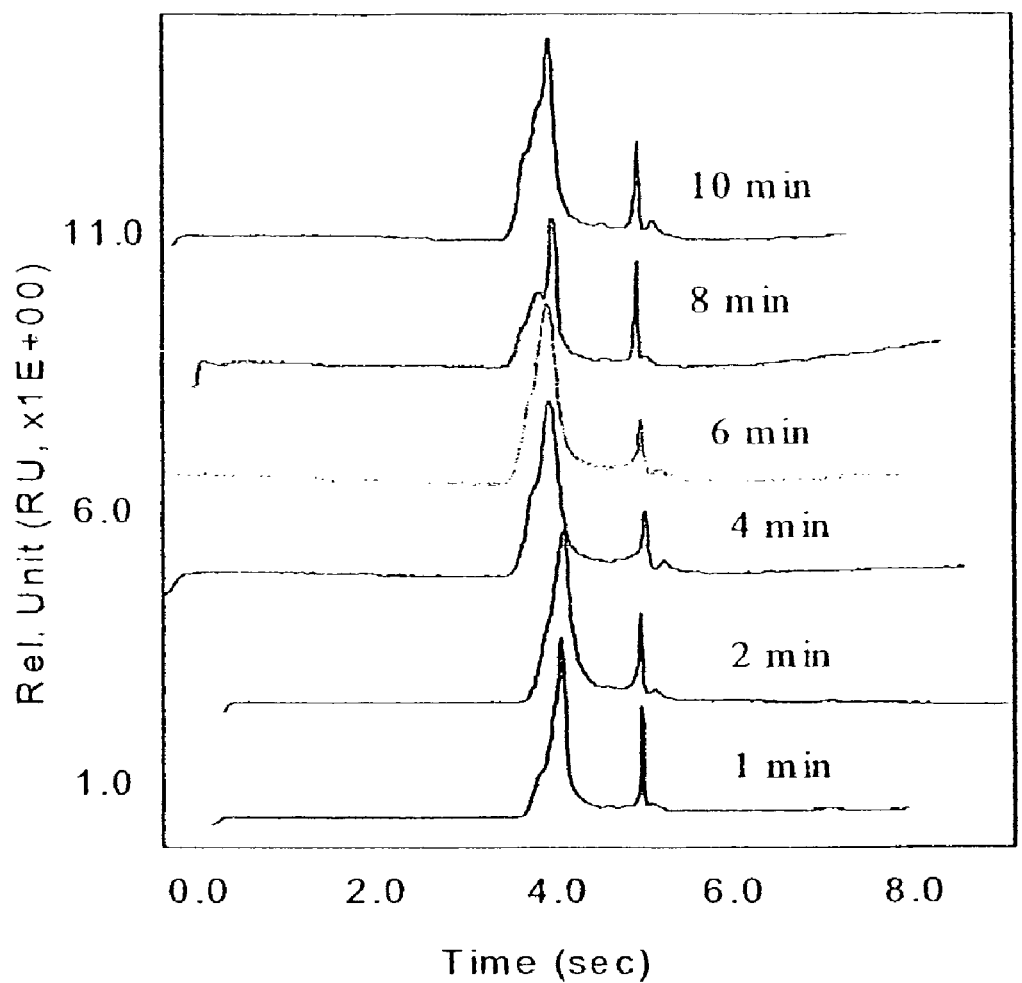
FIG. 5 is multiple electropherograms demonstrating eTag reporter analysis using a $CE^2$ LabCard. The figure shows the separation of purified labeled aminodextran that has been irradiated for different lengths of time. Experimental conditions: Separation buffer 20.0 mM HEPES pH=7.4, and 0.5% PEO; voltage configurations as shown in FIG. 3; assay mixture had 27 µg/ml streptavidin coated sensitizer beads and irradiated at 680 nm using 680±10 nm filter and a 150 W lamp.
Figure 6:
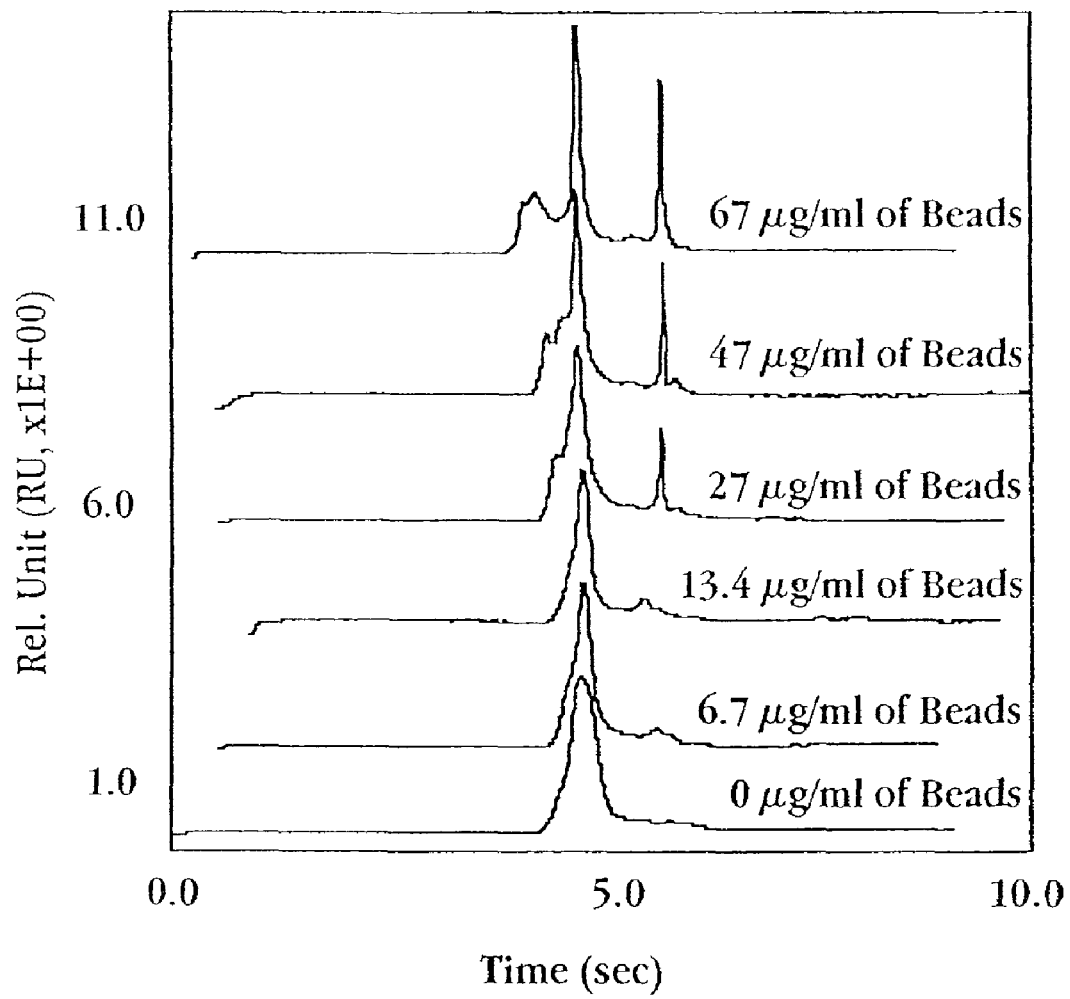
FIG. 6 is multiple electropherograms demonstrating eTag reporter analysis using a $CE^2$ LabCard. The figure shows the separation of purified labeled aminodextran using different concentrations of sensitizer beads. The higher concentration of sensitizer beads leads to the higher release of eTag reporters from the labeled aminodextran. Experimental conditions: Separation buffer 20.0 mM HEPES pH=7.4, and 0.5% PEO; voltage configurations as shown in FIG. 3; assay mixture was irradiated for 1 min at 680 nm using 680±10 nm filter and a 150 W lamp.
Figure 7:
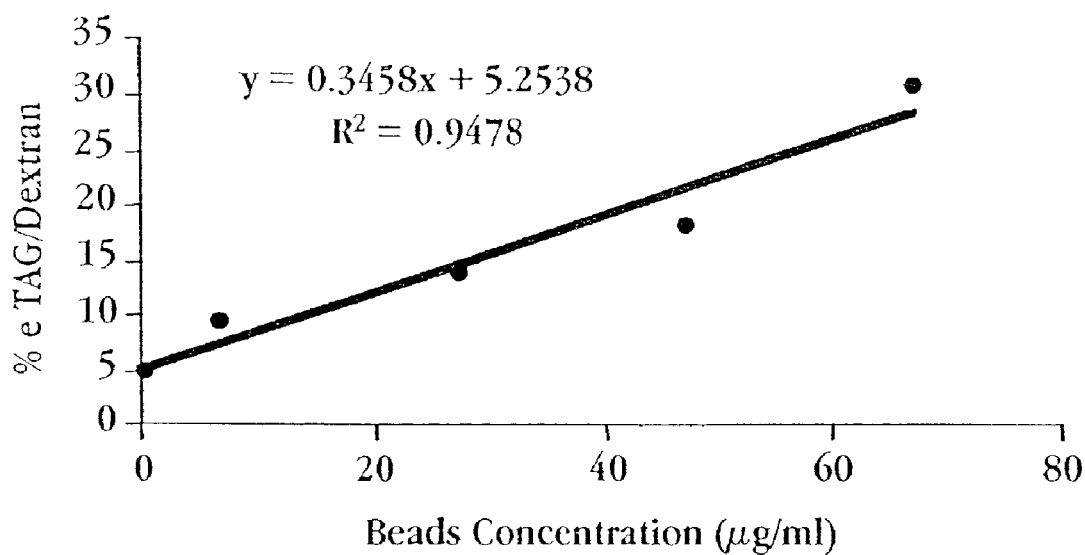
FIG. 7 depicts the linear calibration curve for the release of eTag reporters as a function of the sensitizer bead concentration. Results were obtained using a $CE^2$ LabCard. Experimental conditions: Separation buffer 20.0 mM HEPES pH=7.4, and 0.5% PEO; voltage configurations as shown in FIG. 3; assay mixture was irradiated for 1 min at 680 nm using 680±10 nm filter and a 150 W lamp.

FIG. 4 shows the electropherograms of purified labeled aminodextran with and without sensitizer beads. As shown, the addition of the sensitizer beads lead to the release of the eTag reporter from the aminodextran using singlet oxygen produced by sensitizer upon the irradiation at 680 nm. In order to optimize the irradiation time, different tubes containing the same mixture of beads and sensitizer were irradiated for different lengths of time ranging from 1 to 10 min. There is no significant increase in the eTag reporter release for irradiation longer than 1 min. FIG. 6, shows the effect of sensitizer bead concentration on the eTag reporter release. As depicted in FIG. 6, the higher concentration of sensitizer beads leads to the higher release of eTag reporters from the labeled aminodextran. FIG. 7 depicts the linear calibration curve for the release of eTag reporters as a function of the sensitizer bead concentration. In addition, the effect of the concentration of labeled aminodextran on the eTag reporter release was also examined and the result is shown in FIG. 8. As can be seen, the lower concentration of labeled aminodextran for a given concentration of sensitizer beads leads to more efficient eTag reporter release (or higher ratio of eTag reporter released to the amount of labeled aminodextran).

It is evident from the above results that the subject inventions provide powerful ways of preparing compositions for use in multiplexed determinations and for performing multiplexed determinations. The methods provide for homogeneous and heterogeneous protocols, both with nucleic acids and proteins, as exemplary of other classes of compounds. In the nucleic acid determinations, snp determinations are greatly simplified where the protocol can be performed in only one to four vessels and a large number of snps readily determined within a short period of time with great efficiency and accuracy. For other sequences, genomes can be investigated from both prokaryotes and eukaryotes, including for the prokaryotes, drug resistance, species, strain, etc. and for the eukaryotes, species, cell type, response to external stimuli, e.g. drugs, physical changes in environment, etc., mutations, chiasmas, etc. With proteins, one can determine the response of the host cell, organelles or the like to changes in the chemical and physical environments in relation to a plurality of pathways, changes in the surface protein population, changes due to aging, neoplasia, activation, or other naturally occurring phenomenon, where the amount of protein can be quantitated.

Particularly as to nucleic acid determinations, the subject eTag reporters can be synthesized conveniently along with the synthesis of the oligonucleotides used as probes, primers, etc., where the eTag reporter is released in the presence of the homologous target sequence. Kits of building blocks or eTag reporters are provided for use in the different determinations.

All publications and patent applications mentioned in this specification are indicative of the level of skill of those skilled in the art to which this invention pertains. All publications and patent applications set forth herein are incorporated by reference to the same extent as if each individual publication or patent application was specifically and individually indicated to be incorporate by reference.

The invention now having been fully described, it will be apparent to one of ordinary skill in the art that many changes and modifications can be made thereto without departing from the spirit or scope of the appended claims.

What is claimed is:

1. A method of performing a multiplexed assay for the determination of a plurality of target proteins in a sample, the method comprising the steps of:
   providing a binding compound consisting of an antibody or antibody fragment thereof for each of the plurality of target proteins, each binding compound having one or more eTag reporters attached thereto by a cleavable linkage, the one or more eTag reporters of each different binding compound having a different electrophoretic mobility after cleavage so that eTag reporters of each different binding compound form distinct peaks after electrophoretic separation;
   combining with the sample the binding compound and a second binding compound consisting of an antibody or antibody fragment thereof for each of the plurality of target proteins, wherein the second binding compound is conjugated with an active species producing moiety for generating an active species for oxidizing the cleavable linkage, such that in the presence of a target protein a complex is formed between each target protein and the binding compound(s) specific therefor;
   cleaving each cleavable linkage by oxidation where said step includes providing the active species consisting of singlet oxygen for oxidizing the cleavable linkage thereby so that eTag reporters are released; and
   electrophoretically separating and identifying the released eTag reporters to determine the plurality of target proteins in the sample.

2. The method of claim 1 further including a step prior to said step of cleaving, the step comprising separating said complexes from unbound binding compounds.

3. The method of claim 2 wherein each of said eTag reporters has a fluorescent label or an electrochemical label.

4. The method of claim 1 wherein said released eTag reporters have a charge opposite that of said complexes and said binding compounds, wherein said cleavable linkage is cleaved by oxidation, and wherein said step of cleaving includes providing an active species for oxidizing said cleavable linkage.

5. A method of performing a multiplexed assay for the determination of a plurality of target species in a sample, the method comprising the steps of:
   providing a binding compound consisting of an antibody or antibody fragment thereof for each of a plurality of target species, the target species being a plurality of surface membrane proteins, each binding compound having one or more eTag reporters attached thereto by a cleavable linkage, the one or more eTag reporters of each different binding compound having a different mass/charge ratio or adsorption so that eTag reporters of each different binding compound form distinct peaks upon electrophoretic separation or chromatographic separation;
   providing a second binding compound consisting of an antibody or antibody fragment thereof for each of the plurality of target species, each second binding compound being conjugated with an active species producing moiety for generating the active species for oxidizing the cleavable linkage;
   combining with the sample, the binding compound and the second binding compound for each of the plurality of target species such that in the presence of a target species a complex is formed between target species and the binding compound and the second binding compound specific therefor, and such that the active species producing moiety of the second binding compound causes the generation of an active species consisting of singlet oxygen for oxidizing the cleavable linkage and cleaves the cleavable linkages to release one or more eTag reporters; and
   electrophoretically or chromotographically separating and identifying the released eTag reporters to determine the plurality of target species in the sample.

6. The method of claim 5, wherein each of said one or more eTag reporters of each said different binding compound has a different mass/charge ratio so that said eTag reporters of each of said different binding compound forms a distinct peak upon electrophoretic separation.

* * * * *